US012624085B2

(12) United States Patent
Powell et al.

(10) Patent No.: US 12,624,085 B2
(45) Date of Patent: May 12, 2026

(54) COMPOSITIONS AND METHODS OF NKG2D CHIMERIC ANTIGEN RECEPTOR T CELLS FOR CONTROLLING TRIPLE-NEGATIVE BREAST CANCER

(71) Applicant: THE TRUSTEES OF THE UNIVERSITY OF PENNSYLVANIA, Philadelphia, PA (US)

(72) Inventors: Daniel Powell, Bala Cynwyd, PA (US); De-Gang Song, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1270 days.

(21) Appl. No.: 17/255,108

(22) PCT Filed: Jun. 24, 2019

(86) PCT No.: PCT/US2019/038739
§ 371 (c)(1),
(2) Date: Dec. 22, 2020

(87) PCT Pub. No.: WO2020/005837
PCT Pub. Date: Jan. 2, 2020

(65) Prior Publication Data
US 2021/0269501 A1 Sep. 2, 2021

Related U.S. Application Data

(60) Provisional application No. 62/689,552, filed on Jun. 25, 2018.

(51) Int. Cl.

| | |
|---|---|
| *C07K 14/705* | (2006.01) |
| *A61K 40/11* | (2025.01) |
| *A61K 40/31* | (2025.01) |
| *A61K 40/42* | (2025.01) |
| *A61K 45/06* | (2006.01) |
| *A61P 35/00* | (2006.01) |
| *C07K 14/725* | (2006.01) |
| *C07K 19/00* | (2006.01) |
| *C12N 5/0783* | (2010.01) |

(52) U.S. Cl.
CPC .......... *C07K 14/7056* (2013.01); *A61K 40/11* (2025.01); *A61K 40/31* (2025.01); *A61K 40/4202* (2025.01); *A61K 40/4224* (2025.01); *A61K 45/06* (2013.01); *A61P 35/00* (2018.01); *C07K 14/7051* (2013.01); *C07K 14/70517* (2013.01); *C07K 14/70578* (2013.01); *C12N 5/0636* (2013.01); *A61K 2239/10* (2023.05); *A61K 2239/15* (2023.05); *A61K 2239/17* (2023.05); *A61K 2239/21* (2023.05); *A61K 2239/22* (2023.05); *A61K 2239/31* (2023.05); *A61K 2239/38* (2023.05); *A61K 2239/49* (2023.05); *C07K 2319/00* (2013.01); *C07K 2319/03* (2013.01); *C12N 2510/00* (2013.01)

(58) Field of Classification Search
CPC ............ C07K 14/70596; C07K 14/705; C07K 19/00; C07K 2319/00; C07K 2319/03; C07K 14/70517; C07K 14/70578; A61K 40/31; A61K 40/11; A61K 40/42; A61K 40/4202; A61K 40/4224; A61K 2239/49; A61K 2239/10; A61K 2239/11; A61K 2239/15; A61K 2239/17; A61K 2239/21; A61K 2239/22; C12N 5/0636; C12N 2510/00
See application file for complete search history.

(56) References Cited

U.S. PATENT DOCUMENTS

| | | | |
|---|---|---|---|
| 7,994,298 B2 | 8/2011 | Zhang | |
| 8,252,914 B2 | 8/2012 | Zhang | |
| 9,573,988 B2 * | 2/2017 | Brogdon ............ | A61K 40/4224 |
| 2013/0266551 A1 * | 10/2013 | Campana ........... | C07K 16/2896 |
| | | | 435/328 |
| 2014/0050708 A1 | 2/2014 | Powell | |
| 2014/0286973 A1 | 9/2014 | Powell, Jr. | |
| 2015/0225480 A1 | 8/2015 | Powell, Jr. | |
| 2016/0000828 A1 | 1/2016 | Campana | |
| 2020/0131244 A1 * | 4/2020 | Leong ................. | C12N 15/625 |

FOREIGN PATENT DOCUMENTS

WO       WO-2018165913 A1 *   9/2018

OTHER PUBLICATIONS

Song, De-Gang, et al. "CD27 Costimulation Augments the Survival and Antitumor Activity of Redirected Human T Cells in Vivo." Blood, vol. 119, No. 3, Jan. 19, 2012, pp. 696-706, https://doi.org/10.1182/blood-2011-03-344275. Accessed Feb. 13, 2021. (Year: 2012).*

(Continued)

*Primary Examiner* — Bridget E Bunner

(74) *Attorney, Agent, or Firm* — Saul Ewing LLP; Kathryn Doyle; Peter Brunovskis

(57) ABSTRACT

The invention includes a chimeric antigen receptor (CAR) specific for a natural-killer group 2, member D ligand (NKG2DL), compositions comprising the CAR, polynucleotides encoding the CAR, vectors comprising a polynucleotide encoding the CAR, and recombinant T cells comprising the CAR. The invention also includes methods of making a genetically modified T cell expressing a NKG2D-CAR wherein the expressed CAR comprises a NKG2D extracellular domain. The present invention also relates generally to the use of T cells engineered to express a CAR to treat cancer associated with NKG2D.

15 Claims, 21 Drawing Sheets
Specification includes a Sequence Listing.

(56)                    References Cited

OTHER PUBLICATIONS

Agaugue et al. The high expression of NKG2D ligands on tumor and the lack of surface expression on healthy tissues provides a strong rationale to support NKG2D-based therapeutic approaches for cancer. Immunother Cancer 29(Suppl 8): vii420, #1179P, Oct. 2018.*

Dhar et al. NKG2D and its ligands in cancer. Curr Opin Immunol 51: 55-61, 2018.*

WO 2018165913 English language translation (20 total pages).*

Barber et al. J Immunol 2008; 180:72-78.

Barber, A., et al., Chimeric NKG2D receptor-bearing T cells as immunotherapy for ovarian cancer. Cancer research, 2007. 67(10): p. 5003-5008.

Barber, A., et al., Chimeric NKG2D receptor-expressing T cells as an immunotherapy for multiple myeloma. Experimental hematology, 2008. 36(10): p. 1318-1328.

De Kruijf, E.M., et al., NKG2D ligand tumor expression and association with clinical outcome in early breast cancer patients: an observational study. Bmc Cancer, 2012. 12(1): p. 24.

International Search Report and Written Opinion issued Nov. 20, 2019 in International Application No. PCT/US2019/038739.

Kalos Michael et al, "T Cells with Chimeric Antigen Receptors Have Potent Antitumor Effects and Can Establish Memory in Patients with Advanced Leukemia", Aug. 10, 2011, (Aug. 10, 2011), vol. 3, No. 95, p. 95ra73.1, XP002667262.

Kershaw et al, Gene-engineered T cells for cancer therapy, Nature, 2013, pp. 525-541.

Kim et al., Journal of Immunotherapy. 2008; 31(5):475-486.

Lehner, M., et al., Redirecting T cells to Ewing's sarcoma family of tumors by a chimeric NKG2D receptor expressed by lentiviral transduction or mRNA transfection. PloS one, 2012. 7(2): p. e31210.

Lynn, R.C. and D.J. Powell, Strain-dependent lethal toxicity in NKG2D ligand-targeted CAR T-cell therapy. Molecular Therapy, 2015. 23(10): p. 1559-1561.

Nausch, N. and A. Cerwenka, NKG2D ligands in tumor immunity. Oncogene, 2008. 27(45): p. 5944-5958.

Nikiforow, S., et al., Safety Data from a First-in-Human Phase 1 Trial of NKG2D Chimeric Antigen Receptor-T Cells in AML/MDS and Multiple Myeloma. 2016, Am Soc Hematology.

Song D-G et al., Human gene therapy. 2013; 24(3):295-305.

Song, D.G., et al., "In vivo persistence, tumor localization, and antitumor activity of CAR-engineered T cells is enhanced by costimulatory signaling through CD137 (4-1BB)", Cancer Res 71, 4617-4627 (2011).

Song, et al., "CD27 costimulation augments the survival and antitumor activity of redirected human T cells in vivo.", Blood 119:, 696-706, 2012.

VanSeggelen, H., et al., T cells engineered with chimeric antigen receptors targeting NKG2D ligands display lethal toxicity in mice. Molecular Therapy, 2015. 23(10): p. 1600-1610.

Zhang et al. "Generation of Antitumor Responses by Genetic Modification of Primary Human T Cells with a Chimeric NKG2D Receptor" Cancer Research (2006) vol. 66, No. 11, pp. 5927-5933.

Zhang, T., B.A. Lemoi, and C.L. Sentman, Chimeric NK-receptor-bearing T cells mediate antitumor immunotherapy. Blood, 2005. 106(5): p. 1544-1551.

* cited by examiner

+IL-2

No IL-2

MDA-MB-231

NKG2DLs ⟶

AE17

NKG2DLs(NKG2D-Fc)⟶

Day14-21
T cell counts and CAR expression

CAR lentivirus

Day 0
activation
CD3/28 beads

Day1
transduction

Day 5
CAR expression
and Wash with PBS

CAR T cells

IL-2 500U/ML

No IL-2

COMPOSITIONS AND METHODS OF NKG2D CHIMERIC ANTIGEN RECEPTOR T CELLS FOR CONTROLLING TRIPLE-NEGATIVE BREAST CANCER

CROSS-REFERENCE TO RELATED APPLICATIONS

The present application is a 35 U.S.C. § 371 national phase application from, and claims priority to, International Application No. PCT/US2019/038739, filed Jun. 24, 2019, and published under PCT Article 21(2) in English, which claims priority under 35 U.S.C. § 119(e) to U.S. Provisional Patent Application No. 62/689,552, filed Jun. 25, 2018, all of which applications are incorporated herein by reference in their entireties.

BACKGROUND OF THE INVENTION

Triple negative breast cancer (TNBC), an aggressive form of breast cancer that lacks significant expression of the human epidermal growth factor receptor 2 (HER2), estrogen receptor (ER) and progesterone receptor (PR), accounts for approximately 15%-20% of invasive breast cancers. In the absence of obvious targets, patients with TNBC do not benefit from endocrine therapy or other available targeted agents. To date, the standard treatment still depends on surgery and adjuvant chemotherapy and radiotherapy. Patients with TNBC have a worse outcome after chemotherapy, compared to breast cancers patients with other subtypes, a finding that reflects the intrinsically adverse prognosis associated with the disease. Thus, effective therapeutic strategies are urgently needed for TNBC patients.

Cancer cells, including TNBC cells, frequently upregulate "stress" induced ligands recognized by the NK cell activating receptors NKG2D (natural-killer group 2, member D) and DNAM-1(CD226). The feasibility of targeting NKG2D ligands (NKG2DLs) utilizing a chimeric antigen receptor (CAR) engineered T cell approach was demonstrated by Sentman and colleagues in 2005, and early clinical trial results now show the significant promise of this approach (Sallman et al., 27 Apr. 2018: Haematologica, haematol. 2017.18674). This CAR construct contained the full-length NKG2D fused to the cytoplasmic domain of CD3z with costimulation provided endogenously by Dap10. However, there is no evidence in the art that this CAR is an effective targeted therapy for triple negative breast cancers (TNBC).

There is an urgent need in the art for achieving a more specific and effective treatment for triple negative breast cancer (TNBC). The present invention addresses this need.

SUMMARY OF THE INVENTION

As described herein, the present invention relates to compositions and methods utilizing NKG2D chimeric antigen receptor T cells for controlling cancer (e.g. triple-negative breast cancer).

One aspect of the invention includes a nucleic acid molecule encoding a chimeric antigen receptor (CAR). The nucleic acid molecule comprises a nucleic acid sequence encoding a natural-killer group 2, member D (NKG2D) extracellular domain, a nucleic acid sequence encoding a CD27 costimulatory domain, and a nucleic acid sequence encoding a CD3 zeta signaling domain.

Another aspect of the invention includes a chimeric antigen receptor (CAR) comprising a natural-killer group 2, member D (NKG2D) extracellular domain, a CD27 costimulatory domain, and a CD3 zeta signaling domain.

Yet another aspect of the invention includes a genetically modified T cell comprising any one of the CARs disclosed herein.

Another aspect of the invention includes a genetically modified T cell comprising a nucleic acid molecule encoding a chimeric antigen receptor (CAR), wherein the nucleic acid molecule comprises a nucleic acid sequence encoding a natural-killer group 2, member D (NKG2D) extracellular domain, a nucleic acid sequence encoding a CD27 costimulatory domain, and a nucleic acid sequence encoding a CD3 zeta signaling domain.

Still another aspect of the invention includes a genetically modified T cell comprising a nucleic acid molecule encoding a CAR, wherein the nucleic acid molecule comprises the nucleic acid sequence of SEQ ID NO: 14 or SEQ ID NO: 16 or SEQ ID NO: 18.

In another aspect, the invention includes a genetically modified T cell comprising a CAR, wherein the CAR comprises the amino acid sequence of SEQ ID NO: 15 or SEQ ID NO: 17 or SEQ ID NO: 19.

Still another aspect of the invention includes a vector comprising any one of the nucleic acid molecules disclosed herein.

Another aspect of the invention includes a vector comprising a nucleic acid molecule encoding a chimeric antigen receptor (CAR), wherein the nucleic acid molecule comprises a nucleic acid sequence encoding a natural-killer group 2, member D (NKG2D) extracellular domain, a nucleic acid sequence encoding a CD27 costimulatory domain, and a nucleic acid sequence encoding a CD3 zeta signaling domain.

Yet another aspect of the invention includes a method for treating cancer in a subject. The method comprises administering to the subject an effective amount of any one of the genetically modified T cells disclosed herein, thereby treating cancer in the subject.

Another aspect of the invention includes a method for treating cancer in a subject, the method comprising: administering to the subject an effective amount of a genetically modified T cell comprising a nucleic acid nucleic acid molecule encoding a chimeric antigen receptor (CAR), wherein the nucleic acid molecule comprises a nucleic acid sequence of a natural-killer group 2, member D (NKG2D) extracellular domain, a nucleic acid sequence encoding a CD27 costimulatory domain, and a nucleic acid sequence encoding a CD3 zeta signaling domain, thereby treating cancer in the subject.

In various embodiments of the above aspects or any other aspect of the invention delineated herein, the CAR further comprises a CD8 alpha hinge.

In another embodiment, the CAR further comprises a CD8 alpha transmembrane domain.

In another embodiment, the extracellular domain of NKG2D binds NKG2D ligand (NKG2DL).

In another embodiment, the nucleic acid molecule of the CAR comprises the nucleic acid sequence of SEQ ID NO: 14.

In another embodiment, the nucleic acid sequence encoding NKG2D extracellular domain comprises SEQ ID NO: 2.

In another embodiment, the nucleic acid sequence encoding the CD27 costimulatory domain comprises SEQ ID NO: 4.

In another embodiment, the CAR further comprises a CD8 alpha hinge.

In another embodiment, the CAR further comprises a CD8 alpha transmembrane domain.

In another embodiment, the CAR further comprises an extracellular domain of NKG2D that binds NKG2D ligand (NKG2DL).

In another embodiment, the CAR is encoded by the nucleic acid sequence of SEQ ID NO: 14.

In another embodiment, the NKG2D extracellular domain of the CAR comprises the amino acid sequence of SEQ ID NO: 3.

In another embodiment, the CD27 costimulatory domain comprises the amino acid sequence of SEQ ID NO: 5.

In another embodiment, the CAR comprises the amino acid sequence of SEQ ID NO: 15.

In another embodiment, the vector is a lentiviral vector.

In another embodiment, the vector is a RNA vector.

In another embodiment, the vector comprises the nucleic acid sequence of SEQ ID NO: 1.

In another embodiment, the cancer is selected from the group consisting of breast cancer, triple negative breast cancer (TNBC), ovarian cancer and colorectal cancer.

In another embodiment, the subject is a human.

In another embodiment, the subject is administered a secondary treatment. In another embodiment, the secondary treatment is selected from the group consisting of immune checkpoint blockade, chemotherapy, radiation, and surgery.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A: Schematic illustration of the lentiviral construct for the NKG2D CARs. NKG2D CAR sequences were preceded in-frame by a green fluorescent protein (GFP) sequence followed by the 2A ribosomal skipping sequence. NKG2D CAR contains the extracellular portion of the human NKG2D receptor, which linked to a CD8a hinge and transmembrane region, followed by a CD3z signaling moiety alone (GFP-NKG2D-z) or in tandem with the 4-1BB (GFP-NKG2D-BBz) or CD27(GFP-NKG2D-27z) intracellular signaling motif FIG. 2B: NKG2D CAR and GFP coexpressed by CD3+ T cells 14 days after transduction. UNT T cells only express endogenous NKG2D.

FIG. 3A: NKG2D CAR modified T cells secrete IFN-γ during overnight coculture with NKG2DLs-expressing TNBC cells, but not NKG2DLs-negative AE17 mesothelioma cells. Mean IFN-γ concentration±SD (pg/ml) from triplicate cultures is shown. FIG. 3B: Lysis of NKG2DLs expressing TNBC cells (MDA-MB-231 fluc) by NKG2D CAR T cells in an 18-hr bioluminescence assay at the indicated effector-to-target (E/T) ratios. Untransduced (UNT) CD3+ human T cells and AE17 mesothelioma cells served as negative effector and target cell controls, respectively. FIG. 3C: Normalized Cell Index (CI) plot for target cells (AE17, BT549, MDA-MB-436 and MDA-MB-468) incubated with UNT or NKG2D CAR T cells at different E:T ratios for 24 hours. When seeded alone, target cells adhere to the plate and proliferate, increasing the CI readout (black lines). When T cells added to target cells, NKG2CD CAR T cells cause cell cytolysis and subsequent progressive decrease in CI. Y-axis is the normalized CI generated by the RTCA software and displayed in real time. X-axis is the time of cell culture and treatment time in hour. Mean values of the CI were plotted±standard deviation. FIG. 3D: The Cell Index plot is converted to a % Lysis plot by the xCELLigence Immunotherapy Software.

FIG. 5A: One representative donor NKG2D CAR T cells expressed high level of CD25 and low level of CD25 by depleting human CD25 with magnetic separation on day 5 (4 days post transduction). FIG. 5B Percentages of $CD25^{high}$ and $CD25^{low}$ expressing GFP+ (NKG2D CAR) cells, presented as the mean±SD, were derived from three independent donors during a 3-week culture period in the presence of IL-2 (50 IU/ml). FIG. 5C The kinetic monitoring of $CD25^{high}$ and $CD25^{low}$ expressing GFP (NKG2D CAR) expression on one representative donor of three in the presence of IL-2.

FIG. 6A: NKG2D ligands expression on TNBC cell line MDA-MB-231 detected by NKG2D-Fc chimeric protein. FIG. 6B: Growth curve of MDA-MB-231 tumor (n=5) treated with the control PBS, UNT T cells ($3\times10^7$), or NKG2D CAR T cells ($3\times10^7$, ~30% CAR*) by intravenous injection 40 and 45 days post tumor inoculation. At the end of the experiment, the tumors treated with GFP-NKG2D-BBz or -27z CAR T cells were significantly smaller than those in the control group and GFP-NKG2D-z group (P<0.001). FIG. 6C: Bioluminescence images was applied to monitor and quantify MDA-MB-231 fLuc(+) tumor growth in NSG mice immediately before and 3 weeks after first CAR-T cells injection. FIG. 6D: CD4+ and CD8+ GFP-NKG2D-BBz and GFP-NKG2D-27z CAR T cells were initially present at low numbers in peripheral circulation, suggesting NKG2DLs-specific CAR T cell migration to specific tumor locales. Mean cell concentration (cells/ul)±SEM for all evaluable mice in each treatment group is shown (n=5). FIG. 6E: NKG2D-z CAR, but not costimulated NKG2D CAR, was poorly expressed on the surface of transduced (GFP+) T cells, suggesting CAR down-regulation. FIGS. 6F-6G: CD27 and 4-1BB signaling enhances the survival of circulating human CD4+ and CD8+ T cells in vivo 3 weeks after first dose of T-cell infusion (P<0.01) and costimulated NKG2D CAR expression on the T cell surface is stable and increased in vivo.

FIG. 7A: illustrates AE17, a mouse malignant mesothelioma cell line used as a negative control herein, did not express detectable human NKG2DLs. FIG. 7B: Schematic of the monitoring NKG2D CAR expression procedure in the presence or absence of IL-2. NKG2DLs are expressed on activated CD8$^+$ and CD8$^-$ (CD4)T cells after 4 days activation by anti-CD3/28 beads. FIG. 7C: Results for three independent donors are shown and irrelevant folate receptor-alpha (FRA)-Fc protein was used as negative control.

FIG. 8A: Expression of PD-1 and TIM-3 markers of exhaustion in T cells during culture. Anti-CD3/28 beads activated NKG2D-27z CAR T cells (15 hours stimulation) were used as positive control for expression of PD-1 and TIM-3. FIG. 8B: Expression of CD137 and PD-1 in T cells during culture and when co-cultured with MDA-MD-231 cells.

DETAILED DESCRIPTION

Figure 1:
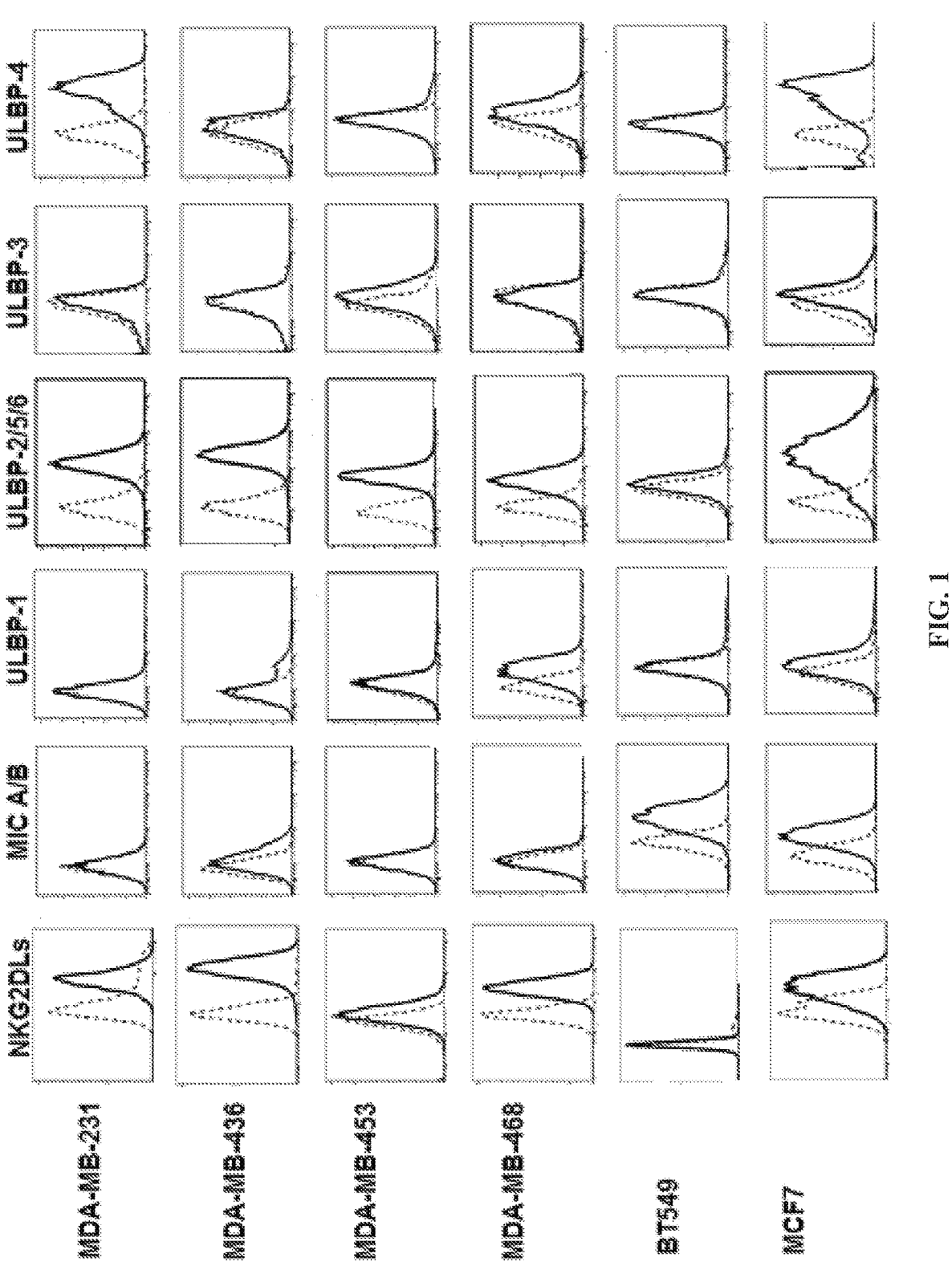
FIG. 1 is a series of histograms depicting the surface expression of NKG2D ligands on TNBC cells in a TNBC cell line. A panel of human TNBC cells were stained with recombinant NKG2D-Fc or specific antibodies that recognize MICA/B; ULBP-1, -2/5/6, -3, or -4 (solid line); matched isotype or irrelevant recombinant protein-Fc controls (dashed line) and analyzed by flow cytometry. A breast cancer cell line, MCF7, was used as a positive control.

The invention includes a chimeric antigen receptor (CAR) specific for a natural-killer group 2, member D ligands (NKG2DLs), compositions comprising the CAR, polynucleotides encoding the CAR, vectors comprising a polynucleotide encoding the CAR, and recombinant T cells comprising the CAR.

The invention also includes methods of making a genetically modified T cell expressing a NKG2D-CAR wherein the expressed CAR comprises a NKG2D extracellular domain.

The present invention also relates generally to the use of T cells engineered to express a CAR to treat cancer associated with NKG2D.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20% or ±10%, in some instances ±5%, in some instances ±1%, and in some instance ±0.1% from the specified value, as such variations are appropriate to perform the disclosed methods.

The term "antibody," as used herein, refers to an immunoglobulin molecule that binds with an antigen. Antibodies can be intact immunoglobulins derived from natural sources or from recombinant sources, and can be immunoreactive portions of intact immunoglobulins. Antibodies are typically tetramers of immunoglobulin molecules. The antibody may exist in a variety of forms where the antibody is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "high affinity" as used herein refers to high specificity in binding or interacting or attraction of one molecule to a target molecule.

The term "antigen" or "Ag" as used herein is defined as a molecule that provokes an immune response. This immune response may involve either antibody production, or the activation of specific immunologically competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

"Chimeric antigen receptor" or "CAR" refers to an engineered receptor that is expressed on a T cell or any other effector cell type capable of cell-mediated cytotoxicity. The CAR includes an antigen or fragment (e.g. extracellular domain) thereof that is specific for a ligand or receptor. The CAR optionally also includes a transmembrane domain, an intracellular domain and a signaling domain.

"Costimulatory ligand," as the term is used herein, includes a molecule on an antigen presenting cell (e.g., an aAPC, dendritic cell, B cell, and the like) that specifically binds a cognate costimulatory molecule on a T cell, thereby providing a "second" signal which, in addition to the primary signal provided by, for instance, binding of a TCR/CD3 complex with an MHC molecule loaded with peptide, mediates a T cell response, including, but not limited to, proliferation, activation, differentiation, and the like.

A "costimulatory molecule" refers to the cognate binding partner on a T cell that specifically binds with a costimulatory ligand, thereby mediating a costimulatory response by the T cell, such as, but not limited to, proliferation. Costimulatory molecules include, but are not limited to CD28, CD27, and OX40.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

The term "effector function" refers to a specialized function of a cell.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by a promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

"Intracellular domain" refers to a portion or region of a molecule that resides inside a cell.

The term "intracellular signaling domain" is meant to include any truncated portion of the intracellular domain sufficient to transduce the effector function signal.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase "nucleotide sequence" that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. In some embodiments, a nucleic acid sequence is considered to have at least 95%, 96%, 97%, 98%, or 99% identity or homology to any nucleic acid sequence disclosed herein.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. In some embodiments, an amino acid sequence is considered to have at 95%, 96%, 97%, 98%, or 99% identity or homology to any amino acid sequence described herein.

The term "proinflammatory cytokine" refers to a cytokine or factor that promotes inflammation or inflammatory responses. Examples of proinflammatory cytokines include, but are not limited to, chemokines (CCL, CXCL, CX3CL, XCL), interleukins (such as, IL-1, IL-2, IL-3, IL-5, IL-6, IL-7, IL-9, IL10 and IL-15), interferons (IFNγ), and tumor necrosis factors (TNFα and TNFβ).

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

"Signaling domain" refers to the portion or region of a molecule that recruits and interacts with specific proteins in response to an activating signal.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cells that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

"Transmembrane domain" refers to a portion or a region of a molecule that spans a lipid bilayer membrane.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Chimeric Antigen Receptor (CAR)

The present invention is partly based on the discovery of a chimeric antigen receptor (CAR) comprising an NKG2D extracellular domain, for treating cancer (e.g. TNBC). In certain embodiments the NKG2D CAR comprises a CD3 zeta signaling domain. In certain embodiments the NKG2D CAR comprises a 4-1BB costimulatory domain and a CD3 zeta signaling domain. In certain embodiments the NKG2D CAR comprises a CD27 costimulatory domain and a CD3 zeta signaling domain.

In one aspect, the invention includes a nucleic acid molecule encoding a chimeric antigen receptor (CAR), wherein the nucleic acid molecule comprises a nucleic acid sequence encoding an NKG2D extracellular domain, a nucleic acid sequence encoding a CD27 costimulatory domain, and a nucleic acid sequence encoding a CD3 zeta signaling domain.

In one embodiment, the NKG2D CAR is encoded by the nucleic acid sequence of SEQ ID NO: 14. In one embodiment, the NKG2D CAR is encoded by the nucleic acid sequence of SEQ ID NO: 16. In one embodiment, the NKG2D CAR is encoded by the nucleic acid sequence of SEQ ID NO: 18. In one embodiment, the NKG2D CAR comprises the amino acid sequence of SEQ ID NO: 15. In one embodiment, the NKG2D CAR comprises the amino acid sequence of SEQ ID NO: 17. In one embodiment, the NKG2D CAR comprises the amino acid sequence of SEQ ID NO: 19.

In some embodiments, the NKG2D CAR is encoded by a nucleic acid sequence having 85%, 86%, 87%, 88%, 89%, 90%, 91%, 92%, 93%, 94%, 95%, 96%, 97%, 98%, or 99% sequence identity to the nucleic acid sequence of any one of SEQ ID NOs: 14, 16, or 18. In some embodiments, the NKG2D CAR comprises an amino acid sequence having 85%, 86%, 87%, 88%, 89%, 90%, 91%, 92%, 93%, 94%, 95%, 96%, 97%, 98%, or 99% sequence identity to the amino acid sequence of any one of SEQ ID NOs: 15, 17, or 19.

Antigen Binding Moiety

In one embodiment, the CAR of the invention comprises an antigen binding domain or a fragment thereof.

In some instances, it is beneficial that the antigen binding domain is derived from the same species in which the CAR will ultimately be used. For example, for use in humans, it may be beneficial that the antigen binding domain of the CAR comprise a human antigen receptor that binds a human antigen or a fragment thereof.

In one exemplary embodiment, a genetically engineered chimeric antigen receptor includes an NKG2D extracellular domain which binds an NKG2DL in a mammal (e.g. human).

In some embodiments, the NKG2D extracellular domain is encoded by a nucleic acid sequence of SEQ ID NO: 2. In some embodiments, NKG2D extracellular domain is encoded by a nucleic acid sequence having 85%, 86%, 87%, 88%, 89%, 90%, 91%, 92%, 93%, 94%, 95%, 96%, 97%, 98%, or 99% sequence identity to the nucleic acid sequence of SEQ ID NO: 2. In other embodiments, the extracellular domain of NKG2D comprises the amino acid sequence of SEQ ID NO: 3. In yet other embodiments, the extracellular domain of NKG2D comprises an amino acid sequence having 85%, 86%, 87%, 88%, 89%, 90%, 91%, 92%, 93%, 94%, 95%, 96%, 97%, 98%, or 99% sequence identity to the amino acid sequence of SEQ ID NO: 3.

Transmembrane Domain

With respect to the transmembrane domain, in various embodiments, the NKG2D CAR comprises a transmembrane domain that is fused to the extracellular domain of the NKG2D CAR. In one embodiment, the NKG2D CAR comprises a transmembrane domain that naturally is associated with one of the domains in the NKG2D CAR. In some instances, the transmembrane domain is selected or modified by amino acid substitution to avoid binding to the transmembrane domains of the same or different surface membrane proteins in order to minimize interactions with other members of the receptor complex.

The transmembrane domain may be derived either from a natural or from a synthetic source. When the source is natural, the domain may be derived from any membrane-bound or transmembrane protein. In one embodiment, the transmembrane domain may be synthetic, in which case it will comprise predominantly hydrophobic residues such as leucine and valine. In one aspect a triplet of phenylalanine, tryptophan and valine will be found at each end of a synthetic transmembrane domain. Optionally, a short oligo- or polypeptide linker, between 2 and 10 amino acids in length may form the linkage between the transmembrane domain and the cytoplasmic signaling domain of the NKG2D CAR. A glycine-serine (GS) doublet provides a particularly suitable linker.

In some instances, a variety of human hinges can be employed as well including the human Ig (immunoglobulin) hinge.

Examples of the hinge and/or transmembrane domain include, but are not limited to, a hinge and/or transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIR, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In one embodiment, the NKG2D CAR comprises a transmembrane domain, such as, but not limited to, CD8 alpha transmembrane domain: IYIWAPLAGTCGVLLLSLVITLY (SEQ ID NO: 8) which is encoded by ATCTA-CATCTGGGCACCCTTGGCTGGAA-CATGCGGGGTCCTGCTGCTGAGCTT GGTGAT-CACCCTTTA (SEQ ID NO: 9).

In some embodiments, the CD8 alpha transmembrane domain comprises an amino acid sequence having 85%, 86%, 87%, 88%, 89%, 90%, 91%, 92%, 93%, 94%, 95%, 96%, 97%, 98%, or 99% sequence identity to the amino acid sequence of SEQ ID NO: 8. In further embodiments, the CD8 alpha transmembrane domain is encoded by a nucleic acid sequence having 85%, 86%, 87%, 88%, 89%, 90%, 91%, 92%, 93%, 94%, 95%, 96%, 97%, 98%, or 99% sequence identity to the nucleic acid sequence of SEQ ID NO: 9.

In another embodiment, the NKG2D CAR comprises a GS linker SGGGGSGGGGSSG (SEQ ID NO:10) which is encoded by AGCGGAGGTGGAGGTAGTGGCGGTG-GAGGCAGCTCTGGT (SEQ ID NO:11).

Intracellular Domain of a Costimulatory Molecule

The intracellular domain of a costimulatory molecule of the NKG2D CAR of the invention is a cytoplasmic domain responsible for the activation of at least one of the normal effector functions of the immune cell in which the NKG2D CAR has been placed in.

Effector function of a T cell, for example, may be cytolytic activity or helper activity including the secretion of cytokines. Thus the term "intracellular domain of a costimulatory molecule" refers to the portion of a protein which transduces the effector function signal and directs the cell to perform a specialized function." While the entire intracellular domain of a costimulatory molecule can be employed, in many cases it is not necessary to use the entire domain. To the extent that a truncated portion of the intracellular domain of a costimulatory molecule is used, such truncated portion may be used in place of the intact domain as long as it transduces the effector function signal.

The intracellular domain of a costimulatory molecule refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, CDS, ICAM-1, GITR, BAFFR, HVEM (LIGHTR), SLAMF7, NKp80 (KLRF1), CD127, CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof. In one embodiment, the NKG2D CAR of the invention comprises a CD27 co-stimulatory domain.

In one embodiment, the nucleic acid sequence encoding the CD27 costimulatory domain comprises SEQ ID NO: 4. In still another embodiment, the amino acid sequence of the CD27 costimulatory domain comprises: QRRKYRSNKGESPVEPAEPCRYSCPR EEEGSTIP-IQEDYRKPEPACSP (SEQ ID NO: 5).

In some embodiments, the CD27 costimulatory domain comprises an amino acid sequence having 85%, 86%, 87%, 88%, 89%, 90%, 91%, 92%, 93%, 94%, 95%, 96%, 97%, 98%, or 99% sequence identity to the amino acid sequence s of SEQ ID NO: 5. In other embodiments, the CD27 costimulatory domain is encoded by a nucleic acid sequence having 85%, 86%, 87%, 88%, 89%, 90%, 91%, 92%, 93%, 94%, 95%, 96%, 97%, 98%, or 99% sequence identity to the nucleic acid sequence of SEQ ID NO: 4.

The human intracellular CD27 costimulatory domain provides co-stimulatory intracellular signaling upon binding to the extracellular autoantigen, such as NKG2D, or a fragment thereof, without the need of its original ligand.

Signaling Domain

Primary cytoplasmic signaling sequences regulate primary activation of the TCR complex either in a stimulatory manner or in an inhibitory manner. Primary cytoplasmic signaling sequences that act in a stimulatory manner may contain signaling motifs which are known as immunoreceptor tyrosine-based activation motifs or ITAMs.

Examples of ITAM containing primary signaling sequences that are of particular use in the invention include those derived from TCR zeta, FcR gamma, FcR beta, CD3 gamma, CD3 delta, CD3 epsilon, CD5, CD22, CD79a, CD79b, and CD66d. In certain embodiments, the signaling molecule comprises a signaling domain derived from CD3 zeta.

In one embodiment, the signaling domain of the CAR can be designed to comprise the CD3 zeta signaling domain by itself or combined with any other desired cytoplasmic domain(s) useful in the context of the CAR of the invention. For example, the signaling domain of the CAR can comprise a CD3 zeta chain portion and a costimulatory signaling domain.

In some embodiments, the NKG2D CAR comprises a CD3 zeta signaling domain by itself or in combination with any other desired cytoplasmic domain(s) useful in the context of the NKG2D CAR of the invention. For example, the NKG2D CAR can comprise a CD3 zeta chain portion and an intracellular domain of a costimulatory molecule. In some embodiments, the CD3 zeta chain portion is a human T-cell surface glycoprotein CD3 zeta chain isoform 3 intracellular domain (human CD247). The human intracellular CD3 zeta domain provides stimulatory intracellular signaling upon binding to the extracellular domain of NKG2D or a fragment thereof, without HLA restriction.

In one embodiment, the nucleic acid sequence of the signaling domain comprises a nucleic acid sequence encoding a CD3 zeta signaling domain. In another embodiment, the nucleic acid sequence of the CD3 zeta signaling domain encodes an amino acid sequence comprising: RVKFSRS-ADAPAYKQGQNQLYNELNLGRREEYDVLDKRR-GRDPEMGGKPRRK NPQEGLYNELQKDKMAEAYSEI-GMKGERRRGKGHDGLYQGLSTATKDTYDAL HMQALPPR (SEQ ID NO: 12). In another embodiment, the nucleic acid sequence encoding the CD3 zeta signaling domain comprises: AGAGTGAAGTTCAGCAG-GAGCGCAGACGCCCCCGCGTACAAGCAGGGCCAG AACCAGCTCTATAACGAGCT-CAATCTAGGACGAAGAGAGGAGTACGATGTTT TGGACAAGAGACGTGGCCGGGACCCT-GAGATGGGGGGAAAGCCGAGAAGGA AGAACCCTCAGGAAGGCCTGTACAAT-GAACTGCAGAAAGATAAGATGGCGG AGGCCTA-CAGTGAGATTGGGATGAAAGGCGAGCGCCG-GAGGGGCAAGGGGC ACGATGGCCTTTACCAGGGTCTCAGTACAGCCAC-CAAGGACACCTACGACGC CCTTCA-CATGCAGGCCCTGCCCCCTCGC (SEQ ID NO: 13). In another embodiment, the nucleic acid sequence encoding the CD3 zeta signaling domain comprises:

```
                                    (SEQ ID NO: 20)
agagtgaagttcagcaggagcgcagacgcccccgcgtaccagcagggcc agaaccagctctataacgagctcaatctaggacgaagagaggagtacga tgttttggacaagagacgtggccgggaccctgagatgggggggaaagccg agaaggaagaaccctcaggaaggcctgtacaatgaactgcagaaagata agatggcggaggcctacagtgagattgggatgaaaggcgagcgccggag gggcaaggggcacgatggcctttaccagggtctcagtacagccaccaag gacacctacgacgcccttcacatgcaggccctgccccctcgc
```

In some embodiments, the CD3 zeta signaling domain comprises an amino acid sequence having 85%, 86%, 87%, 88%, 89%, 90%, 91%, 92%, 93%, 94%, 95%, 96%, 97%, 98%, or 99% sequence identity to the amino acid sequence of SEQ ID NO: 12. In other embodiments, the CD3 zeta signaling domain is encoded by a nucleic acid sequence having 85%, 86%, 87%, 88%, 89%, 90%, 91%, 92%, 93%, 94%, 95%, 96%, 97%, 98%, or 99% sequence identity to the nucleic acid sequence of SEQ ID NO: 13 or SEQ ID NO: 20.

Other Domains

In some embodiments, the NKG2D CAR and the nucleic acid molecule encoding the NKG2D CAR comprise a human T cell surface glycoprotein CD8 alpha chain signal peptide. The human CD8 alpha signal peptide is responsible for the translocation of the receptor to the T cell surface.

In other embodiments, the NKG2D CAR and the nucleic acid molecule encoding the NKG2D CAR comprise an IgG signal peptide. In some embodiments, the IgG signal peptide is encoded by a nucleic acid sequence comprising: In one embodiment, the polynucleotide encoding the NKG2D CAR comprises a nucleic acid sequence of a peptide linker. In another embodiment, the NKG2D CAR comprises a peptide linker. In yet another embodiment, the cytoplasmic signaling sequences within the intracellular signaling domain of the NKG2D CAR can be linked to each other in a random or specified order. Optionally, a short oligo- or polypeptide linker, for example, between 2 and 10 amino acids in length may form the linkage. A glycine-serine (GS) doublet is a particularly suitable linker.

Vector Comprising the NKG2D CAR

In one aspect, the invention includes a vector comprising a nucleic acid molecule encoding a chimeric antigen receptor (CAR), wherein the polynucleotide comprises an extracellular domain comprising a human NKG2D or fragment thereof, a transmembrane domain, and an intracellular signaling domain. In one embodiment, the vector comprises any of the nucleic acid sequences encoding the CAR as described herein. In another embodiment, the vector comprises a plasmid vector, viral vector, retrotransposon (e.g. piggyback, sleeping beauty), site directed insertion vector (e.g. CRISPR, Zinc finger nucleases, TALEN), or suicide expression vector, or other known vector in the art.

All constructs disclosed herein can be used with lentiviral vector plasmids, other viral vectors, or RNA approved for use in human cells. In one embodiment, the vector is a viral vector, such as a lentiviral vector. In another embodiment, the vector is a RNA vector.

The expression of the NKG2D CAR can be verified by sequencing. Expression of the full length CAR protein may be verified using immunoblot, immuno-histochemistry, flow cytometry, or other technology well known and available in the art.

The present invention also provides a vector in which a nucleic acid molecule encoding the CAR of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

In brief summary, the expression of natural or synthetic nucleic acid molecule encoding CARs is typically achieved by operably linking a nucleic acid encoding the CAR polypeptide or portions thereof to a promoter (e.g. EF1alpha promoter), and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid molecule can be cloned into any number of different types of vectors. For example, the nucleic acid molecule can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-ia promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence, which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Biological methods for introducing a polynucleotide of interest into a host cell include the use of DNA and RNA vectors. RNA vectors include vectors having a RNA promoter and/other relevant domains for production of a RNA transcript. Viral vectors, and especially retroviral vectors, have become the most widely used method for inserting genes into mammalian, e.g. human, cells. Other viral vectors may be derived from lentivirus, poxviruses, herpes simplex virus, adenoviruses, and adeno-associated viruses, and the like. See, for example, U.S. Pat. Nos. 5,350,674 and 5,585, 362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances, which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Any domains and/or fragments of the CAR, vector, and the promoter may be synthesized gene fragments amplified by PCR or any other means known in the art.

A self-inactivating lentiviral vector plasmid can be used in which the expression of the CAR is regulated by the human elongation factor 1 alpha promoter. This results in stable (permanent) expression of the CAR in the host T cell. As an alternative approach, the encoding mRNA can be electroporated into the host cell, which would achieve the same therapeutic effect as the virally transduced T cells, but would not be permanent because the mRNA would dilute out with cell division.

Provided in the invention is a vector comprising a nucleic acid molecule encoding a chimeric antigen receptor (CAR), wherein the nucleic acid molecule comprises a nucleic acid sequence encoding a natural-killer group 2, member D (NKG2D) extracellular domain, a nucleic acid sequence encoding a CD27 costimulatory domain, and a nucleic acid sequence encoding a CD3 zeta signaling domain.

In certain embodiments, the vector is a lentiviral vector. In certain embodiments, the vector is a RNA vector.

In certain embodiments, the vector comprises the nucleic acid sequence of SEQ ID NO: 1.

Cells Comprising the CAR

In another aspect, the invention includes a genetically modified cell comprising the NKG2D chimeric antigen receptor (CAR) disclosed herein.

In another embodiment, the genetically modified cell expresses the NKG2D CAR. In this embodiment, the cell has high affinity for cells expressing NKG2D ligands.

In one embodiment, the genetically modified cell is a T cell, such as a helper T cell, a cytotoxic T cell, a memory T cell, regulatory T cell, gamma delta T cell, a natural killer cell, cytokine induced killer cell, a cell line thereof, a T memory stem cell, or other T effector cell. It is also useful for the T cell to have limited toxicity toward healthy cells and specificity to cells expressing NKG2DLs. Such specificity prevents or reduces off-target toxicity that is prevalent in current therapies that are not specific. In one embodiment, the T cell has limited toxicity toward healthy cells. In one embodiment the T cell is an autologous cell. In another embodiment, the T cell is an allogeneic cell.

In some embodiments, the invention include genetically modified immune cells derived from pluripotent stem cells that were differentiated in vitro. In other embodiments, the invention includes T cells, such as primary cells, expanded T cells derived from primary T cells, T cells derived from stem cells differentiated in vitro, T cell lines such as Jurkat cells, other sources of T cells, combinations thereof, and other effector cells.

The proper processing of the antigen on the cell surface is also important and can be measured using monoclonal antibodies. Furthermore, truncations or mutations of NKG2D based on major disease epitopes are also useful and included herein. Truncated versions using a different length hinge region are also useful. With regard to safety, preventing or reducing possible homophilic and heterophilic interactions and activation (e.g. NKG2D-NKG2D) between the transduced cells or toward podocytes is preferred.

Further assessment of efficacy and safety of the CAR can be performed, for example, as follows:

Constructs can be transiently transfected into human cells, such as 293T/17. The surface expression can be detected with monoclonal antibodies (either IgG or ScFv) specific for the abovementioned extracellular domains (Ig1, Ig2, Ig3, Fz (Ig-like domains and frizzled domain)) the linker between the domains, or other structure included in the CAR. Binding can be verified with specific secondary antibodies and quantified by flow cytometry.

Production of membrane expressed constructs of human anti-NKG2D antibodies of any isotype can serve as target cells for testing the different NKG2D-CARs. Additional target cell lines can be produced as needed by expression of human monoclonal antibodies on the surface of cell lines (e.g. Nalm6 or K562 cells).

Provided in the invention is a genetically modified T cell comprising a nucleic acid molecule encoding a chimeric antigen receptor (CAR), wherein the nucleic acid molecule comprises a nucleic acid sequence encoding a natural-killer group 2, member D (NKG2D) extracellular domain, a nucleic acid sequence encoding a CD27 costimulatory domain, and a nucleic acid sequence encoding a CD3 zeta signaling domain.

Also provided in the invention is a genetically modified T cell comprising a nucleic acid molecule encoding a CAR, wherein the nucleic acid molecule comprises the nucleic acid sequence of SEQ ID NO: 14 or SEQ ID NO: 16 or SEQ ID NO: 18.

Additional provided in the invention is a genetically modified T cell comprising a chimeric antigen receptor (CAR), wherein the CAR comprises the nucleic acid sequence of SEQ ID NO: 15 or SEQ ID NO: 17 or SEQ ID NO: 19.

Diseases

The present invention also provides methods for preventing, treating and/or managing a cancer. The methods comprise administering to a subject in need thereof a genetically modified T cell comprising the CAR of the invention that binds to the NKG2D ligands. In one aspect, the subject is a human. Non-limiting examples of an NKG2D related cancer include but are not limited to breast cancer, triple negative breast cancer (TNBC), ovarian cancer and colorectal cancer The cells of the invention to be administered may be autologous, allogeneic or xenogeneic with respect to the subject undergoing therapy. In the methods of treatment, T cells isolated from a subject can be modified to express the appropriate CAR, expanded ex vivo and then reinfused into the same subject (e.g., the T cells are autologous T cells). In some embodiments the T cells are reinfused into a different subject than the original T cells' donor (e.g., the T cells are allogeneic T cells). The modified T cells recognize target cells, such as cells expressing NKG2DLs, and become activated, resulting in killing of the target cells.

Relapse may also occur in patients with a cancer, for example TNBC patients. In patients treated with drugs, the relapse may be mediated by persistence of the same clones, whereas remission is associated with disappearance of these clones.

To monitor NKG2D CAR-expressing cells in vitro, in situ, or in vivo, NKG2D CAR cells can further express a detectable marker. When the NKG2D CAR binds the target, the detectable marker is activated and expressed, which can be detected by assays known in the art, such as flow cytometry. In one embodiment, the NKG2D CAR includes a NFAT response element and a detectable marker, such as a green fluorescent protein (GFP), to detect and quantify NKG2D CAR expressing cells.

Sources of T Cells

Prior to expansion and genetic modification, T cells (e.g., autologous or allogeneic T cells) are obtained from a subject. Examples of subjects include humans, dogs, cats, mice, rats, and transgenic species thereof. T cells can be obtained from a number of sources, including skin, peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11 b, CD16, HLA-DR, and CD8. In certain embodiments, it may be desirable to enrich for or positively select for regulatory T cells which typically express $CD4^+$, $CD25^+$, $CD62L^+$, $GITR^+$, and $FoxP3^+$. Alternatively, in certain embodiments, T regulatory cells are depleted by anti-CD25 conjugated beads or other similar method of selection. In other embodiments, subpopulation of T cells, such as, but not limited to, cells positive or expressing high levels of one or more surface markers e.g. $CD28^+$, $CD8^+$, $CCR7^+$, $CD27^+$, $CD127^+$, $CD45RA^+$, and/or $CD45RO^+$ T cells, can be isolated by positive or negative selection techniques.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to –80° C. at a rate of 1° per minute and stored in the vapor phase of a liquid nitrogen storage tank. Other methods of controlled freezing may be used as well as uncontrolled freezing immediately at –20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as, but not limited to, rituximab or other anti-CD20 or anti-CD19 agents, anti-FcRn agents, Btk inhibitors, plasmapheresis, corticosteroids, mycophenolate, azathioprine, methotrexate, cyclosporine, cyclophosphamide. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before or simultaneous ablative therapy such as fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD8^+$ T cell expansion and T cell growth is used. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/ CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of $CD8^+$ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, $CD4^+$) that is greater than the cytotoxic or suppressor T cell population ($T_C$, $CD8^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_C$ cells or $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In one aspect, the invention includes a method for treating cancer in a subject, the method comprising: administering to the subject an effective amount of a genetically modified T cell comprising a nucleic acid nucleic acid molecule encoding a chimeric antigen receptor (CAR), wherein the nucleic acid molecule comprises a nucleic acid sequence of a encoding a natural-killer group 2, member D (NKG2D) extracellular domain, a nucleic acid sequence encoding CD27 costimulatory domain, and the nucleic acid sequence encoding CD3 zeta signaling domain, thereby treating cancer in the subject.

In another aspect, the invention includes a method for preventing or reducing cancer progression in a subject. The method comprises: administering to the subject an effective amount of a genetically modified T cell a nucleic acid nucleic acid molecule encoding a chimeric antigen receptor (CAR), wherein the nucleic acid molecule comprises a nucleic acid sequence of a encoding a natural-killer group 2, member D (NKG2D) extracellular domain, a nucleic acid sequence encoding CD27 costimulatory domain, and the nucleic acid sequence encoding CD3 zeta signaling domain, thereby preventing or reducing cancer progression in the subject.

In one embodiment, the cancer is selected from the group consisting of breast cancer, triple negative breast cancer (TNBC), ovarian cancer and colorectal cancer. In another embodiment, the subject is a human.

Without wishing to be bound by any particular theory, the immune response elicited by the CAR-modified T cells may be an active or a passive immune response. In one embodiment, the genetically modified T cells of the invention are modified by a fully-human CAR. In one embodiment, the fully-human CAR-genetically modified T cells may be a type of vaccine for ex vivo immunization and/or in vivo therapy in a mammal. In one embodiment, the mammal is a human.

With respect to ex vivo immunization, at least one of the following occurs in vitro prior to administering the cell into a mammal: i) expansion of the cells, ii) introducing to the cells a nucleic acid molecule encoding a CAR iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also includes compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the NKG2D CAR-modified T cells of the invention are used in the treatment of cancer. In certain embodiments, the cells of the invention are used in the treatment of patients at risk for developing a cancer. Thus, the present invention provides methods for the treatment or prevention of NKG2D related cancers comprising administering to a subject in need thereof, a therapeutically effective amount of the NKG2D CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The CAR T cells of the present invention may be administered in combination with a secondary treatment (e.g. immune checkpoint blockade, chemotherapy, radiation, and surgery.)

When "an immunologically effective amount," or "a therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, activated T cells are administered to a subject. Subsequent to administration, blood is redrawn or apheresis is performed, and T cells are activated and expanded therefrom using the methods described here, and are then reinfused back into the patient. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The cells of the invention to be administered may be autologous, allogeneic or xenogeneic with respect to the subject undergoing therapy.

Administration of the cells of the invention may be carried out using any convenient means, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir, interleukin-2, Cytarabine (also known as ARA-C), rituximab (or any other generalized B cell depleting agent such as Btk inhibitors or other anti-CD20/CD19 or B cell targeting agents) and/or Soliris® (eculizumab, a terminal complement inhibitor). In further embodiments, the T cells of the invention may be used in combination with an antibody anti-FcRn, IVIg, or plasmapheresis in order to reduce the anti-NKG2D antibody concentration before therapy. In yet other embodiments, a mild lymphodepletion regimen (e.g. Low-dose fludarabine or Cytoxan) might precede treatment with the T cells of the invention.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances smaller or larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

Cell lines: Human cell lines used in immune based assays include the established human breast cancer cell line MCF7, TNBC cell lines MDA-MB-231, MDA-MB-436, MDA-MB-468, MDA-MB-453 and BT549. The mouse malignant mesothelioma cell line, AE17 was used as antigen negative control. For bioluminescence assays, the cancer cell lines were transfected to express firefly luciferase (fLuc). Lentivirus packaging was executed using the immortalized normal fetal renal 293T cell line purchased from ATCC. All cell lines were maintained in complete medium: RPMI-1640 supplemented with 10% heat inactivated FBS, 100 U/mL penicillin, 100 mg/mL streptomycin sulfate.

CAR construction and lentivirus production: The NKG2D CAR construct comprises the extracellular portion of human NKG2D (aa 82-216) linked to a CD8a hinge and transmembrane region, followed by a CD3z signaling moiety alone (NKG2D-z) or in tandem with the 4-1BB or CD27 intracellular signaling motif, which was previously described (Song D-G et al., Blood. 2012; 119(3):696-706; Song D-G et al., Cancer research. 2011; 71(13):4617-4627). CAR sequences were preceded in frame by a green fluorescent protein (GFP) sequence followed by the 2A ribosomal skipping sequence.

High-titer replication-defective lentivirus were produced and concentrated as previously described (Parry et al., The Journal of Immunology. 2003; 171(1):166-174). Briefly, 293T cells were seeded in 150 cm$^2$ flasks and transfected using TurboFect (Life Technologies) according to manufacturer's instructions. NKG2D CAR transgene plasmid (15 ug) was co-transfected with 18 ug pRSV.REV (Rev expression plasmid), 18 ug pMDLg/p.RRE (Gag/Pol expression plasmid) and 7 ug pVSV-G (VSV glycoprotein expression plasmid) with 174 ul transfection reagent Express In (1 ug/ul) per flask. Supernatants were collected at 24 h and 48 h after transfection, concentrated 10-fold by ultracentrifugation for 2 hours at 28,000 rpm with a Beckman SW32Ti rotor (Beckman Coulter). The viruses were aliquoted and stored at −80° C. until ready to use for titering or experiments. All lentiviruses used in the experiments were from concentrated stocks.

Human T cells and transfection: Primary human T cells were isolated from healthy, normal donors following leukapheresis by negative selection. All T cell samples were collected from healthy, normal donors. T cells were cultured in R10 medium and stimulated with anti-CD3 and anti-CD28 monoclonal antibodies (mAb)-coated beads (Invitrogen). Approximately 18 to 24 hours after activation, human T cells were transduced. Briefly, 0.5×10$^6$ T cells were infected with a multiplicity of infection (MOI) 2 of the NKG2D receptor lentiviral vector and expanded for two weeks. Human recombinant interleukin-2 (IL-2; Novartis) was added every 2-3 days to a 50 IU/mL final concentration and a cell density of 0.5×10$^6$ to 1×10$^6$ cells/ml was maintained. Engineered CAR T cells were rested in cytokine-free medium for 24 hours, and were then used for functional analysis.

Flow cytometric analysis: The following fluorochrome-conjugated monoclonal antibodies, purchased from BD Biosciences, were used for T cells phenotypic analysis: APC-Cy7 anti-human CD3; FITC anti-human CD4; APC anti-human CD8; PE anti-human CD45, APC anti-human NKG2D. PE-anti-human CD137, APC anti-human PD-1 and Pacific Blue anti-human TIM-3 were purchased from Biolegend. 7-Aminoactinomycin D (7-AAD) was used for viability staining. Expression of NKG2D CAR was detected by GFP and surface NKG2D expression using anti-NKG2D Ab. For the in vivo experiments, peripheral blood was obtained via retro-orbital bleeding and stained for the presence of human CD45, CD4, and CD8 T cells. Gating specifically on the human CD45+ population, the CD4+ and CD8+ subsets were quantified using TruCount tubes (BD Biosciences) with known numbers of fluorescent beads as described in the manufacturer's instructions.

NKG2DLs were analyzed using PE anti-MICA/B (clone 6D4, BD Pharmingen), PE anti-ULBP1 (clone 170818, R&D System), PE anti-ULBP2/5/6 (clone 165903, R&D System), anti-ULBP3 (clone 2F9, Santa Cruz), and polyclonal Per-CP-anti-human ULBP4 (R&D System). Recombinant human NKG2D Fc chimera and a control recombinant human folate receptor-alpha (FRA) Fc chimera were purchased from R&D System. Matched secondary and isotype antibodies were used in all analyses. Flow cytometry was performed on BD FACSCanto II flow cytometer and flow cytometric data were analyzed using FlowJo Version 7.2.5 software.

Cytokine release assays: Cytokine release assays were performed by co-culturing 1×10$^5$ T cells with 1×10$^5$ target cells in triplicate in a 96-well flat bottom plate in a total volume of 200 ul R10 media. After 20-24 hours, cell free co-culture supernatants were collected and ELISA (Biolegend, San Diego) was performed, according to manufacturer's instructions, to measure the secretion of IFN-γ. The values shown represent the mean of triplicate wells.

Cytotoxicity assays: For cell-based bioluminescence assays, 5×10$^4$ firefly Luciferase (fLuc)-expressing tumor cells were cultured with R10 media in the presence of different T cell ratios in a 96-well Microplate (BD Biosciences). After incubation for ~20 hours at 37° C., each well was filled with 50 uL of D-luciferin (0.015 g/mL) resuspended with PBS and imaged with the Xenogen IVIS Spectrum. Tumor cell viability percentage was calculated as the mean luminescence of the experimental sample minus background divided by the mean luminescence of the input number of target cells used in the assay minus background times 100. All data are represented as a mean of triplicate wells.

Additional cytotoxicity of NKG2D CAR-T cells was measured in real time using an xCELLigence (ACEA Bioscience) label-free, impedance-based cell sensing device. AE17, MDA-MB-436, MDA-MB-468 or BT549 cells ($2 \times 10^4$/well) were left to adhere for 24 hours to xCELLigence E-plates. Cell proliferation was measured as a change in relative impedance, termed cell index (CI). After 24 h, the effector cells were added at the ratio of effector to target cell (E:T=2:1, 1:1, and 1:2) in a total volume of 200 μL. The cytotoxicity was then monitored by measuring changes in impedance as CI values recorded by the xCELLigence RTCA SP device.

Xenograft model of TNBC: NOD/SCID/γ-chain–/– (NSG) mice were bred, treated and maintained under pathogen-free conditions. All animals were obtained from the Stem Cell and Xenograft Core (SCXC) of the Abramson Cancer Center, University of Pennsylvania. To establish a TNBC model, 6~10 weeks old female NSG mice were inoculated subcutaneously (s.c.) on the flank with $3 \times 10^6$ MDA-MB-231 fluc(+) cells on day 0. After the tumors become palpable at about 3 weeks, primary human T cells were activated and transduced. After the primary human T cells were expanded for 2 weeks and the mouse tumor burden was about 200~300 mm$^3$, the mice were treated with the T cells. To investigate the roles of CD27 and 4-1BB costimulated NKG2D CAR in vivo, NKG2D CAR T cells were adjusted from 90% to ~30% by adding UNT T cells. The route, dose, and timing of T-cell injections are indicated in the individual figure legends. Tumor dimensions were measured with calipers, and tumor volumes calculated using the formula V=½(length×width$^2$), where length is greatest longitudinal diameter and width is greatest transverse diameter. Animals were imaged prior to T-cell transfer and three weeks thereafter to evaluate tumor growth. Photon emission from fluc+ cells was quantified using the "Living Image" software (Xenogen) for all in vivo experiments. Approximately 50 days after the first T-cell injection, the mice were euthanized and the tumors were resected immediately.

Bioluminescence imaging: Tumor growth was also monitored using Bioluminescent imaging (BLI). BLI was conducted using Xenogen IVIS imaging system. The photons emitted from fLuc-expressing cells within the animal body were quantified using Living Image software (Xenogen). Briefly, mice bearing MDA-MB-231fLuc tumors were injected intraperitoneally (i.p.) with D-luciferin (150 mg/kg stock, 100 μL of D-luciferin per 10 grams of mouse body weight) suspended in PBS and imaged under isoflurane anesthesia after 5~10 minutes. A pseudocolor image representing light intensity (blue, least intense; red, most intense) was generated using Living Image. BLI findings were confirmed at necropsy.

Statistical analysis: The data are reported as means and standard deviations (SD). Statistical analysis was performed using 2-way repeated-measures Analysis of Variance (ANOVA) for the tumor burden (tumor volume, photon counts). Student t test was used to evaluate differences in absolute numbers of transferred T cells, cytokine secretion, and specific cytolysis. GraphPad Prism 5.0 (GraphPad Software) was used for the statistical calculations, where a p-value of $P<0.05$ was considered significant.

Three CAR Constructs Used in the Invention:

```
(1) CAR vector: PELNS_eGFP_2A NKG2D_CD27_CD3Zeta nucleic acid sequence
                                                        (SEQ ID NO: 1)
ATGGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGCG

AGGGCGATGCCACCTACGGCAAGCTGACCCTGAAGTTCATCTGCACCACCGG

CAAGCTGCCCGTGCCCTGGCCCACCCTCGTGACCACCCTGACCTACGGCGTG

CAGTGCTTCAGCCGCTACCCCGACCACATGAAGCAGCACGACTTCTTCAAGT

CCGCCATGCCCGAAGGCTACGTCCAGGAGCGCACCATCTTCTTCAAGGACGA

CGGCAACTACAAGACCCGCGCCGAGGTGAAGTTCGAGGGCGACACCCTGGT

GAACCGCATCGAGCTGAAGGGCATCGACTTCAAGGAGGACGGCAACATCCT

GGGGCACAAGCTGGAGTACAACTACAACAGCCACAACGTCTATATCATGGCC

GACAAGCAGAAGAACGGCATCAAGGTGAACTTCAAGATCCGCCACAACATC

GAGGACGGCAGCGTGCAGCTCGCCGACCACTACCAGCAGAACACCCCCATCG

GCGACGGCCCCGTGCTGCTGCCCGACAACCACTACCTGAGCACCCAGTCCGC

CCTGAGCAAAGACCCCAACGAGAAGCGCGATCACATGGTCCTGCTGGAGTTC

GTGACCGCCGCCGGGATCACTCTCGGCATGGACGAGCTGTACAAGAGATCTG

GCGGCGGAGAGGGCAGAGGAAGTCTTCTAACATGCGGTGACGTGGAGGAGA

ATCCCGGCCCTAGATGGCCTTACCAGTGACCGCCTTGCTCCTGCCGCTGGCCT

TGCTGCTCCACGCCGCCAGGCCGGGATCCTTCAACCAAGAAGTTCAAATTCC

CTTGACCGAAAGTTACTGTGGCCCATGTCCTAAAAACTGGATATGTTACAAA

AATAACTGCTACCAATTTTTTGATGAGAGTAAAAACTGGTATGAGAGCCAGG
```

-continued

CTTCTTGTATGTCTCAAAATGCCAGCCTTCTGAAAGTATACAGCAAAGAGGA

CCAGGATTTACTTAAACTGGTGAAGTCATATCATTGGATGGGACTAGTACAC

ATTCCAACAAATGGATCTTGGCAGTGGGAAGATGGCTCCATTCTCTCACCCA

ACCTACTAACAATAATTGAAATGCAGAAGGGAGACTGTGCACTCTATGCCTC

GAGCTTTAAAGGCTATATAGAAAACTGTTCAACTCCAAATACGTACATCTGC

ATGCAAAGGACTGTGGCTAGCACCACGACGCCAGCGCCGCGACCACCAACA

CCGGCGCCCACCATCGCGTCGCAGCCCCTGTCCCTGCGCCCAGAGGCGTGCC

GGCCAGCGGCGGGGGGCGCAGTGCACACGAGGGGGCTGGACTTCGCCTGTG

ATATCTACATCTGGGCGCCCTTGGCCGGGACTTGTGGGGTCCTTCTCCTGTCA

CTGGTTATCACCCTTTACTGCCAACGAAGGAAATATAGATCAAACAAAGGAG

AAAGTCCTGTGGAGCCTGCAGAGCCTTGTCGTTACAGCTGCCCCAGGGAGGA

GGAGGGCAGCACCATCCCCATCCAGGAGGATTACCGAAAACCGGAGCCTGC

CTGCTCCCCCAGAGTGAAGTTCAGCAGGAGCGCAGACGCCCCCGCGTACCAG

CAGGGCCAGAACCAGCTCTATAACGAGCTCAATCTAGGACGAAGAGAGGAG

TACGATGTTTTGGACAAGAGACGTGGCCGGGACCCTGAGATGGGGGGAAAG

CCGAGAAGGAAGAACCCTCAGGAAGGCCTGTACAATGAACTGCAGAAAGAT

AAGATGGCGGAGGCCTACAGTGAGATTGGGATGAAAGGCGAGCGCCGGAGG

GGCAAGGGGCACGATGGCCTTTACCAGGGTCTCAGTACAGCCACCAAGGACA

CCTACGACGCCCTTCACATGCAGGCCCTGCCCCCTCGCTAAGTCGACAATCA

ACCTCTGGATTACAAAATTTGTGAAAGATTGACTGGTATTCTTAACTATGTTG

CTCCTTTTACGCTATGTGGATACGCTGCTTTAATGCCTTTGTATCATGCTATTG

CTTCCCGTATGGCTTTCATTTTCTCCTCCTTGTATAAATCCTGGTTGCTGTCTC

TTTATGAGGAGTTGTGGCCCGTTGTCAGGCAACGTGGCGTGGTGTGCACTGTG

TTTGCTGACGCAACCCCCACTGGTTGGGGCATTGCCACCACCTGTCAGCTCCT

TTCCGGGACTTTCGCTTTCCCCCTCCCTATTGCCACGGCGGAACTCATCGCCG

CCTGCCTTGCCCGCTGCTGGACAGGGGCTCGGCTGTTGGGCACTGACAATTCC

GTGGTGTTGTCGGGGAAGCTGACGTCCTTTCCATGGCTGCTCGCCTGTGTTGC

CACCTGGATTCTGCGCGGGACGTCCTTCTGCTACGTCCCTTCGGCCCTCAATC

CAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCC

TGGAATTCGAGCTCGGTACCTTTAAGACCAATGACTTACAAGGCAGCTGTAG

ATCTTAGCCACTTTTTAAAAGAAAAGGGGGGACTGGAAGGGCTAATTCACTC

CCAACGAAGACAAGATCTGCTTTTTGCTTGTACTGGGTCTCTCTGGTTAGACC

AGATCTGAGCCTGGGAGCTCTCTGGCTAACTAGGGAACCCACTGCTTAAGCC

TCAATAAAGCTTGCCTTGAGTGCTTCAAGTAGTGTGTGCCCGTCTGTTGTGTG

ACTCTGGTAACTAGAGATCCCTCAGACCCTTTTAGTCAGTGTGGAAAATCTCT

AGCAGTAGTAGTTCATGTCATCTTATTATTCAGTATTTATAACTTGCAAAGAA

ATGAATATCAGAGAGTGAGAGGAACTTGTTTATTGCAGCTTATAATGGTTAC

AAATAAAGCAATAGCATCACAAATTTCACAAATAAAGCATTTTTTTCACTGC

ATTCTAGTTGTGGTTTGTCCAAACTCATCAATGTATCTTATCATGTCTGGCTCT

-continued

```
AGCTATCCCGCCCCTAACTCCGCCCAGTTCCGCCCATTCTCCGCCCCATGGCT

GACTAATTTTTTTTATTTATGCAGAGGCCGAGGCCGCCTCGGCCTCTGAGCTA

TTCCAGAAGTAGTGAGGAGGCTTTTTTGGAGGCCTAGGCTTTTGCGTCGAGAC

GTACCCAATTCGCCCTATAGTGAGTCGTATTACGCGCGCTCACTGGCCGTCGT

TTTACAACGTCGTGACTGGGAAAACCCTGGCGTTACCCAACTTAATCGCCTTG

CAGCACATCCCCCTTTCGCCAGCTGGCGTAATAGCGAAGAGGCCCGCACCGA

TCGCCCTTCCCAACAGTTGCGCAGCCTGAATGGCGAATGGCGCGACGCGCCC

TGTAGCGGCGCATTAAGCGCGGCGGGTGTGGTGGTTACGCGCAGCGTGACCG

CTACACTTGCCAGCGCCCTAGCGCCCGCTCCTTTCGCTTTCTTCCCTTCCTTTC

TCGCCACGTTCGCCGGCTTTCCCCGTCAAGCTCTAAATCGGGGGCTCCCTTTA

GGGTTCCGATTTAGTGCTTTACGGCACCTCGACCCCAAAAAACTTGATTAGGG

TGATGGTTCACGTAGTGGGCCATCGCCCTGATAGACGGTTTTTCGCCCTTTGA

CGTTGGAGTCCACGTTCTTTAATAGTGGACTCTTGTTCCAAACTGGAACAACA

CTCAACCCTATCTCGGTCTATTCTTTTGATTTATAAGGGATTTTGCCGATTTCG

GCCTATTGGTTAAAAAATGAGCTGATTTAACAAAAATTTAACGCGAATTTTA

ACAAAATATTAACGTTTACAATTTCCCAGGTGGCACTTTTCGGGGAAATGTGC

GCGGAACCCCTATTTGTTTATTTTTCTAAATACATTCAAATATGTATCCGCTCA

TGAGACAATAACCCTGATAAATGCTTCAATAATATTGAAAAAGGAAGAGTAT

GAGTATTCAACATTTCCGTGTCGCCCTTATTCCCTTTTTTGCGGCATTTTGCCT

TCCTGTTTTTGCTCACCCAGAAACGCTGGTGAAAGTAAAAGATGCTGAAGAT

CAGTTGGGTGCACGAGTGGGTTACATCGAACTGGATCTCAACAGCGGTAAGA

TCCTTGAGAGTTTTCGCCCCGAAGAACGTTTTCCAATGATGAGCACTTTTAAA

GTTCTGCTATGTGGCGCGGTATTATCCCGTATTGACGCCGGGCAAGAGCAACT

CGGTCGCCGCATACACTATTCTCAGAATGACTTGGTTGAGTACTCACCAGTCA

CAGAAAAGCATCTTACGGATGGCATGACAGTAAGAGAATTATGCAGTGCTGC

CATAACCATGAGTGATAACACTGCGGCCAACTTACTTCTGACAACGATCGGA

GGACCGAAGGAGCTAACCGCTTTTTTGCACAACATGGGGGATCATGTAACTC

GCCTTGATCGTTGGGAACCGGAGCTGAATGAAGCCATACCAAACGACGAGCG

TGACACCACGATGCCTGTAGCAATGGCAACAACGTTGCGCAAACTATTAACT

GGCGAACTACTTACTCTAGCTTCCCGGCAACAATTAATAGACTGGATGGAGG

CGGATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGCAG

CACTGGGGCCAGATGGTAAGCCCTCCCGTATCGTAGTTATCTACACGACGGG

GAGTCAGGCAACTATGGATGAACGAAATAGACAGATCGCTGAGATAGGTGC

CTCACTGATTAAGCATTGGTAACTGTCAGACCAAGTTTACTCATATATACTTT

AGATTGATTTAAAACTTCATTTTTAATTTAAAAGGATCTAGGTGAAGATCCTT

TTTGATAATCTCATGACCAAAATCCCTTAACGTGAGTTTTCGTTCCACTGAGC

GTCAGACCCCGTAGAAAAGATCAAAGGATCTTCTTGAGATCCTTTTTTTCTGC

GCGTAATCTGCTGCTTGCAAACAAAAAAACCACCGCTACCAGCGGTGGTTTG

TTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCA
```

CTTCAAGAACTCTGTAGCACCGCCTACATACCTCGCTCTGCTAATCCTGTTAC

CAGTGGCTGCTGCCAGTGGCGATAAGTCGTGTCTTACCGGGTTGGACTCAAG

ACGATAGTTACCGGATAAGGCGCAGCGGTCGGGCTGAACGGGGGGTTCGTGC

ACACAGCCCAGCTTGGAGCGAACGACCTACACCGAACTGAGATACCTACAGC

GTGAGCTATGAGAAAGCGCCACGCTTCCCGAAGGGAGAAAGGCGGACAGGT

ATCCGGTAAGCGGCAGGGTCGGAACAGGAGAGCGCACGAGGGAGCTTCCAG

GGGGAAACGCCTGGTATCTTTATAGTCCTGTCGGGTTTCGCCACCTCTGACTT

GAGCGTCGATTTTTGTGATGCTCGTCAGGGGGGCGGAGCCTATGGAAAAACG

CCAGCAACGCGGCCTTTTTACGGTTCCTGGCCTTTTGCTGGCCTTTTGCTCACA

TGTTCTTTCCTGCGTTATCCCCTGATTCTGTGGATAACCGTATTACCGCCTTTG

AGTGAGCTGATACCGCTCGCCGCAGCCGAACGACCGAGCGCAGCGAGTCAGT

GAGCGAGGAAGCGGAAGAGCGCCCAATACGCAAACCGCCTCTCCCCGCGCG

TTGGCCGATTCATTAATGCAGCTGGCACGACAGGTTTCCCGACTGGAAAGCG

GGCAGTGAGCGCAACGCAATTAATGTGAGTTAGCTCACTCATTAGGCACCCC

AGGCTTTACACTTTATGCTTCCGGCTCGTATGTTGTGTGGAATTGTGAGCGGA

TAACAATTTCACACAGGAAACAGCTATGACCATGATTACGCCAAGCGCGCAA

TTAACCCTCACTAAAGGGAACAAAAGCTGGAGCTGCAAGCTTAATGTAGTCT

TATGCAATACTCTTGTAGTCTTGCAACATGGTAACGATGAGTTAGCAACATGC

CTTACAAGGAGAGAAAAAGCACCGTGCATGCCGATTGGTGGAAGTAAGGTG

GTACGATCGTGCCTTATTAGGAAGGCAACAGACGGGTCTGACATGGATTGGA

CGAACCACTGAATTGCCGCATTGCAGAGATATTGTATTTAAGTGCCTAGCTCG

ATACAATAAACGGGTCTCTCTGGTTAGACCAGATCTGAGCCTGGGAGCTCTCT

GGCTAACTAGGGAACCCACTGCTTAAGCCTCAATAAAGCTTGCCTTGAGTGC

TTCAAGTAGTGTGTGCCCGTCTGTTGTGTGACTCTGGTAACTAGAGATCCCTC

AGACCCTTTTAGTCAGTGTGGAAAATCTCTAGCAGTGGCGCCCGAACAGGGA

CCTGAAAGCGAAAGGGAAACCAGAGCTCTCTCGACGCAGGACTCGGCTTGCT

GAAGCGCGCACGGCAAGAGGCGAGGGGCGGCGACTGGTGAGTACGCCAAAA

ATTTTGACTAGCGGAGGCTAGAAGGAGAGAGATGGGTGCGAGAGCGTCAGT

ATTAAGCGGGGGAGAATTAGATCGCGATGGGAAAAAATTCGGTTAAGGCCA

GGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTA

GACAAATACTGGGACAGCTACAACCATCCCTTCAGACAGGATCAGAAGAACT

TAGATCATTATATAATACAGTAGCAACCCTCTATTGTGTGCATCAAAGGATAG

AGATAAAAGACACCAAGGAAGCTTTAGACAAGATAGAGGAAGAGCAAAACA

AAAGTAAGACCACCGCACAGCAAGCGGCCGCTGATCTTCAGACCTGGAGGA

GGAGATATGAGGGACAATTGGAGAAGTGAATTATATAAATATAAAGTAGTA

AAAATTGAACCATTAGGAGTAGCACCCACCAAGGCAAAGAGAAGAGTGGTG

CAGAGAGAAAAAAGAGCAGTGGGAATAGGAGCTTTGTTCCTTGGGTTCTTGG

GAGCAGCAGGAAGCACTATGGGCGCAGCCTCAATGACGCTGACGGTACAGG

CCAGACAATTATTGTCTGGTATAGTGCAGCAGCAGAACAATTTGCTGAGGGC

-continued

```
TATTGAGGCGCAACAGCATCTGTTGCAACTCACAGTCTGGGGCATCAAGCAG

CTCCAGGCAAGAATCCTGGCTGTGGAAAGATACCTAAAGGATCAACAGCTCC

TGGGGATTTGGGGTTGCTCTGGAAAACTCATTTGCACCACTGCTGTGCCTTGG

AATGCTAGTTGGAGTAATAAATCTCTGGAACAGATTGGAATCACACGACCTG

GATGGAGTGGGACAGAGAAATTAACAATTACACAAGCTTAATACACTCCTTA

ATTGAAGAATCGCAAAACCAGCAAGAAAAGAATGAACAAGAATTATTGGAA

TTAGATAAATGGGCAAGTTTGTGGAATTGGTTTAACATAACAAATTGGCTGT

GGTATATAAAATTATTCATAATGATAGTAGGAGGCTTGGTAGGTTTAAGAAT

AGTTTTTGCTGTACTTTCTATAGTGAATAGAGTTAGGCAGGGATATTCACCAT

TATCGTTTCAGACCCACCTCCCAACCCCGAGGGGACCCGACAGGCCCGAAGG

AATAGAAGAAGAAGGTGGAGAGAGAGACAGAGACAGATCCATTCGATTAGT

GAACGGATCTCGACGGTATCGATTAGACTGTAGCCCAGGAATATGGCAGCTA

GATTGTACACATTTAGAAGGAAAAGTTATCTTGGTAGCAGTTCATGTAGCCA

GTGGATATATAGAAGCAGAAGTAATTCCAGCAGAGACAGGGCAAGAAACAG

CATACTTCCTCTTAAAATTAGCAGGAAGATGGCCAGTAAAAACAGTACATAC

AGACAATGGCAGCAATTTCACCAGTACTACAGTTAAGGCCGCCTGTTGGTGG

GCGGGGATCAAGCAGGAATTTGGCATTCCCTACAATCCCCAAAGTCAAGGAG

TAATAGAATCTATGAATAAAGAATTAAAGAAAATTATAGGACAGGTAAGAG

ATCAGGCTGAACATCTTAAGACAGCAGTACAAATGGCAGTATTCATCCACAA

TTTTAAAAGAAAAGGGGGGATTGGGGGGTACAGTGCAGGGGAAAGAATAGT

AGACATAATAGCAACAGACATACAAACTAAAGAATTACAAAAACAAATTAC

AAAAATTCAAAATTTTCGGGTTTATTACAGGGACAGCAGAGATCCAGTTTGG

CTGCATACGCGTCGTGAGGCTCCGGTGCCCGTCAGTGGGCAGAGCGCACATC

GCCCACAGTCCCCGAGAAGTTGGGGGGAGGGGTCGGCAATTGAACCGGTGC

CTAGAGAAGGTGGCGCGGGGTAAACTGGGAAAGTGATGTCGTGTACTGGCTC

CGCCTTTTTCCCGAGGGTGGGGGAGAACCGTATATAAGTGCAGTAGTCGCCG

TGAACGTTCTTTTTCGCAACGGGTTTGCCGCCAGAACACAGGTAAGTGCCGTG

TGTGGTTCCCGCGGGCCTGGCCTCTTTACGGGTTATGGCCCTTGCGTGCCTTG

AATTACTTCCACCTGGCTGCAGTACGTGATTCTTGATCCCGAGCTTCGGGTTG

GAAGTGGGTGGGAGAGTTCGAGGCCTTGCGCTTAAGGAGCCCCTTCGCCTCG

TGCTTGAGTTGAGGCCTGGCCTGGGCGCTGGGGCCGCCGCGTGCGAATCTGG

TGGCACCTTCGCGCCTGTCTCGCTGCTTTCGATAAGTCTCTAGCCATTTAAAA

TTTTTGATGACCTGCTGCGACGCTTTTTTTCTGGCAAGATAGTCTTGTAAATGC

GGGCCAAGATCTGCACACTGGTATTTCGGTTTTTGGGGCCGCGGGCGGCGAC

GGGGCCCGTGCGTCCCAGCGCACATGTTCGGCGAGGCGGGGCCTGCGAGCGC

GGCCACCGAGAATCGGACGGGGGTAGTCTCAAGCTGGCCGGCCTGCTCTGGT

GCCTGGCCTCGCGCCGCCGTGTATCGCCCCGCCCTGGGCGGCAAGGCTGGCC

CGGTCGGCACCAGTTGCGTGAGCGGAAAGATGGCCGCTTCCCGGCCCTGCTG

CAGGGAGCTCAAAATGGAGGACGCGGCGCTCGGGAGAGCGGGCGGGTGAGT

CACCCACACAAAGGAAAAGGGCCTTTCCGTCCTCAGCCGTCGCTTCATGTGA

CTCCACGGAGTACCGGGCGCCGTCCAGGCACCTCGATTAGTTCTCGAGCTTTT
```

-continued

```
GGAGTACGTCGTCTTTAGGTTGGGGGGAGGGGTTTTATGCGATGGAGTTTCCC

CACACTGAGTGGGTGGAGACTGAAGTTAGGCCAGCTTGGCACTTGATGTAAT

TCTCCTTGGAATTTGCCCTTTTTGAGTTTGGATCTTGGTTCATTCTCAAGCCTC

AGACAGTGGTTCAAAGTTTTTTTCTTCCATTTCAGGTGTCGTGAGCTAGCTCT

AGAG
```

NKG2D nucleic acid sequence (SEQ ID NO: 2)

```
TTCAACCAAGAAGTTCAAATTCCCTTGACCGAAAGTTACTGTGGCCCATGTCC

TAAAAACTGGATATGTTACAAAAATAACTGCTACCAATTTTTTGATGAGAGT

AAAAACTGGTATGAGAGCCAGGCTTCTTGTATGTCTCAAAATGCCAGCCTTCT

GAAAGTATACAGCAAAGAGGACCAGGATTTACTTAAACTGGTGAAGTCATAT

CATTGGATGGGACTAGTACACATTCCAACAAATGGATCTTGGCAGTGGGAAG

ATGGCTCCATTCTCTCACCCAACCTACTAACAATAATTGAAATGCAGAAGGG

AGACTGTGCACTCTATGCCTCGAGCTTTAAAGGCTATATAGAAAACTGTTCAA

CTCCAAATACGTACATCTGCATGCAAAGGACTGTG
```

NKG2D amino acid sequence (SEQ ID NO: 3)

```
FNQEVQIPLTESYCGPCPKNWICYKNNCYQFFDESKNWYESQASCMSQNASLLK

VYSKEDQDLLKLVKSYHWMGLVHIPTNGSWQWEDGSILSPNLLTIIEMQKGDCA

LYASSFKGYIENCSTPNTYICMQRTV
```

CD27 nucleic acid sequence (SEQ ID NO: 4)

```
CAACGAAGGAAATATAGATCAAACAAAGGAGAAAGTCCTGTGGAGCCTGCA

GAGCCTTGTCGTTACAGCTGCCCCAGGGAGGAGGAGGGCAGCACCATCCCCA

TCCAGGAGGATTACCGAAAACCGGAGCCTGCCTGCTCCCCC
```

CD27 amino acid sequence (SEQ ID NO: 5)

```
QRRKYRSNKGESPVEPAEPCRYSCPREEEGSTIPIQEDYRKPEPACSP
```

NKG2D_CD27_CD3Zeta CAR nucleic acid sequence (SEQ ID NO: 14)

```
TTCAACCAAGAAGTTCAAATTCCCTTGACCGAAAGTTACTGTGGCCCATGTCC

TAAAAACTGGATATGTTACAAAAATAACTGCTACCAATTTTTTGATGAGAGT

AAAAACTGGTATGAGAGCCAGGCTTCTTGTATGTCTCAAAATGCCAGCCTTCT

GAAAGTATACAGCAAAGAGGACCAGGATTTACTTAAACTGGTGAAGTCATAT

CATTGGATGGGACTAGTACACATTCCAACAAATGGATCTTGGCAGTGGGAAG

ATGGCTCCATTCTCTCACCCAACCTACTAACAATAATTGAAATGCAGAAGGG

AGACTGTGCACTCTATGCCTCGAGCTTTAAAGGCTATATAGAAAACTGTTCAA

CTCCAAATACGTACATCTGCATGCAAAGGACTGTGGCTAGCACCACGACGCC

AGCGCCGCGACCACCAACACCGGCGCCCACCATCGCGTCGCAGCCCCTGTCC

CTGCGCCCAGAGGCGTGCCGGCCAGCGGCGGGGGGCGCAGTGCACACGAGG

GGGCTGGACTTCGCCTGTGATATCTACATCTGGGCGCCCTTGGCCGGGACTTG

TGGGGTCCTTCTCCTGTCACTGGTTATCACCCTTTACTGCCAACGAAGGAAAT

ATAGATCAAACAAAGGAGAAAGTCCTGTGGAGCCTGCAGAGCCTTGTCGTTA

CAGCTGCCCCAGGGAGGAGGAGGGCAGCACCATCCCCATCCAGGAGGATTA

CCGAAAACCGGAGCCTGCCTGCTCCCCCAGAGTGAAGTTCAGCAGGAGCGCA
```

GACGCCCCCGCGTACCAGCAGGGCCAGAACCAGCTCTATAACGAGCTCAATC

TAGGACGAAGAGAGGAGTACGATGTTTTGGACAAGAGACGTGGCCGGGACC

CTGAGATGGGGGGAAAGCCGAGAAGGAAGAACCCTCAGGAAGGCCTGTACA

ATGAACTGCAGAAAGATAAGATGGCGGAGGCCTACAGTGAGATTGGGATGA

AAGGCGAGCGCCGGAGGGGCAAGGGGCACGATGGCCTTTACCAGGGTCTCA

GTACAGCCACCAAGGACACCTACGACGCCCTTCACATGCAGGCCCTGCCCCC

TCGC

NKG2D_CD27_CD3Zeta CAR amino acid sequence (SEQ ID NO: 15)

FNQEVQIPLTESYCGPCPKNWICYKNNCYQFFDESKNWYESQASCMSQNASLLK

VYSKEDQDLLKLVKSYHWMGLVHIPTNGSWQWEDGSILSPNLLTIIEMQKGDCA

LYASSFKGYIENCSTPNTYICMQRTVASTTTPAPRPPTPAPTIASQPLSLRPEACRP

AAGGAVHTRGLDFACDIYIWAPLAGTCGVLLLSLVITLYCQRRKYRSNKGESPV

EPAEPCRYSCPREEEGSTIPIQEDYRKPEPACSPRVKFSRSADAPAYQQGQNQLYN

ELNLGRREEYDVLDKRRGRDPEMGGKPRRKNPQEGLYNELQKDKMAEAYSEIG

MKGERRRGKGHDGLYQGLSTATKDTYDALHMQALPPR (2) CAR vector: PELNS_eGFP_2A_NKG2D_41BB_CD3Zeta (SEQ ID NO: 6)

ATGGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGCG

AGGGCGATGCCACCTACGGCAAGCTGACCCTGAAGTTCATCTGCACCACCGG

CAAGCTGCCCGTGCCCTGGCCCACCCTCGTGACCACCCTGACCTACGGCGTG

CAGTGCTTCAGCCGCTACCCCGACCACATGAAGCAGCACGACTTCTTCAAGT

CCGCCATGCCCGAAGGCTACGTCCAGGAGCGCACCATCTTCTTCAAGGACGA

CGGCAACTACAAGACCCGCGCCGAGGTGAAGTTCGAGGGCGACACCCTGGT

GAACCGCATCGAGCTGAAGGGCATCGACTTCAAGGAGGACGGCAACATCCT

GGGGCACAAGCTGGAGTACAACTACAACAGCCACAACGTCTATATCATGGCC

GACAAGCAGAAGAACGGCATCAAGGTGAACTTCAAGATCCGCCACAACATC

GAGGACGGCAGCGTGCAGCTCGCCGACCACTACCAGCAGAACACCCCCATCG

GCGACGGCCCCGTGCTGCTGCCCGACAACCACTACCTGAGCACCCAGTCCGC

CCTGAGCAAAGACCCCAACGAGAAGCGCGATCACATGGTCCTGCTGGAGTTC

GTGACCGCCGCCGGGATCACTCTCGGCATGGACGAGCTGTACAAGAGATCTG

GCGGCGGAGAGGGCAGAGGAAGTCTTCTAACATGCGGTGACGTGGAGGAGA

ATCCCGGCCCTAGATGGCCTTACCAGTGACCGCCTTGCTCCTGCCGCTGGCCT

TGCTGCTCCACGCCGCCAGGCCGGGATCCTTCAACCAAGAAGTTCAAATTCC

CTTGACCGAAAGTTACTGTGGCCCATGTCCTAAAAACTGGATATGTTACAAA

AATAACTGCTACCAATTTTTTGATGAGAGTAAAAACTGGTATGAGAGCCAGG

CTTCTTGTATGTCTCAAAATGCCAGCCTTCTGAAAGTATACAGCAAAGAGGA

CCAGGATTTACTTAAACTGGTGAAGTCATATCATTGGATGGGACTAGTACAC

ATTCCAACAAATGGATCTTGGCAGTGGGAAGATGGCTCCATTCTCTCACCCA

ACCTACTAACAATAATTGAAATGCAGAAGGGAGACTGTGCACTCTATGCCTC

GAGCTTTAAAGGCTATATAGAAAACTGTTCAACTCCAAATACGTACATCTGC

ATGCAAAGGACTGTGGCTAGCACCACGACGCCAGCGCCGCGACCACCAACA

```
CCGGCGCCCACCATCGCGTCGCAGCCCCTGTCCCTGCGCCCAGAGGCGTGCC

GGCCAGCGGCGGGGGGCGCAGTGCACACGAGGGGGCTGGACTTCGCCTGTG

ATATCTACATCTGGGCGCCCTTGGCCGGGACTTGTGGGGTCCTTCTCCTGTCA

CTGGTTATCACCCTTTACTGCAAACGGGGCAGAAAGAAACTCCTGTATATATT

CAAACAACCATTTATGAGACCAGTACAAACTACTCAAGAGGAAGATGGCTGT

AGCTGCCGATTTCCAGAAGAAGAAGAAGGAGGATGTGAACTGAGAGTGAAG

TTCAGCAGGAGCGCAGACGCCCCCGCGTACCAGCAGGGCCAGAACCAGCTCT

ATAACGAGCTCAATCTAGGACGAAGAGAGGAGTACGATGTTTTGGACAAGA

GACGTGGCCGGGACCCTGAGATGGGGGGAAAGCCGAGAAGGAAGAACCCTC

AGGAAGGCCTGTACAATGAACTGCAGAAAGATAAGATGGCGGAGGCCTACA

GTGAGATTGGGATGAAAGGCGAGCGCCGGAGGGGCAAGGGGCACGATGGCC

TTTACCAGGGTCTCAGTACAGCCACCAAGGACACCTACGACGCCCTTCACAT

GCAGGCCCTGCCCCCTCGCTAAGTCGACAATCAACCTCTGGATTACAAAATTT

GTGAAAGATTGACTGGTATTCTTAACTATGTTGCTCCTTTTACGCTATGTGGA

TACGCTGCTTTAATGCCTTTGTATCATGCTATTGCTTCCCGTATGGCTTTCATT

TTCTCCTCCTTGTATAAATCCTGGTTGCTGTCTCTTTATGAGGAGTTGTGGCCC

GTTGTCAGGCAACGTGGCGTGGTGTGCACTGTGTTTGCTGACGCAACCCCCAC

TGGTTGGGGCATTGCCACCACCTGTCAGCTCCTTTCCGGGACTTTCGCTTTCC

CCCTCCCTATTGCCACGGCGGAACTCATCGCCGCCTGCCTTGCCCGCTGCTGG

ACAGGGGCTCGGCTGTTGGGCACTGACAATTCCGTGGTGTTGTCGGGGAAGC

TGACGTCCTTTCCATGGCTGCTCGCCTGTGTTGCCACCTGGATTCTGCGCGGG

ACGTCCTTCTGCTACGTCCCTTCGGCCCTCAATCCAGCGGACCTTCCTTCCCG

CGGCCTGCTGCCGGCTCTGCGGCCTCTTCCGCGTCTTCGCCTTCGCCCTCAGA

CGAGTCGGATCTCCCTTTGGGCCGCCTCCCCGCCTGGAATTCGAGCTCGGTAC

CTTTAAGACCAATGACTTACAAGGCAGCTGTAGATCTTAGCCACTTTTTAAAA

GAAAAGGGGGGACTGGAAGGGCTAATTCACTCCCAACGAAGACAAGATCTG

CTTTTTGCTTGTACTGGGTCTCTCTGGTTAGACCAGATCTGAGCCTGGGAGCT

CTCTGGCTAACTAGGGAACCCACTGCTTAAGCCTCAATAAAGCTTGCCTTGAG

TGCTTCAAGTAGTGTGTGCCCGTCTGTTGTGTGACTCTGGTAACTAGAGATCC

CTCAGACCCTTTTAGTCAGTGTGGAAAATCTCTAGCAGTAGTAGTTCATGTCA

TCTTATTATTCAGTATTTATAACTTGCAAAGAAATGAATATCAGAGAGTGAGA

GGAACTTGTTTATTGCAGCTTATAATGGTTACAAATAAAGCAATAGCATCAC

AAATTTCACAAATAAAGCATTTTTTTCACTGCATTCTAGTTGTGGTTTGTCCA

AACTCATCAATGTATCTTATCATGTCTGGCTCTAGCTATCCCGCCCCTAACTC

CGCCCAGTTCCGCCCATTCTCCGCCCCATGGCTGACTAATTTTTTTTATTTATG

CAGAGGCCGAGGCCGCCTCGGCCTCTGAGCTATTCCAGAAGTAGTGAGGAGG

CTTTTTTGGAGGCCTAGGCTTTTGCGTCGAGACGTACCCAATTCGCCCTATAG

TGAGTCGTATTACGCGCGCTCACTGGCCGTCGTTTTACAACGTCGTGACTGGG

AAAACCCTGGCGTTACCCAACTTAATCGCCTTGCAGCACATCCCCCTTTCGCC

AGCTGGCGTAATAGCGAAGAGGCCCGCACCGATCGCCCTTCCCAACAGTTGC
```

-continued

```
GCAGCCTGAATGGCGAATGGCGCGACGCGCCCTGTAGCGGCGCATTAAGCGC

GGCGGGTGTGGTGGTTACGCGCAGCGTGACCGCTACACTTGCCAGCGCCCTA

GCGCCCGCTCCTTTCGCTTTCTTCCCTTCCTTTCTCGCCACGTTCGCCGGCTTT

CCCCGTCAAGCTCTAAATCGGGGGCTCCCTTTAGGGTTCCGATTTAGTGCTTT

ACGGCACCTCGACCCCAAAAAACTTGATTAGGGTGATGGTTCACGTAGTGGG

CCATCGCCCTGATAGACGGTTTTTCGCCCTTTGACGTTGGAGTCCACGTTCTTT

AATAGTGGACTCTTGTTCCAAACTGGAACAACACTCAACCCTATCTCGGTCTA

TTCTTTTGATTTATAAGGGATTTTGCCGATTTCGGCCTATTGGTTAAAAAATG

AGCTGATTTAACAAAAATTTAACGCGAATTTTAACAAAATATTAACGTTTACA

ATTTCCCAGGTGGCACTTTTCGGGGAAATGTGCGCGGAACCCCTATTTGTTTA

TTTTTCTAAATACATTCAAATATGTATCCGCTCATGAGACAATAACCCTGATA

AATGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCACCCA

GAAACGCTGGTGAAAGTAAAAGATGCTGAAGATCAGTTGGGTGCACGAGTG

GGTTACATCGAACTGGATCTCAACAGCGGTAAGATCCTTGAGAGTTTTCGCCC

CGAAGAACGTTTTCCAATGATGAGCACTTTTAAAGTTCTGCTATGTGGCGCGG

TATTATCCCGTATTGACGCCGGGCAAGAGCAACTCGGTCGCCGCATACACTA

TTCTCAGAATGACTTGGTTGAGTACTCACCAGTCACAGAAAAGCATCTTACG

GATGGCATGACAGTAAGAGAATTATGCAGTGCTGCCATAACCATGAGTGATA

ACACTGCGGCCAACTTACTTCTGACAACGATCGGAGGACCGAAGGAGCTAAC

CGCTTTTTTGCACAACATGGGGGATCATGTAACTCGCCTTGATCGTTGGGAAC

CGGAGCTGAATGAAGCCATACCAAACGACGAGCGTGACACCACGATGCCTGT

AGCAATGGCAACAACGTTGCGCAAACTATTAACTGGCGAACTACTTACTCTA

GCTTCCCGGCAACAATTAATAGACTGGATGGAGGCGGATAAAGTTGCAGGAC

CACTTCTGCGCTCGGCCCTTCCGGCTGGCTGGTTTATTGCTGATAAATCTGGA

GCCGGTGAGCGTGGGTCTCGCGGTATCATTGCAGCACTGGGGCCAGATGGTA

AGCCCTCCCGTATCGTAGTTATCTACACGACGGGGAGTCAGGCAACTATGGA

TGAACGAAATAGACAGATCGCTGAGATAGGTGCCTCACTGATTAAGCATTGG

TAACTGTCAGACCAAGTTTACTCATATATACTTTAGATTGATTTAAAACTTCA

TTTTTAATTTAAAAGGATCTAGGTGAAGATCCTTTTTTGATAATCTCATGACCA

AAATCCCTTAACGTGAGTTTTCGTTCCACTGAGCGTCAGACCCCGTAGAAAA

GATCAAAGGATCTTCTTGAGATCCTTTTTTTCTGCGCGTAATCTGCTGCTTGCA

AACAAAAAAACCACCGCTACCAGCGGTGGTTTGTTTGCCGGATCAAGAGCTA

CCAACTCTTTTTCCGAAGGTAACTGGCTTCAGCAGAGCGCAGATACCAAATA

CTGTCCTTCTAGTGTAGCCGTAGTTAGGCCACCACTTCAAGAACTCTGTAGCA

CCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAG

GCGCAGCGGTCGGGCTGAACGGGGGGTTCGTGCACACAGCCCAGCTTGGAGC

GAACGACCTACACCGAACTGAGATACCTACAGCGTGAGCTATGAGAAAGCG

CCACGCTTCCCGAAGGGAGAAAGGCGGACAGGTATCCGGTAAGCGGCAGGG

TCGGAACAGGAGAGCGCACGAGGGAGCTTCCAGGGGGAAACGCCTGGTATC
```

-continued

```
TTTATAGTCCTGTCGGGTTTCGCCACCTCTGACTTGAGCGTCGATTTTTGTGAT

GCTCGTCAGGGGGGCGGAGCCTATGGAAAAACGCCAGCAACGCGGCCTTTTT

ACGGTTCCTGGCCTTTTGCTGGCCTTTTGCTCACATGTTCTTTCCTGCGTTATC

CCCTGATTCTGTGGATAACCGTATTACCGCCTTTGAGTGAGCTGATACCGCTC

GCCGCAGCCGAACGACCGAGCGCAGCGAGTCAGTGAGCGAGGAAGCGGAAG

AGCGCCCAATACGCAAACCGCCTCTCCCCGCGCGTTGGCCGATTCATTAATG

CAGCTGGCACGACAGGTTTCCCGACTGGAAAGCGGGCAGTGAGCGCAACGC

AATTAATGTGAGTTAGCTCACTCATTAGGCACCCCAGGCTTTACACTTTATGC

TTCCGGCTCGTATGTTGTGTGGAATTGTGAGCGGATAACAATTTCACACAGGA

AACAGCTATGACCATGATTACGCCAAGCGCGCAATTAACCCTCACTAAAGGG

AACAAAAGCTGGAGCTGCAAGCTTAATGTAGTCTTATGCAATACTCTTGTAGT

CTTGCAACATGGTAACGATGAGTTAGCAACATGCCTTACAAGGAGAGAAAAA

GCACCGTGCATGCCGATTGGTGGAAGTAAGGTGGTACGATCGTGCCTTATTA

GGAAGGCAACAGACGGGTCTGACATGGATTGGACGAACCACTGAATTGCCGC

ATTGCAGAGATATTGTATTTAAGTGCCTAGCTCGATACAATAAACGGGTCTCT

CTGGTTAGACCAGATCTGAGCCTGGGAGCTCTCTGGCTAACTAGGGAACCCA

CTGCTTAAGCCTCAATAAAGCTTGCCTTGAGTGCTTCAAGTAGTGTGTGCCCG

TCTGTTGTGTGACTCTGGTAACTAGAGATCCCTCAGACCCTTTTAGTCAGTGT

GGAAAATCTCTAGCAGTGGCGCCCGAACAGGGACCTGAAAGCGAAAGGGAA

ACCAGAGCTCTCTCGACGCAGGACTCGGCTTGCTGAAGCGCGCACGGCAAGA

GGCGAGGGGCGGCGACTGGTGAGTACGCCAAAAATTTTGACTAGCGGAGGCT

AGAAGGAGAGAGATGGGTGCGAGAGCGTCAGTATTAAGCGGGGGAGAATTA

GATCGCGATGGGAAAAAATTCGGTTAAGGCCAGGGGGAAAGAAAAAATATA

AATTAAAACATATAGTATGGGCAAGCAGGGAGCTAGAACGATTCGCAGTTAA

TCCTGGCCTGTTAGAAACATCAGAAGGCTGTAGACAAATACTGGGACAGCTA

CAACCATCCCTTCAGACAGGATCAGAAGAACTTAGATCATTATATAATACAG

TAGCAACCCTCTATTGTGTGCATCAAAGGATAGAGATAAAAGACACCAAGGA

AGCTTTAGACAAGATAGAGGAAGAGCAAAACAAAGTAAGACCACCGCACA

GCAAGCGGCCGCTGATCTTCAGACCTGGAGGAGGAGATATGAGGGACAATTG

GAGAAGTGAATTATATAAATATAAAGTAGTAAAAATTGAACCATTAGGAGTA

GCACCCACCAAGGCAAAGAGAAGAGTGGTGCAGAGAGAAAAAAGAGCAGTG

GGAATAGGAGCTTTGTTCCTTGGGTTCTTGGGAGCAGCAGGAAGCACTATGG

GCGCAGCCTCAATGACGCTGACGGTACAGGCCAGACAATTATTGTCTGGTAT

AGTGCAGCAGCAGAACAATTTGCTGAGGGCTATTGAGGCGCAACAGCATCTG

TTGCAACTCACAGTCTGGGGCATCAAGCAGCTCCAGGCAAGAATCCTGGCTG

TGGAAAGATACCTAAAGGATCAACAGCTCCTGGGGATTTGGGGTTGCTCTGG

AAAACTCATTTGCACCACTGCTGTGCCTTGGAATGCTAGTTGGAGTAATAAAT

CTCTGGAACAGATTGGAATCACACGACCTGGATGGAGTGGGACAGAGAAATT

AACAATTACACAAGCTTAATACACTCCTTAATTGAAGAATCGCAAAACCAGC

AAGAAAAGAATGAACAAGAATTATTGGAATTAGATAAATGGGCAAGTTTGTG
```

-continued

```
GAATTGGTTTAACATAACAAATTGGCTGTGGTATATAAAATTATTCATAATGA

TAGTAGGAGGCTTGGTAGGTTTAAGAATAGTTTTTGCTGTACTTTCTATAGTG

AATAGAGTTAGGCAGGGATATTCACCATTATCGTTTCAGACCCACCTCCCAAC

CCCGAGGGGACCCGACAGGCCCGAAGGAATAGAAGAAGAAGGTGGAGAGA

GAGACAGAGACAGATCCATTCGATTAGTGAACGGATCTCGACGGTATCGATT

AGACTGTAGCCCAGGAATATGGCAGCTAGATTGTACACATTTAGAAGGAAAA

GTTATCTTGGTAGCAGTTCATGTAGCCAGTGGATATATAGAAGCAGAAGTAA

TTCCAGCAGAGACAGGGCAAGAAACAGCATACTTCCTCTTAAAATTAGCAGG

AAGATGGCCAGTAAAAACAGTACATACAGACAATGGCAGCAATTTCACCAGT

ACTACAGTTAAGGCCGCCTGTTGGTGGGCGGGGATCAAGCAGGAATTTGGCA

TTCCCTACAATCCCCAAAGTCAAGGAGTAATAGAATCTATGAATAAAGAATT

AAAGAAAATTATAGGACAGGTAAGAGATCAGGCTGAACATCTTAAGACAGC

AGTACAAATGGCAGTATTCATCCACAATTTTAAAAGAAAAGGGGGGATTGGG

GGGTACAGTGCAGGGGAAAGAATAGTAGACATAATAGCAACAGACATACAA

ACTAAAGAATTACAAAAACAAATTACAAAAATTCAAAATTTTCGGGTTTATT

ACAGGGACAGCAGAGATCCAGTTTGGCTGCATACGCGTCGTGAGGCTCCGGT

GCCCGTCAGTGGGCAGAGCGCACATCGCCCACAGTCCCCGAGAAGTTGGGGG

GAGGGGTCGGCAATTGAACCGGTGCCTAGAGAAGGTGGCGCGGGGTAAACT

GGGAAAGTGATGTCGTGTACTGGCTCCGCCTTTTTCCCGAGGGTGGGGGAGA

ACCGTATATAAGTGCAGTAGTCGCCGTGAACGTTCTTTTTCGCAACGGGTTTG

CCGCCAGAACACAGGTAAGTGCCGTGTGTGGTTCCCGCGGGCCTGGCCTCTT

TACGGGTTATGGCCCTTGCGTGCCTTGAATTACTTCCACCTGGCTGCAGTACG

TGATTCTTGATCCCGAGCTTCGGGTTGGAAGTGGGTGGGAGAGTTCGAGGCC

TTGCGCTTAAGGAGCCCCTTCGCCTCGTGCTTGAGTTGAGGCCTGGCCTGGGC

GCTGGGGCCGCCGCGTGCGAATCTGGTGGCACCTTCGCGCCTGTCTCGCTGCT

TTCGATAAGTCTCTAGCCATTTAAAATTTTTGATGACCTGCTGCGACGCTTTTT

TTCTGGCAAGATAGTCTTGTAAATGCGGGCCAAGATCTGCACACTGGTATTTC

GGTTTTTGGGGCCGCGGGCGGCGACGGGGCCCGTGCGTCCCAGCGCACATGT

TCGGCGAGGCGGGGCCTGCGAGCGCGGCCACCGAGAATCGGACGGGGGTAG

TCTCAAGCTGGCCGGCCTGCTCTGGTGCCTGGCCTCGCGCCGCCGTGTATCGC

CCCGCCCTGGGCGGCAAGGCTGGCCCGGTCGGCACCAGTTGCGTGAGCGGAA

AGATGGCCGCTTCCCGGCCCTGCTGCAGGGAGCTCAAAATGGAGGACGCGGC

GCTCGGGAGAGCGGGCGGGTGAGTCACCCACACAAAGGAAAAGGGCCTTTC

CGTCCTCAGCCGTCGCTTCATGTGACTCCACGGAGTACCGGGCGCCGTCCAG

GCACCTCGATTAGTTCTCGAGCTTTTGGAGTACGTCGTCTTTAGGTTGGGGGG

AGGGGTTTTATGCGATGGAGTTTCCCCACACTGAGTGGGTGGAGACTGAAGT

TAGGCCAGCTTGGCACTTGATGTAATTCTCCTTGGAATTTGCCCTTTTTGAGTT

TGGATCTTGGTTCATTCTCAAGCCTCAGACAGTGGTTCAAAGTTTTTTTCTTCC

ATTTCAGGTGTCGTGAGCTAGCTCTAGAG
```

-continued

NKG2D_41BB_CD3Zeta CAR nucleic acid sequence
                                                          (SEQ ID NO: 16)
TTCAACCAAGAAGTTCAAATTCCCTTGACCGAAAGTTACTGTGGCCCATGTCC

TAAAAACTGGATATGTTACAAAAATAACTGCTACCAATTTTTTGATGAGAGT

AAAAACTGGTATGAGAGCCAGGCTTCTTGTATGTCTCAAAATGCCAGCCTTCT

GAAAGTATACAGCAAAGAGGACCAGGATTTACTTAAACTGGTGAAGTCATAT

CATTGGATGGGACTAGTACACATTCCAACAAATGGATCTTGGCAGTGGGAAG

ATGGCTCCATTCTCTCACCCAACCTACTAACAATAATTGAAATGCAGAAGGG

AGACTGTGCACTCTATGCCTCGAGCTTTAAAGGCTATATAGAAAACTGTTCAA

CTCCAAATACGTACATCTGCATGCAAAGGACTGTGGCTAGCACCACGACGCC

AGCGCCGCGACCACCAACACCGGCGCCCACCATCGCGTCGCAGCCCCTGTCC

CTGCGCCCAGAGGCGTGCCGGCCAGCGGCGGGGGGCGCAGTGCACACGAGG

GGGCTGGACTTCGCCTGTGATATCTACATCTGGGCGCCCTTGGCCGGGACTTG

TGGGGTCCTTCTCCTGTCACTGGTTATCACCCTTTACTGCAAACGGGGCAGAA

AGAAACTCCTGTATATATTCAAACAACCATTTATGAGACCAGTACAAACTAC

TCAAGAGGAAGATGGCTGTAGCTGCCGATTTCCAGAAGAAGAAGAAGGAGG

ATGTGAACTGAGAGTGAAGTTCAGCAGGAGCGCAGACGCCCCCGCGTACCA

GCAGGGCCAGAACCAGCTCTATAACGAGCTCAATCTAGGACGAAGAGAGGA

GTACGATGTTTTGGACAAGAGACGTGGCCGGGACCCTGAGATGGGGGGAAA

GCCGAGAAGGAAGAACCCTCAGGAAGGCCTGTACAATGAACTGCAGAAAGA

TAAGATGGCGGAGGCCTACAGTGAGATTGGGATGAAAGGCGAGCGCCGGAG

GGGCAAGGGGCACGATGGCCTTTACCAGGGTCTCAGTACAGCCACCAAGGAC

ACCTACGACGCCCTTCACATGCAGGCCCTGCCCCCTCGC

NKG2D_41BB_CD3Zeta CAR amino acid sequence
                                                          (SEQ ID NO: 17)
FNQEVQIPLTESYCGPCPKNWICYKNNCYQFFDESKNWYESQASCMSQNASLLK

VYSKEDQDLLKLVKSYHWMGLVHIPTNGSWQWEDGSILSPNLLTIIEMQKGDCA

LYASSFKGYIENCSTPNTYICMQRTVASTTTPAPRPPTPAPTIASQPLSLRPEACRP

AAGGAVHTRGLDFACDIYIWAPLAGTCGVLLLSLVITLYCKRGRKKLLYIFKQPF

MRPVQTTQEEDGCCRFPEEEEGGCELRVKFSRSADAPAYQQGQNQLYNELNLG

RREEYDVLDKRRGRDPEMGGKPRRKNPQEGLYNELQKDKMAEAYSEIGMKGE

RRRGKGHDGLYQGLSTATKDTYDALHMQALPPR (3) CAR vector: PELNS_eGFP_2A_NKG2D_CD3Zeta
                                                          (SEQ ID NO: 7)
ATGGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGCG

AGGGCGATGCCACCTACGGCAAGCTGACCCTGAAGTTCATCTGCACCACCGG

CAAGCTGCCCGTGCCCTGGCCCACCCTCGTGACCACCCTGACCTACGGCGTG

CAGTGCTTCAGCCGCTACCCCGACCACATGAAGCAGCACGACTTCTTCAAGT

CCGCCATGCCCGAAGGCTACGTCCAGGAGCGCACCATCTTCTTCAAGGACGA

CGGCAACTACAAGACCCGCGCCGAGGTGAAGTTCGAGGGCGACACCCTGGT

GAACCGCATCGAGCTGAAGGGCATCGACTTCAAGGAGGACGGCAACATCCT

GGGGCACAAGCTGGAGTACAACTACAACAGCCACAACGTCTATATCATGGCC

-continued

```
GACAAGCAGAAGAACGGCATCAAGGTGAACTTCAAGATCCGCCACAACATC

GAGGACGGCAGCGTGCAGCTCGCCGACCACTACCAGCAGAACACCCCCATCG

GCGACGGCCCCGTGCTGCTGCCCGACAACCACTACCTGAGCACCCAGTCCGC

CCTGAGCAAAGACCCCAACGAGAAGCGCGATCACATGGTCCTGCTGGAGTTC

GTGACCGCCGCCGGGATCACTCTCGGCATGGACGAGCTGTACAAGAGATCTG

GCGGCGGAGAGGGCAGAGGAAGTCTTCTAACATGCGGTGACGTGGAGGAGA

ATCCCGGCCCTAGATGGCCTTACCAGTGACCGCCTTGCTCCTGCCGCTGGCCT

TGCTGCTCCACGCCGCCAGGCCGGGATCCTTCAACCAAGAAGTTCAAATTCC

CTTGACCGAAAGTTACTGTGGCCCATGTCCTAAAAACTGGATATGTTACAAA

AATAACTGCTACCAATTTTTTGATGAGAGTAAAAACTGGTATGAGAGCCAGG

CTTCTTGTATGTCTCAAAATGCCAGCCTTCTGAAAGTATACAGCAAAGAGGA

CCAGGATTTACTTAAACTGGTGAAGTCATATCATTGGATGGGACTAGTACAC

ATTCCAACAAATGGATCTTGGCAGTGGGAAGATGGCTCCATTCTCTCACCCA

ACCTACTAACAATAATTGAAATGCAGAAGGGAGACTGTGCACTCTATGCCTC

GAGCTTTAAAGGCTATATAGAAAACTGTTCAACTCCAAATACGTACATCTGC

ATGCAAAGGACTGTGGCTAGCACCACGACGCCAGCGCCGCGACCACCAACA

CCGGCGCCCACCATCGCGTCGCGGCCCCTGTCCCTGCGCCCAGAGGCGTGCC

GGCCAGCGGGGGGGCGCAGTGCACACGAGGGGGCTGGACTTCGCCTGTG

ATATCTACATCTGGGCGCCCTTGGCCGGGACTTGTGGGGTCCTTCTCCTGTCA

CTGGTTATCACCCTTTACTGCAGAGTGAAGTTCAGCAGGAGCGCAGACGCCC

CCGCGTACCAGCAGGGCCAGAACCAGCTCTATAACGAGCTCAATCTAGGACG

AAGAGAGGAGTACGATGTTTTGGACAAGAGACGTGGCCGGGACCCTGAGAT

GGGGGGAAAGCCGAGAAGGAAGAACCCTCAGGAAGGCCTGTACAATGAACT

GCAGAAAGATAAGATGGCGGAGGCCTACAGTGAGATTGGGATGAAAGGCGA

GCGCCGGAGGGGCAAGGGGCACGATGGCCTTTACCAGGGTCTCAGTACAGCC

ACCAAGGACACCTACGACGCCCTTCACATGCAGGCCCTGCCCCCTCGCTAAG

TCGACAATCAACCTCTGGATTACAAAATTTGTGAAAGATTGACTGGTATTCTT

AACTATGTTGCTCCTTTTACGCTATGTGGATACGCTGCTTTAATGCCTTTGTAT

CATGCTATTGCTTCCCGTATGGCTTTCATTTTCTCCTCCTTGTATAAATCCTGG

TTGCTGTCTCTTTATGAGGAGTTGTGGCCCGTTGTCAGGCAACGTGGCGTGGT

GTGCACTGTGTTTGCTGACGCAACCCCCACTGGTTGGGGCATTGCCACCACCT

GTCAGCTCCTTTCCGGGACTTTCGCTTTCCCCCTCCCTATTGCCACGGCGGAA

CTCATCGCCGCCTGCCTTGCCCGCTGCTGGACAGGGGCTCGGCTGTTGGGCAC

TGACAATTCCGTGGTGTTGTCGGGGAAGCTGACGTCCTTTCCATGGCTGCTCG

CCTGTGTTGCCACCTGGATTCTGCGCGGGACGTCCTTCTGCTACGTCCCTTCG

GCCCTCAATCCAGCGGACCTTCCTTCCCGCGGCCTGCTGCCGGCTCTGCGGCC

TCTTCCGCGTCTTCGCCTTCGCCCTCAGACGAGTCGGATCTCCCTTTGGGCCG

CCTCCCCGCCTGGAATTCGAGCTCGGTACCTTTAAGACCAATGACTTACAAG

GCAGCTGTAGATCTTAGCCACTTTTTAAAAGAAAAGGGGGGACTGGAAGGGC

TAATTCACTCCCAACGAAGACAAGATCTGCTTTTTGCTTGTACTGGGTCTCTC

TGGTTAGACCAGATCTGAGCCTGGGAGCTCTCTGGCTAACTAGGGAACCCAC
```

-continued

```
TGCTTAAGCCTCAATAAAGCTTGCCTTGAGTGCTTCAAGTAGTGTGTGCCCGT

CTGTTGTGTGACTCTGGTAACTAGAGATCCCTCAGACCCTTTTAGTCAGTGTG

GAAAATCTCTAGCAGTAGTAGTTCATGTCATCTTATTATTCAGTATTTATAAC

TTGCAAAGAAATGAATATCAGAGAGTGAGAGGAACTTGTTTATTGCAGCTTA

TAATGGTTACAAATAAAGCAATAGCATCACAAATTTCACAAATAAAGCATTT

TTTTCACTGCATTCTAGTTGTGGTTTGTCCAAACTCATCAATGTATCTTATCAT

GTCTGGCTCTAGCTATCCCGCCCCTAACTCCGCCCAGTTCCGCCCATTCTCCG

CCCCATGGCTGACTAATTTTTTTTATTTATGCAGAGGCCGAGGCCGCCTCGGC

CTCTGAGCTATTCCAGAAGTAGTGAGGAGGCTTTTTTGGAGGCCTAGGCTTTT

GCGTCGAGACGTACCCAATTCGCCCTATAGTGAGTCGTATTACGCGCGCTCA

CTGGCCGTCGTTTTACAACGTCGTGACTGGGAAAACCCTGGCGTTACCCAACT

TAATCGCCTTGCAGCACATCCCCCTTTCGCCAGCTGGCGTAATAGCGAAGAG

GCCCGCACCGATCGCCCTTCCCAACAGTTGCGCAGCCTGAATGGCGAATGGC

GCGACGCGCCCTGTAGCGGCGCATTAAGCGCGGCGGGTGTGGTGGTTACGCG

CAGCGTGACCGCTACACTTGCCAGCGCCCTAGCGCCCGCTCCTTTCGCTTTCT

TCCCTTCCTTTCTCGCCACGTTCGCCGGCTTTCCCCGTCAAGCTCTAAATCGG

GGGCTCCCTTTAGGGTTCCGATTTAGTGCTTTACGGCACCTCGACCCCAAAAA

ACTTGATTAGGGTGATGGTTCACGTAGTGGGCCATCGCCCTGATAGACGGTTT

TTCGCCCTTTGACGTTGGAGTCCACGTTCTTTAATAGTGGACTCTTGTTCCAA

ACTGGAACAACACTCAACCCTATCTCGGTCTATTCTTTTGATTTATAAGGGAT

TTTGCCGATTTCGGCCTATTGGTTAAAAAATGAGCTGATTTAACAAAAATTTA

ACGCGAATTTTAACAAAATATTAACGTTTACAATTTCCCAGGTGGCACTTTTC

GGGGAAATGTGCGCGGAACCCCTATTTGTTTATTTTTCTAAATACATTCAAAT

ATGTATCCGCTCATGAGACAATAACCCTGATAAATGCTTCAATAATATTGAA

AAAGGAAGAGTATGAGTATTCAACATTTCCGTGTCGCCCTTATTCCCTTTTTT

GCGGCATTTTGCCTTCCTGTTTTTGCTCACCCAGAAACGCTGGTGAAAGTAAA

AGATGCTGAAGATCAGTTGGGTGCACGAGTGGGTTACATCGAACTGGATCTC

AACAGCGGTAAGATCCTTGAGAGTTTTCGCCCCGAAGAACGTTTTCCAATGA

TGAGCACTTTTAAAGTTCTGCTATGTGGCGCGGTATTATCCCGTATTGACGCC

GGGCAAGAGCAACTCGGTCGCCGCATACACTATTCTCAGAATGACTTGGTTG

AGTACTCACCAGTCACAGAAAAGCATCTTACGGATGGCATGACAGTAAGAGA

ATTATGCAGTGCTGCCATAACCATGAGTGATAACACTGCGGCCAACTTACTTC

TGACAACGATCGGAGGACCGAAGGAGCTAACCGCTTTTTTGCACAACATGGG

GGATCATGTAACTCGCCTTGATCGTTGGGAACCGGAGCTGAATGAAGCCATA

CCAAACGACGAGCGTGACACCACGATGCCTGTAGCAATGGCAACAACGTTGC

GCAAACTATTAACTGGCGAACTACTTACTCTAGCTTCCCGGCAACAATTAATA

GACTGGATGGAGGCGGATAAAGTTGCAGGACCACTTCTGCGCTCGGCCCTTC

CGGCTGGCTGGTTTATTGCTGATAAATCTGGAGCCGGTGAGCGTGGGTCTCGC

GGTATCATTGCAGCACTGGGGCCAGATGGTAAGCCCTCCCGTATCGTAGTTAT

CTACACGACGGGGAGTCAGGCAACTATGGATGAACGAAATAGACAGATCGC
```

TGAGATAGGTGCCTCACTGATTAAGCATTGGTAACTGTCAGACCAAGTTTACT

CATATATACTTTAGATTGATTTAAAACTTCATTTTTAATTTAAAAGGATCTAG

GTGAAGATCCTTTTTGATAATCTCATGACCAAAATCCCTTAACGTGAGTTTTC

GTTCCACTGAGCGTCAGACCCCGTAGAAAAGATCAAAGGATCTTCTTGAGAT

CCTTTTTTTCTGCGCGTAATCTGCTGCTTGCAAACAAAAAAACCACCGCTACC

AGCGGTGGTTTGTTTGCCGGATCAAGAGCTACCAACTCTTTTTCCGAAGGTAA

CTGGCTTCAGCAGAGCGCAGATACCAAATACTGTCCTTCTAGTGTAGCCGTA

GTTAGGCCACCACTTCAAGAACTCTGTAGCACCGCCTACATACCTCGCTCTGC

TAATCCTGTTACCAGTGGCTGCTGCCAGTGGCGATAAGTCGTGTCTTACCGGG

TTGGACTCAAGACGATAGTTACCGGATAAGGCGCAGCGGTCGGGCTGAACGG

GGGGTTCGTGCACACAGCCCAGCTTGGAGCGAACGACCTACACCGAACTGAG

ATACCTACAGCGTGAGCTATGAGAAAGCGCCACGCTTCCCGAAGGGAGAAA

GGCGGACAGGTATCCGGTAAGCGGCAGGGTCGGAACAGGAGAGCGCACGAG

GGAGCTTCCAGGGGGAAACGCCTGGTATCTTTATAGTCCTGTCGGGTTTCGCC

ACCTCTGACTTGAGCGTCGATTTTTGTGATGCTCGTCAGGGGGGCGGAGCCTA

TGGAAAAACGCCAGCAACGCGGCCTTTTTACGGTTCCTGGCCTTTTGCTGGCC

TTTTGCTCACATGTTCTTTCCTGCGTTATCCCCTGATTCTGTGGATAACCGTAT

TACCGCCTTTGAGTGAGCTGATACCGCTCGCCGCAGCCGAACGACCGAGCGC

AGCGAGTCAGTGAGCGAGGAAGCGGAAGAGCGCCCAATACGCAAACCGCCT

CTCCCCGCGCGTTGGCCGATTCATTAATGCAGCTGGCACGACAGGTTTCCCGA

CTGGAAAGCGGGCAGTGAGCGCAACGCAATTAATGTGAGTTAGCTCACTCAT

TAGGCACCCCAGGCTTTACACTTTATGCTTCCGGCTCGTATGTTGTGTGGAAT

TGTGAGCGGATAACAATTTCACACAGGAAACAGCTATGACCATGATTACGCC

AAGCGCGCAATTAACCCTCACTAAAGGGAACAAAAGCTGGAGCTGCAAGCTT

AATGTAGTCTTATGCAATACTCTTGTAGTCTTGCAACATGGTAACGATGAGTT

AGCAACATGCCTTACAAGGAGAGAAAAAGCACCGTGCATGCCGATTGGTGG

AAGTAAGGTGGTACGATCGTGCCTTATTAGGAAGGCAACAGACGGGTCTGAC

ATGGATTGGACGAACCACTGAATTGCCGCATTGCAGAGATATTGTATTTAAG

TGCCTAGCTCGATACAATAAACGGGTCTCTCTGGTTAGACCAGATCTGAGCCT

GGGAGCTCTCTGGCTAACTAGGGAACCCACTGCTTAAGCCTCAATAAAGCTT

GCCTTGAGTGCTTCAAGTAGTGTGTGCCCGTCTGTTGTGTGACTCTGGTAACT

AGAGATCCCTCAGACCCTTTTAGTCAGTGTGGAAAATCTCTAGCAGTGGCGC

CCGAACAGGGACCTGAAAGCGAAAGGGAAACCAGAGCTCTCTCGACGCAGG

ACTCGGCTTGCTGAAGCGCGCACGGCAAGAGGCGAGGGGCGGCGACTGGTG

AGTACGCCAAAAATTTTGACTAGCGGAGGCTAGAAGGAGAGAGATGGGTGC

GAGAGCGTCAGTATTAAGCGGGGGAGAATTAGATCGCGATGGGAAAAAATT

CGGTTAAGGCCAGGGGGAAAGAAAAAATATAAATTAAAACATATAGTATGG

GCAAGCAGGGAGCTAGAACGATTCGCAGTTAATCCTGGCCTGTTAGAAACAT

CAGAAGGCTGTAGACAAATACTGGGACAGCTACAACCATCCCTTCAGACAGG

ATCAGAAGAACTTAGATCATTATATAATACAGTAGCAACCCTCTATTGTGTGC

ATCAAAGGATAGAGATAAAAGACACCAAGGAAGCTTTAGACAAGATAGAGG

-continued

```
AAGAGCAAAACAAAAGTAAGACCACCGCACAGCAAGCGGCCGCTGATCTTC

AGACCTGGAGGAGGAGATATGAGGGACAATTGGAGAAGTGAATTATATAAA

TATAAAGTAGTAAAAATTGAACCATTAGGAGTAGCACCCACCAAGGCAAAG

AGAAGAGTGGTGCAGAGAGAAAAAAGAGCAGTGGGAATAGGAGCTTTGTTC

CTTGGGTTCTTGGGAGCAGCAGGAAGCACTATGGGCGCAGCCTCAATGACGC

TGACGGTACAGGCCAGACAATTATTGTCTGGTATAGTGCAGCAGCAGAACAA

TTTGCTGAGGGCTATTGAGGCGCAACAGCATCTGTTGCAACTCACAGTCTGG

GGCATCAAGCAGCTCCAGGCAAGAATCCTGGCTGTGGAAAGATACCTAAAGG

ATCAACAGCTCCTGGGGATTTGGGGTTGCTCTGGAAAACTCATTTGCACCACT

GCTGTGCCTTGGAATGCTAGTTGGAGTAATAAATCTCTGGAACAGATTGGAA

TCACACGACCTGGATGGAGTGGGACAGAGAAATTAACAATTACACAAGCTTA

ATACACTCCTTAATTGAAGAATCGCAAAACCAGCAAGAAAAGAATGAACAA

GAATTATTGGAATTAGATAAATGGGCAAGTTTGTGGAATTGGTTTAACATAA

CAAATTGGCTGTGGTATATAAAATTATTCATAATGATAGTAGGAGGCTTGGT

AGGTTTAAGAATAGTTTTTGCTGTACTTTCTATAGTGAATAGAGTTAGGCAGG

GATATTCACCATTATCGTTTCAGACCCACCTCCCAACCCCGAGGGGACCCGA

CAGGCCCGAAGGAATAGAAGAAGAAGGTGGAGAGAGAGACAGAGACAGAT

CCATTCGATTAGTGAACGGATCTCGACGGTATCGATTAGACTGTAGCCCAGG

AATATGGCAGCTAGATTGTACACATTTAGAAGGAAAAGTTATCTTGGTAGCA

GTTCATGTAGCCAGTGGATATATAGAAGCAGAAGTAATTCCAGCAGAGACAG

GGCAAGAAACAGCATACTTCCTCTTAAAATTAGCAGGAAGATGGCCAGTAAA

AACAGTACATACAGACAATGGCAGCAATTTCACCAGTACTACAGTTAAGGCC

GCCTGTTGGTGGGCGGGGATCAAGCAGGAATTTGGCATTCCCTACAATCCCC

AAAGTCAAGGAGTAATAGAATCTATGAATAAAGAATTAAAGAAAATTATAG

GACAGGTAAGAGATCAGGCTGAACATCTTAAGACAGCAGTACAAATGGCAG

TATTCATCCACAATTTTAAAAGAAAAGGGGGGATTGGGGGGTACAGTGCAGG

GGAAAGAATAGTAGACATAATAGCAACAGACATACAAACTAAAGAATTACA

AAAACAAATTACAAAAATTCAAAATTTTCGGGTTTATTACAGGGACAGCAGA

GATCCAGTTTGGCTGCATACGCGTCGTGAGGCTCCGGTGCCCGTCAGTGGGC

AGAGCGCACATCGCCCACAGTCCCCGAGAAGTTGGGGGGAGGGGTCGGCAA

TTGAACCGGTGCCTAGAGAAGGTGGCGCGGGGTAAACTGGGAAAGTGATGTC

GTGTACTGGCTCCGCCTTTTTCCCGAGGGTGGGGGAGAACCGTATATAAGTG

CAGTAGTCGCCGTGAACGTTCTTTTTCGCAACGGGTTTGCCGCCAGAACACAG

GTAAGTGCCGTGTGTGGTTCCCGCGGGCCTGGCCTCTTTACGGGTTATGGCCC

TTGCGTGCCTTGAATTACTTCCACCTGGCTGCAGTACGTGATTCTTGATCCCG

AGCTTCGGGTTGGAAGTGGGTGGGAGAGTTCGAGGCCTTGCGCTTAAGGAGC

CCCTTCGCCTCGTGCTTGAGTTGAGGCCTGGCCTGGGCGCTGGGGCCGCCGC

GTGCGAATCTGGTGGCACCTTCGCGCCTGTCTCGCTGCTTTCGATAAGTCTCT

AGCCATTTAAAATTTTTGATGACCTGCTGCGACGCTTTTTTTCTGGCAAGATA

GTCTTGTAAATGCGGGCCAAGATCTGCACACTGGTATTTCGGTTTTTGGGGCC
```

-continued

GCGGGCGGCGACGGGGCCCGTGCGTCCCAGCGCACATGTTCGGCGAGGCGG

GGCCTGCGAGCGCGGCCACCGAGAATCGGACGGGGGTAGTCTCAAGCTGGC

CGGCCTGCTCTGGTGCCTGGCCTCGCGCCGCCGTGTATCGCCCCGCCCTGGGC

GGCAAGGCTGGCCCGGTCGGCACCAGTTGCGTGAGCGGAAAGATGGCCGCTT

CCCGGCCCTGCTGCAGGGAGCTCAAAATGGAGGACGCGGCGCTCGGGAGAG

CGGGCGGGTGAGTCACCCACACAAAGGAAAAGGGCCTTTCCGTCCTCAGCCG

TCGCTTCATGTGACTCCACGGAGTACCGGGCGCCGTCCAGGCACCTCGATTA

GTTCTCGAGCTTTTGGAGTACGTCGTCTTTAGGTTGGGGGGAGGGGTTTTATG

CGATGGAGTTTCCCCACACTGAGTGGGTGGAGACTGAAGTTAGGCCAGCTTG

GCACTTGATGTAATTCTCCTTGGAATTTGCCCTTTTTGAGTTTGGATCTTGGTT

CATTCTCAAGCCTCAGACAGTGGTTCAAAGTTTTTTTCTTCCATTTCAGGTGTC

GTGAGCTAGCTCTAGAG

NKG2D_CD3Zeta CAR nucleic acid sequence (SEQ ID NO: 18)

TTCAACCAAGAAGTTCAAATTCCCTTGACCGAAAGTTACTGTGGCCCATGTCC

TAAAAACTGGATATGTTACAAAAATAACTGCTACCAATTTTTTGATGAGAGT

AAAAACTGGTATGAGAGCCAGGCTTCTTGTATGTCTCAAAATGCCAGCCTTCT

GAAAGTATACAGCAAAGAGGACCAGGATTTACTTAAACTGGTGAAGTCATAT

CATTGGATGGGACTAGTACACATTCCAACAAATGGATCTTGGCAGTGGGAAG

ATGGCTCCATTCTCTCACCCAACCTACTAACAATAATTGAAATGCAGAAGGG

AGACTGTGCACTCTATGCCTCGAGCTTTAAAGGCTATATAGAAAACTGTTCAA

CTCCAAATACGTACATCTGCATGCAAAGGACTGTGGCTAGCACCACGACGCC

AGCGCCGCGACCACCAACACCGGCGCCCACCATCGCGTCGCAGCCCCTGTCC

CTGCGCCCAGAGGCGTGCCGGCCAGCGGCGGGGGCGCAGTGCACACGAGG

GGGCTGGACTTCGCCTGTGATATCTACATCTGGGCGCCCTTGGCCGGGACTTG

TGGGGTCCTTCTCCTGTCACTGGTTATCACCCTTTACTGCAGAGTGAAGTTCA

GCAGGAGCGCAGACGCCCCCGCGTACCAGCAGGGCCAGAACCAGCTCTATA

ACGAGCTCAATCTAGGACGAAGAGAGGAGTACGATGTTTTGGACAAGAGAC

GTGGCCGGGACCCTGAGATGGGGGGAAAGCCGAGAAGGAAGAACCCTCAGG

AAGGCCTGTACAATGAACTGCAGAAAGATAAGATGGCGGAGGCCTACAGTG

AGATTGGGATGAAAGGCGAGCGCCGGAGGGGCAAGGGGCACGATGGCCTTT

ACCAGGGTCTCAGTACAGCCACCAAGGACACCTACGACGCCCTTCACATGCA

GGCCCTGCCCCCTCGC

NKG2D_CD3Zeta CAR amino acid sequence (SEQ ID NO: 19)

FNQEVQIPLTESYCGPCPKNWICYKNNCYQFFDESKNWYESQASCMSQNASLLK

VYSKEDQDLLKLVKSYHWMGLVHIPTNGSWQWEDGSILSPNLLTIIEMQKGDCA

LYASSFKGYIENCSTPNTYICMQRTVASTTTPAPRPPTPAPTIASQPLSLRPEACRP

AAGGAVHTRGLDFACDIYIWAPLAGTCGVLLLSLVITLYCRVKFSRSADAPAYQ

US 12,624,085 B2

67                                                                68

-continued

QGQNQLYNELNLGRREEYDVLDKRRGRDPEMGGKPRRKNPQEGLYNELQKDK

MAEAYSEIGMKGERRRGKGHDGLYQGLSTATKDTYDALHMQALPPR

The results of the experiments are now described.

Example 1: Expression of NKG2D Ligands on
TNBC Cell Lines

Figures 7A, 7B:
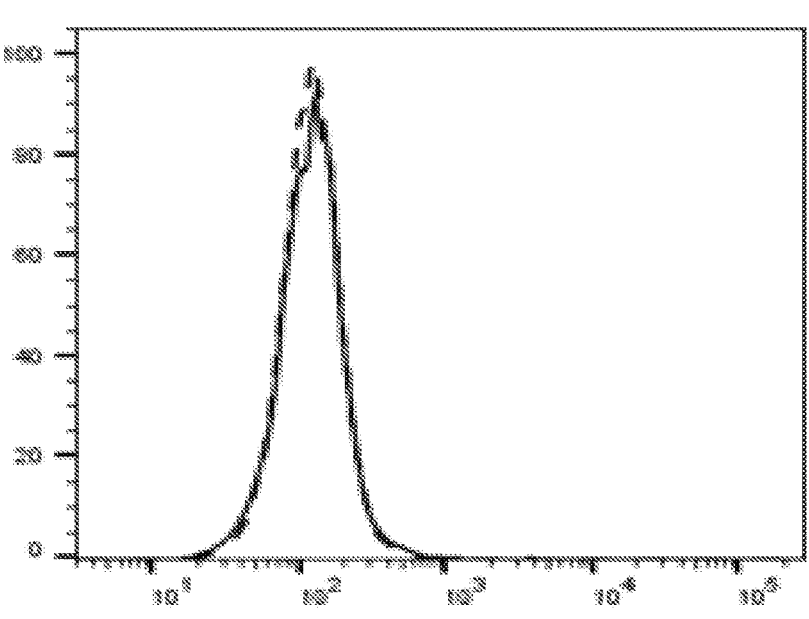
FIGS. 7A-7C are series of graphs and an image depicting NKG2D CAR expression in the presence or absence of IL-2.

To investigate NKG2DLs expression in human TNBC, five TNBC cell lines were screened for the NKG2DLs expression via flow cytometry using a recombinant NKG2D receptor-human IgG1-Fc fusion protein that recognizes all ligands for this receptor. The majority of lines bound the NKG2D-Fc protein and expressed a high to moderate level of NKG2DLs, except for BT549; a lower level of NKG2D-Fc protein binding was detected on MDA-MB-453 cells. (FIG. 1). AE17, a mouse malignant mesothelioma cell line (Song D-G et al., Human gene therapy. 2013; 24(3):295-305), served as a negative control and did not express detectable human NKG2DLs (FIG. 7A). Next the expression distribution of the individual NKG2DL family members was examined in TNBC cell lines by flow cytometry, using antibodies specific for ICA/B, or ULBP-1, -2/5/6, -3, or -4 (FIG. 1). Although varied in level of expression, all TNBC cell lines tested expressed one or more cell surface NKG2DLs. BT549 nearly exclusively expressed surface ICA/B and at high level, while a low level of ICA/B was detected on MDA-MB-436 cells. All other TNBC lines were ICA/B negative. The expression of the ULBPs on TNBC cell lines varied: ULBP1 was only expressed on MDA-MB-468 at low levels, while ULBP-2/5/6 were more often strongly expressed in all TNBC cell lines except for BT549; ULBP-3 and 4 were only found on the MDA-453 and MDA-MB-231, respectively. The breast cancer cell line MCF-7 expressed various NKG2DLs which was previously characterized (Zhang et al., Cancer Research. 2006; 66(11): 5927-5933; Kim et al., Journal of Immunotherapy. 2008; 31(5):475-486) was used as a positive control. Together, NKG2DLs appear to be broadly expressed by TNBC cell lines, although some cell lines display a relatively low level of ligand expression.

Example 2: NKG2D CAR Design and Surface
Expression on T Cells

Figure 2A:
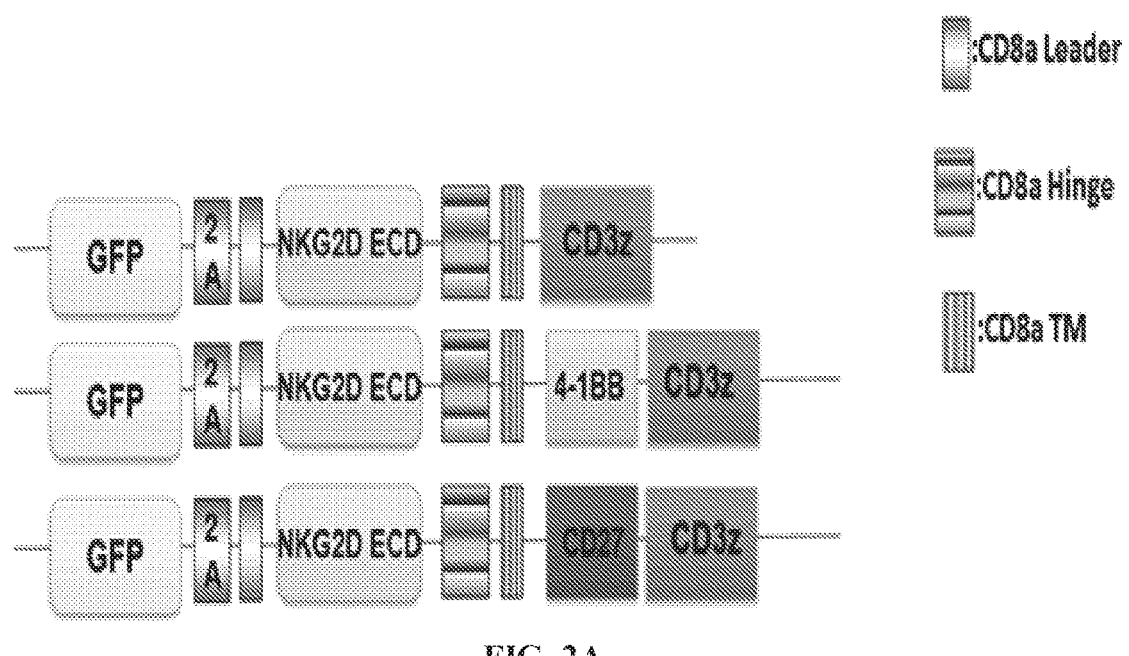
FIG. 2A-2B are a diagram and series of graphs depicting the NKG2D CAR constructs of the invention and their expression.
Figure 2B:
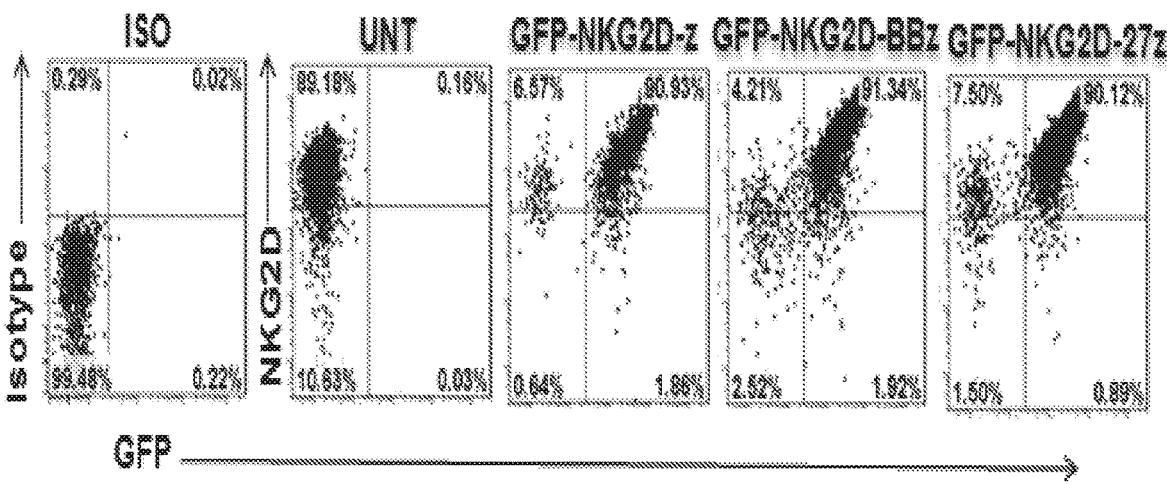

NKG2D CARs were developed consisting of the extracellular portion of the human NKG2D receptor linked to a CD8a hinge and transmembrane region, followed by a CD3z signaling moiety alone (GFP-NKG2D-z) or in tandem with the 4-1BB (GFP-NKG2D-BBz) or CD27 (GFP-NKG2D-27z) intracellular signaling motif (FIG. 2A). Bicistronic expression vectors incorporating a 2A peptide sequence permitted dual expression analysis of GFP and the NKG2D CAR (FIG. 2B). Cultures of GFP-NKG2D-z, -27z as well as -BBz CAR T cells were highly enriched for CAR+ GFP+ T cells (~90%) at the end of two weeks expansion in the presence of IL-2 (50 IU/ml) (FIG. 2B). Based on these results, GFP was used as a surrogate marker for detection of engineered NKG2D CAR T cells in the following experiments.

Figure 3A:
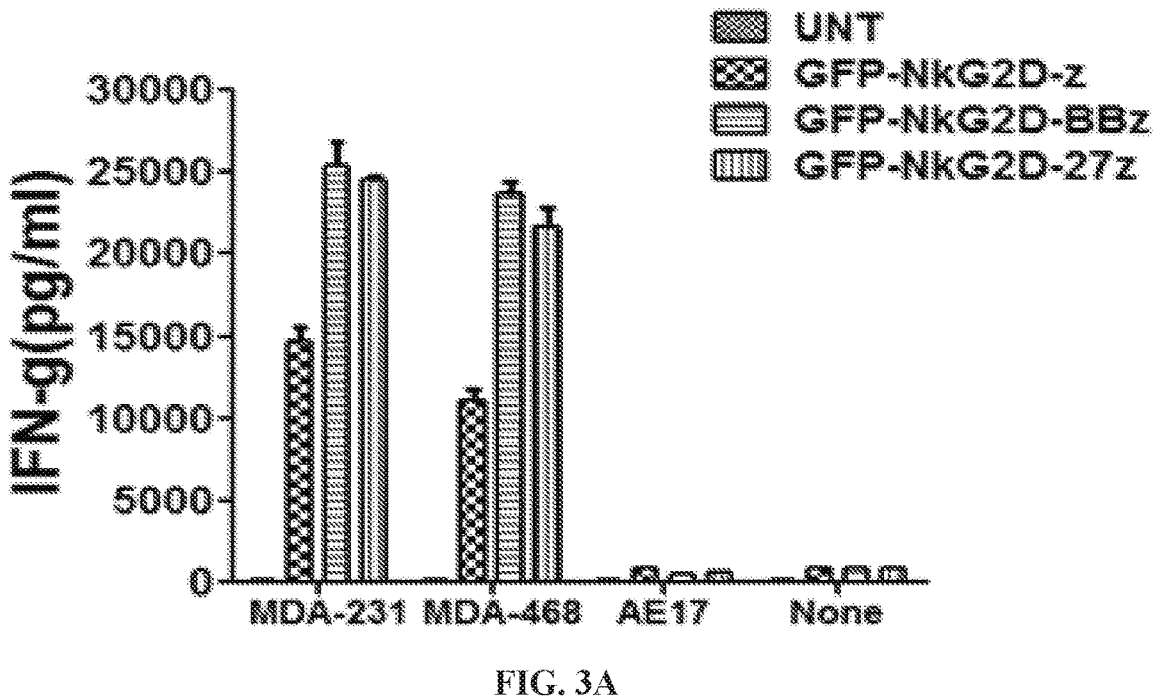
FIGS. 3A-3D are series of graphs demonstrating the recognition of human TNBC cells by NKG2D CAR T cells in vitro.

Example 3: NKG2D CAR T Cells Effectively
Recognize and Eliminate TNBC Cell Lines In Vitro To evaluate the antitumor function of NKG2D CAR-T cells in vitro, primary human T cells and TNBC cells were co-cultured and CAR T-cell reactivity measured by proinflammatory cytokine secretion. NKG2D CAR-T cells recognized TNBC cell lines MDA-MB-231 and MDA-MB-468 and secreted high levels of IFN-γ, but not when stimulated with the NKG2DLs (−) cell line AE17 (FIG. 3A), illustrating the requirement for antigen specificity for CAR-T cell activity. Invariably, increased quantities of secreted IFN-γ were detected when NKG2D-27z and -BBz CAR-T cells where stimulated with the NKG2DLs(+) target cells, relative to first generation NKG2D-z CAR T cells (FIG. 3A).

Figure 3B:
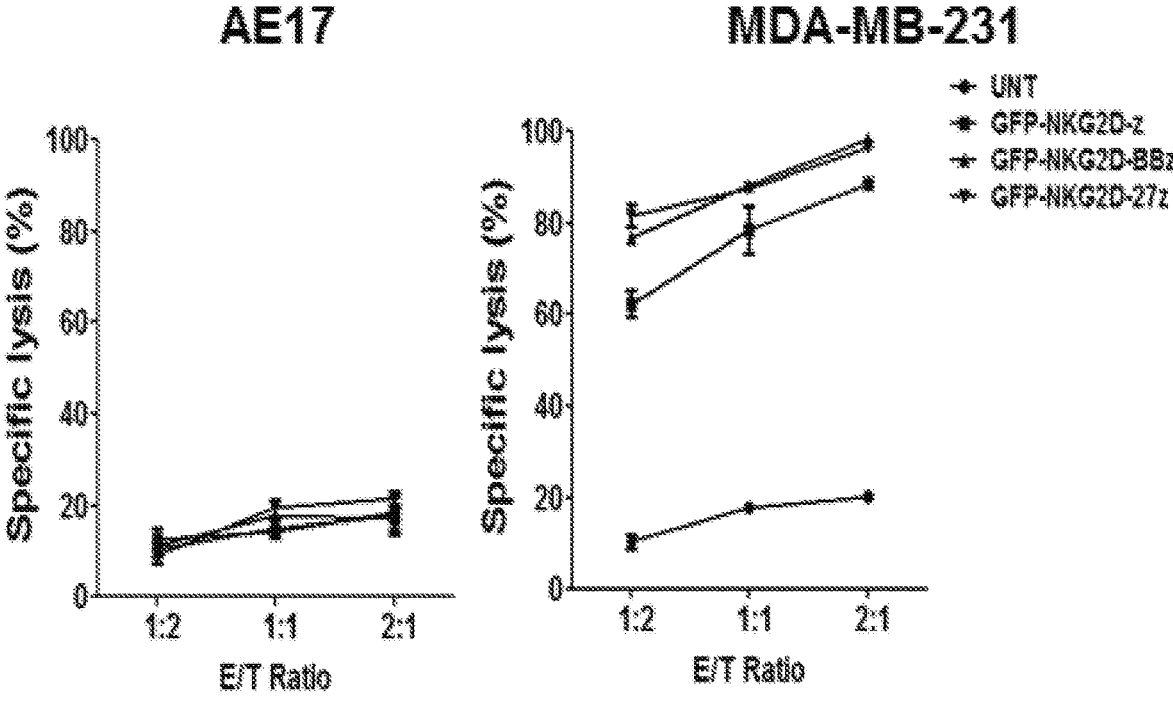

Next, the cytotoxicity of NKG2D CAR T cells was evaluated against the NKG2DLs (+) TNBC cell line, MDA-MB-231fluc, using an overnight luminescence based assay. Compared to control untransduced T cells, NKG2D CARs T cells demonstrated significant cytotoxicity against firefly luciferase (fLuc) expressing MDA-MB-231 cells. When the E:T ratio was as low as 1:2, the cytotoxicity was more than 60% and increased as the E:T ratio increased (FIG. 3B). The NKG2DLs(−) cell line AE17 fLuc was not lysed by NKG2D CAR T cells. Similar to cytokine production results, costimulated NKG2D-BBz or -27z CAR-T cells demonstrated enhanced cytotoxicity compared to their first-generation counterparts (FIG. 3B).

Figure 3C:
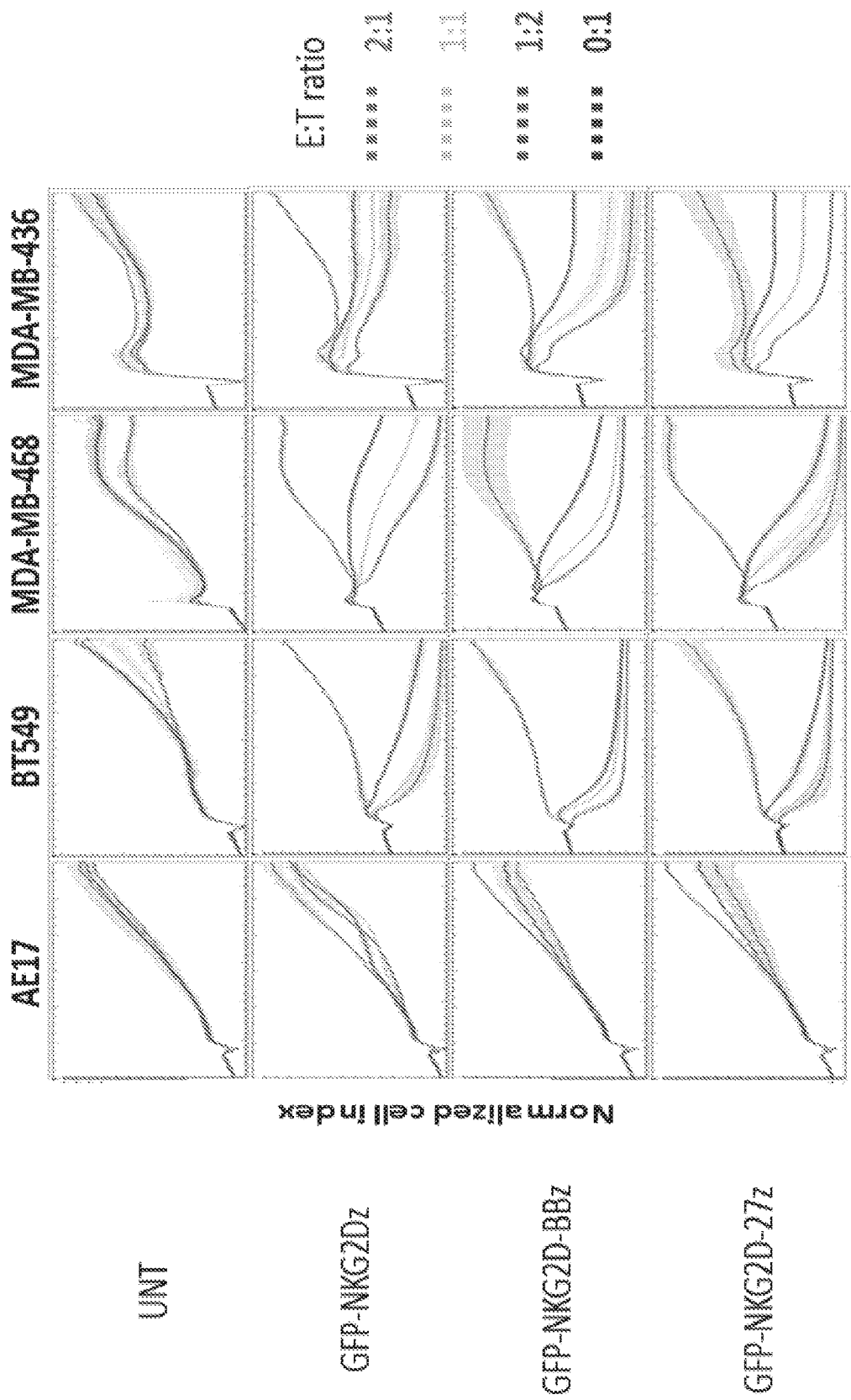
Figure 3D:
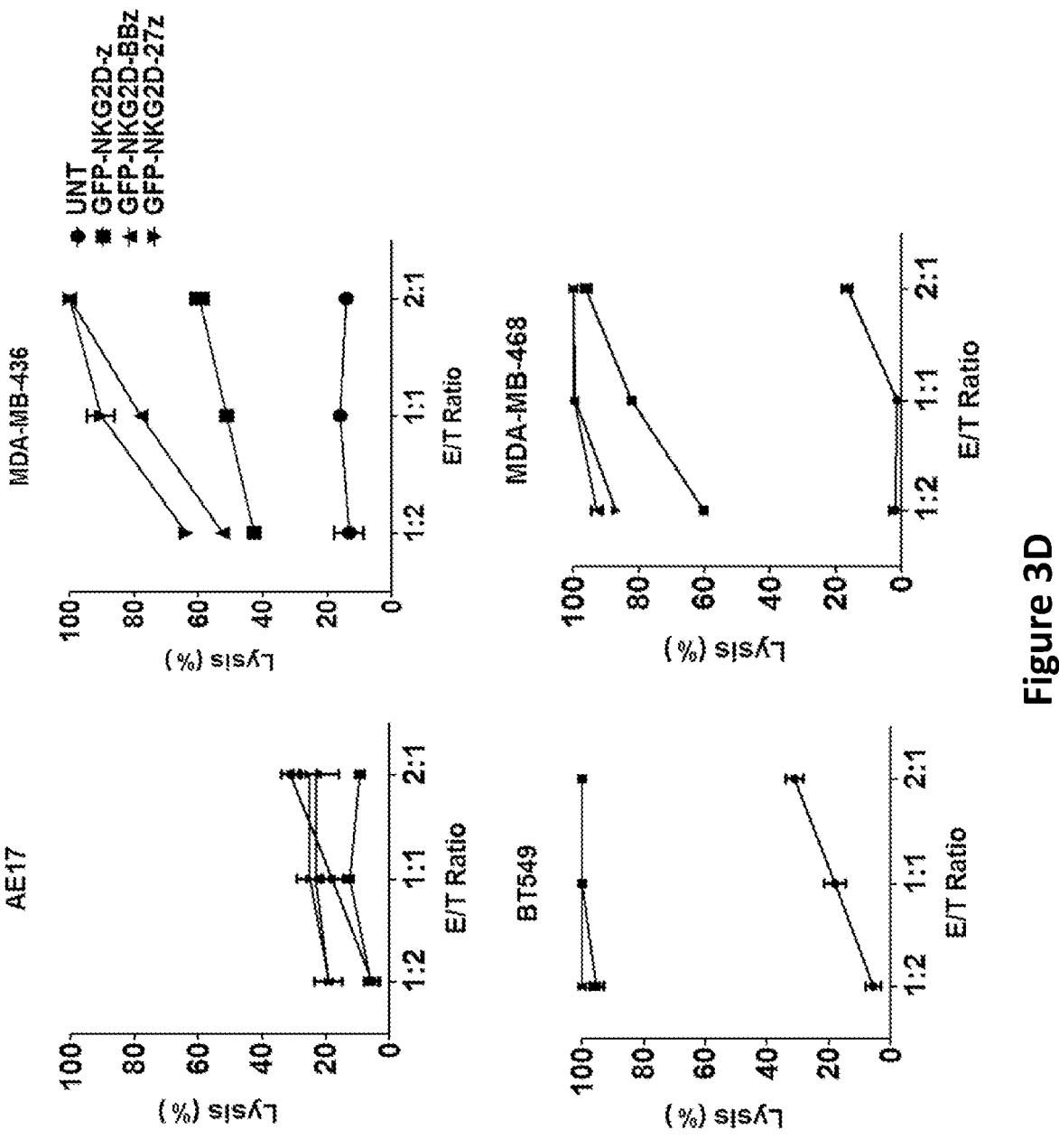

Similarly, xCELLigence cytotoxic data showed that 4-1BB or CD27 costimulated NKG2D CAR-T cells were cytotoxic toward NKG2DLs (+) MDA-MB-468, MDA-MB-436 cells in a time- and E:T ratio-dependent manner, while untransduced T cells did not inhibit the growth of these cells (FIG. 3C). As expected, NKG2D-z CAR T cells were less efficient in killing NKG2DLs (+) target cells and required higher E/T ratios to achieve efficient response (FIGS. 3 C-3D). Interestingly, after 24 hours of co-culture, addition of any iteration of NKG2D CART cells caused BT549 cells to detach from the culture plate, consequently reducing cell index value, suggested BT459 cells were lysed efficiently even at low 1:1 E/T ratio (FIGS. 3C-3D), although these cells only express MIC A/B but no detectable expression of NKG2DLs measured by NKG2D-Fc (FIG. 1). This further suggests that BT549 cells may be more sensitive than MDA-MB-436 and MDA-MB-438 cells to cytolysis by CAR T cells. Similar to the luciferase release-based cytotoxicity assays, the NKG2DLs (−) cell line AE17 was not lysed by NKG2D CAR T cells (FIGS. 3 C-3D).

Figure 4A:
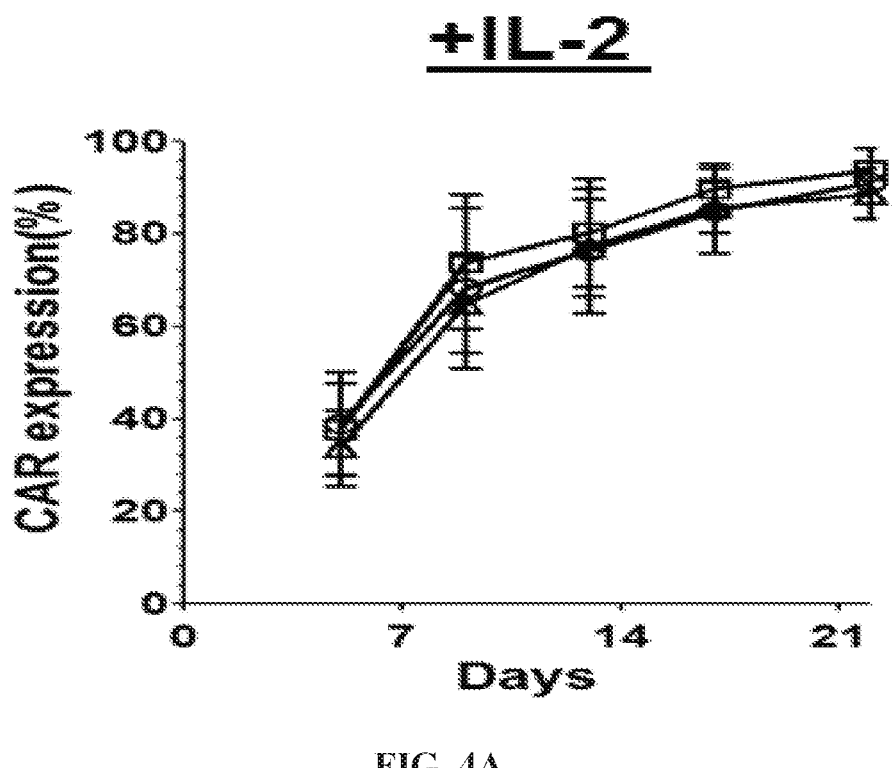
FIGS. 4A-4C are series of graphs demonstrating the NKG2D CAR (GFP) expression on T cells in the presence and absence of IL-2. Percentages of NKG2D CAR (GFP+) cells, presented as the mean±SD were derived from three independent donors during a 3-week culture period in the presence of IL-2 (50 IU/ml) (FIG. 4A) or absence of IL-2 (FIG. 4B). The kinetic monitoring of GFP (NKG2D CAR) expression on one representative donor of three in the presence or absence of IL-2 (FIG. 4C).
Figure 4B:
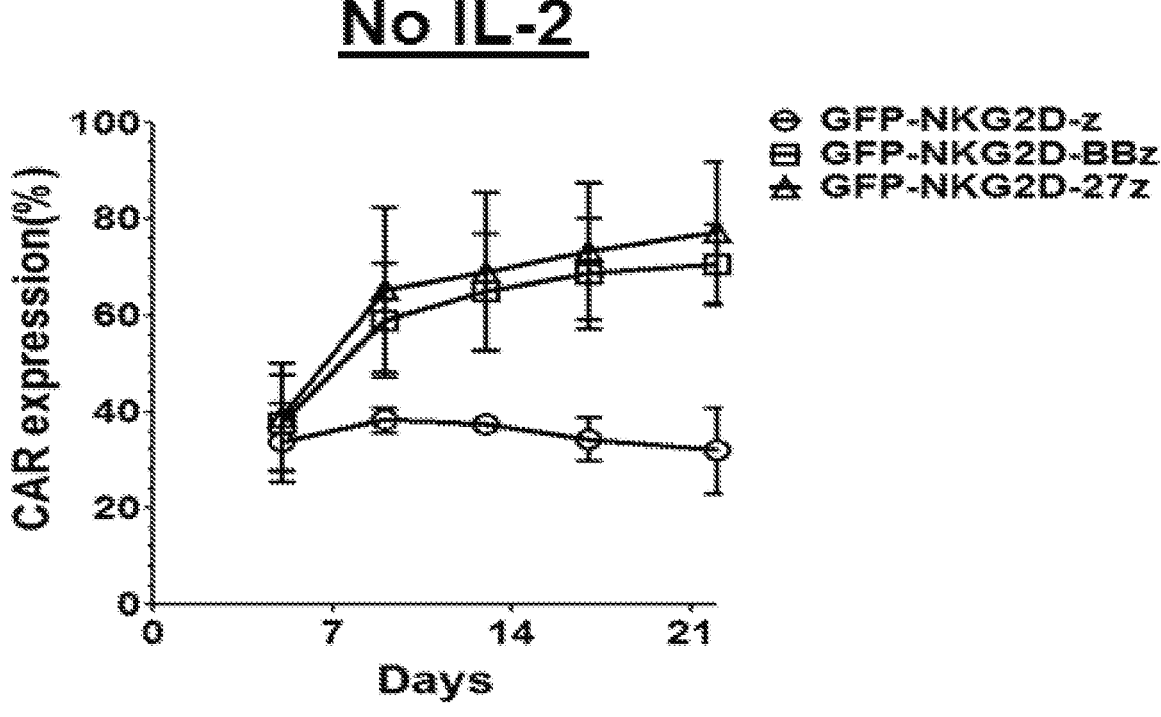
Figure 4C:
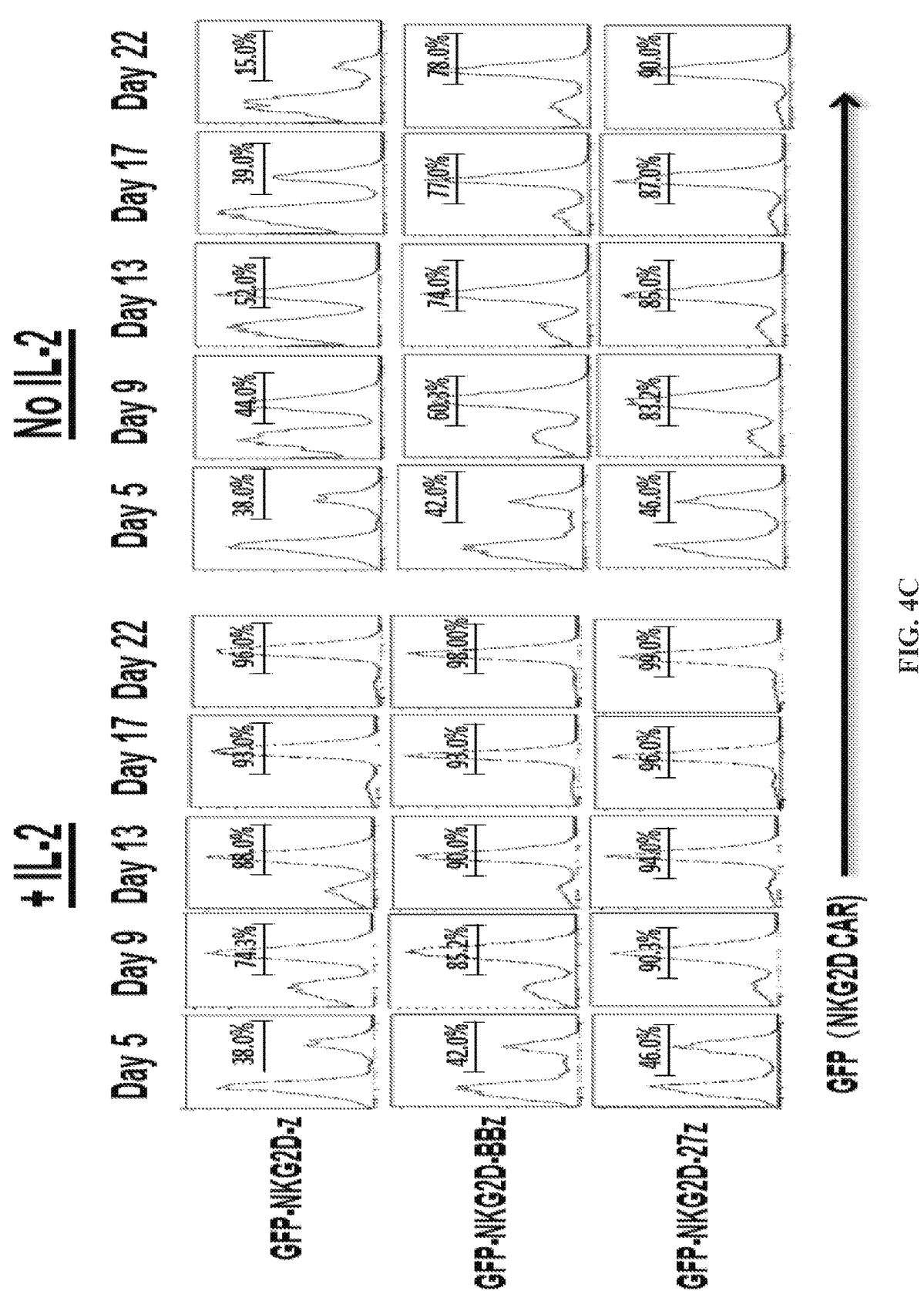
Figure 7C:
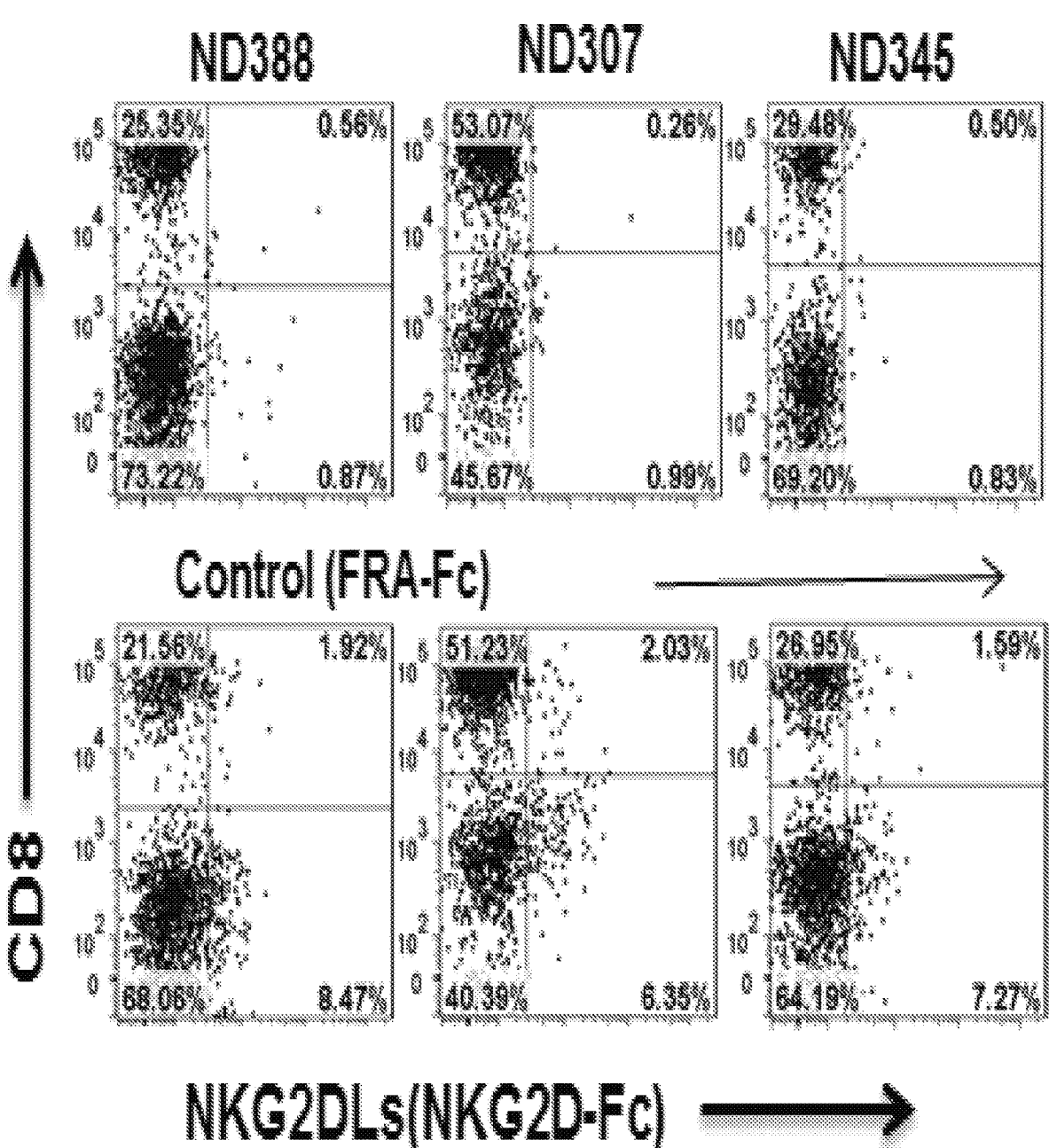
Figure 7D:
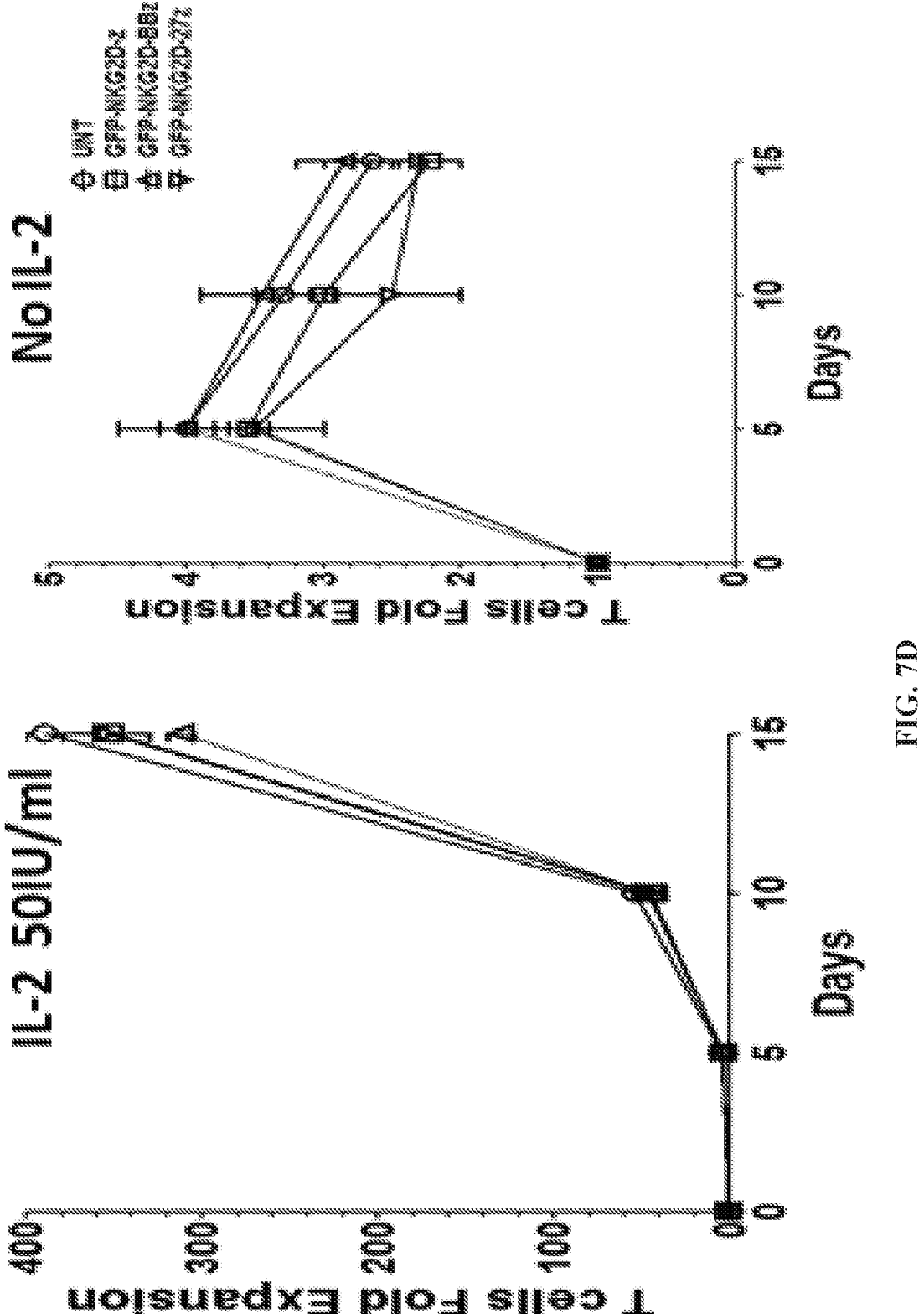
FIG. 7D: T cell-expansion folds in the presence of IL-2 (50 IU/ml) or absence of IL-2.

Example 4: IL-2 Promotes Expansion and
Enrichment of NKG2D-Redirected CAR T Cells During the culture of NKG2D CAR T cells in the presence of IL-2, the temporal enrichment of both the first and second generation of NKG2D CARs was consistently observed, with the frequencies of CAR+ T cells increasing temporally. To investigate the influence of IL-2 on this NKG2D CAR enrichment phenomenon, CAR T cells were washed free of IL-2 using PBS on day 5 after activation and transduction, and then cultured in complete medium in the presence or absence of exogenous IL-2 (50 IU/ml). CAR T-cell count and expression level was monitored for additional two weeks (FIG. 7B). Consistently, in this assay from 3 different donors whose untransduced T cells express NKG2DLs when activated by anti-CD3/28 beads (FIG. 7C), GFP-expressing NKG2D-z, -BBz and -27z CAR T cells expanded more than 300-fold (FIG. 7D) and were highly enriched for CAR+ cells during prolonged culture in the presence of IL-2 (FIG. 4A). Only ~30% of T cells were positive for GFP expression on day 5, but were preferentially enriched to more than 95% GFP+ after an additional two weeks of culture (FIG. 4A). In stark contrast, in the absence of IL-2, NKG2D CAR T cells did not expand well (FIG. 7D) and only T cells that expressed the costimulated GFP-NKG2D-BBz and -27z CARs were still highly enriched for CAR+ cells. In contrast, the frequency of GFP-NKG2D-z CAR T-cells remained stable at ~30% over this entire time, suggesting that a costimulatory signal may be required for CAR enrichment in the absence of IL-2. The kinetic monitoring of surface CAR expression on one representative donor in the presence or absence of IL-2 is shown in FIG. 4C.

Example 5: CD25 High Expression on First Generation NKG2D CAR T Cells is Essential for CAR Enrichment in the Presence of IL-2

Figure 5A:
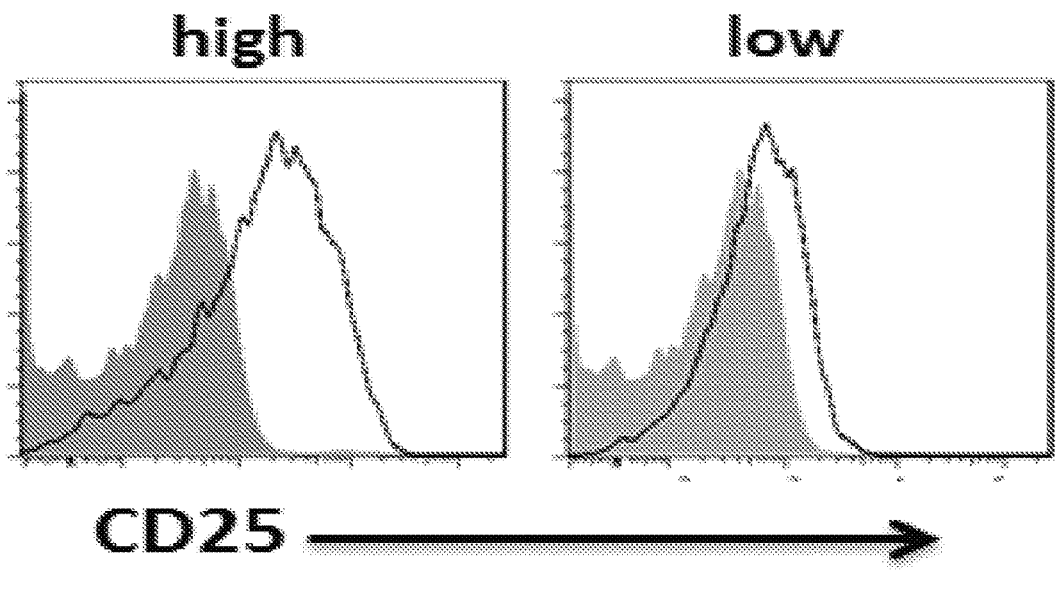
FIGS. 5A-5C are series of graphs showing that the CD25 high expression on GFP-NKG2D-z CAR T cells is essential for enrichment in the presence of IL-2.
Figure 5B:
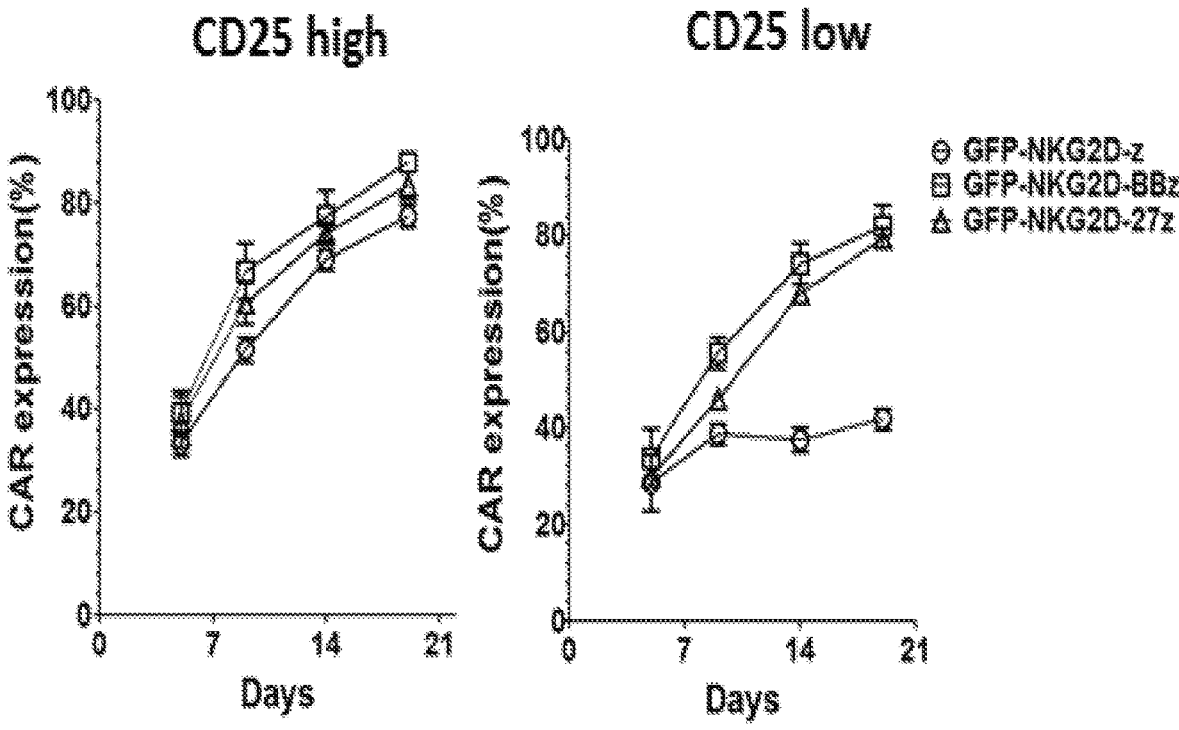
Figure 5C:
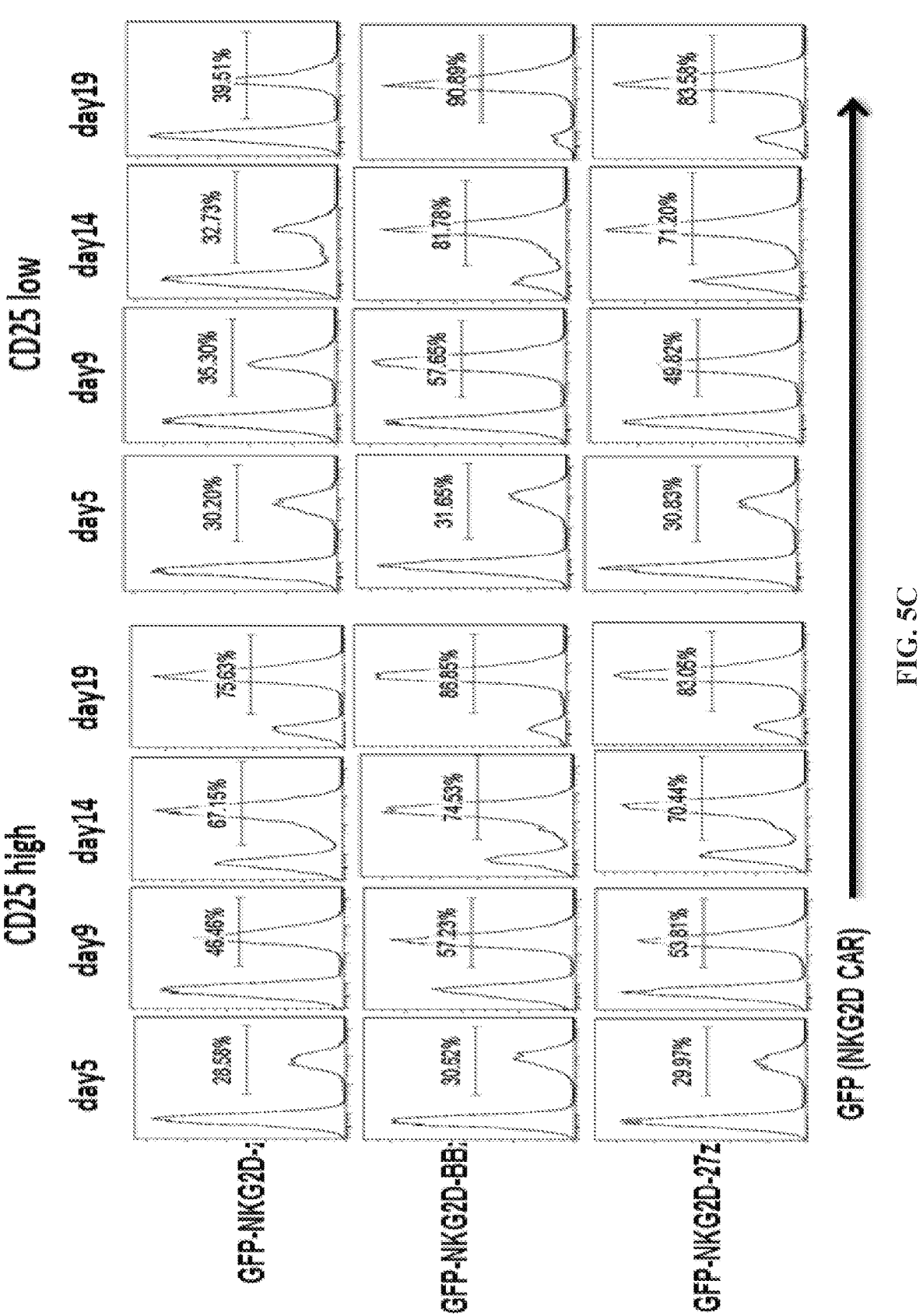

It was previously shown that the enrichment of CAR may be due to the "T-cell fratricide" of the 4-BB costimulated NKG2D CAR T cells interacting with NKG2DLs expressed on activated T cells (Song D-G et al., Human gene therapy. 2013; 24(3):295-305). However, in the presence of IL-2, the first generation NKG2D-z CAR was also highly enriched for CAR (+) cells during culture in vitro. This result suggested that IL-2 stimulation may promote the CAR T cells expansion and upregulate NKG2DLs to enrich NKG2D CAR T cells even without costimulation. To test this hypothesis, the association between CD25 (IL-2 receptor-alpha chain) expression and NKG2D CAR enrichment was investigated. On day 5 after activation, four days post transduction, nearly all of NKG2D CAR+ T cell population expressed a high level of CD25 (FIG. 5A, left). All NKG2D-z, -BBz and -27z CAR T cells that expressed high levels of CD25 were preferentially enriched to ~80% after an additional 14 days of culture (FIG. 5B, left). Next, $CD25^{low}$ NKG2D-z, -BBz and -27z CAR T cells were separated out the by depleting human CD25+ cells by magnetic separation 4 days post transduction (FIG. 5A, right). NKG2D-BBz and -27z CAR T cells that were $CD25^{low}$ were still ~80% enriched after additional 14 days culture in the presence of IL-2 (FIG. 5B, right). Alternatively, NKG2D-z CAR T cell expression frequency in the $CD25^{low}$ population ranged between 30%~40%, which was substantially lower than costimulated NKG2D CAR expression, suggesting that high CD25 expression is essential for IL-2-driven NKG2D CAR enrichment in the absence of costimulatory signal domains, and that the CAR costimulatory domains are sufficient to drive NKG2D CAR enrichment even when surface CD25 expression levels are low. The kinetics of CAR expression in T cells with $CD25^{high}$ or $CD25^{low}$ expression in the presence of IL-2 is shown for one representative donor (FIG. 5C).

Figure 8A:
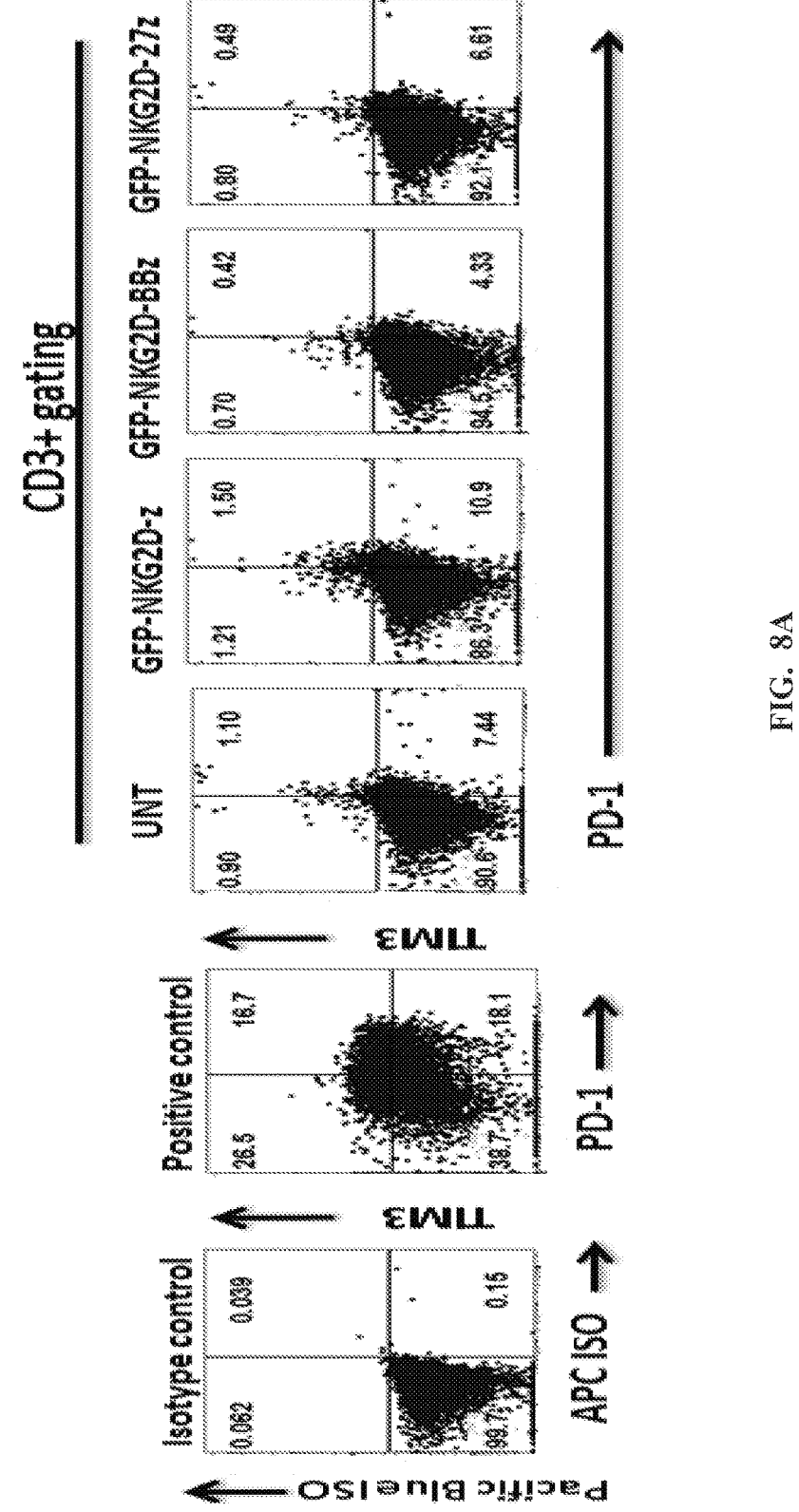
FIGS. 8A-8B are series of flow cytometry graphs depicting the expression of PD-1, TIM-3 and CD137 markers in T cells.
Figure 8B:
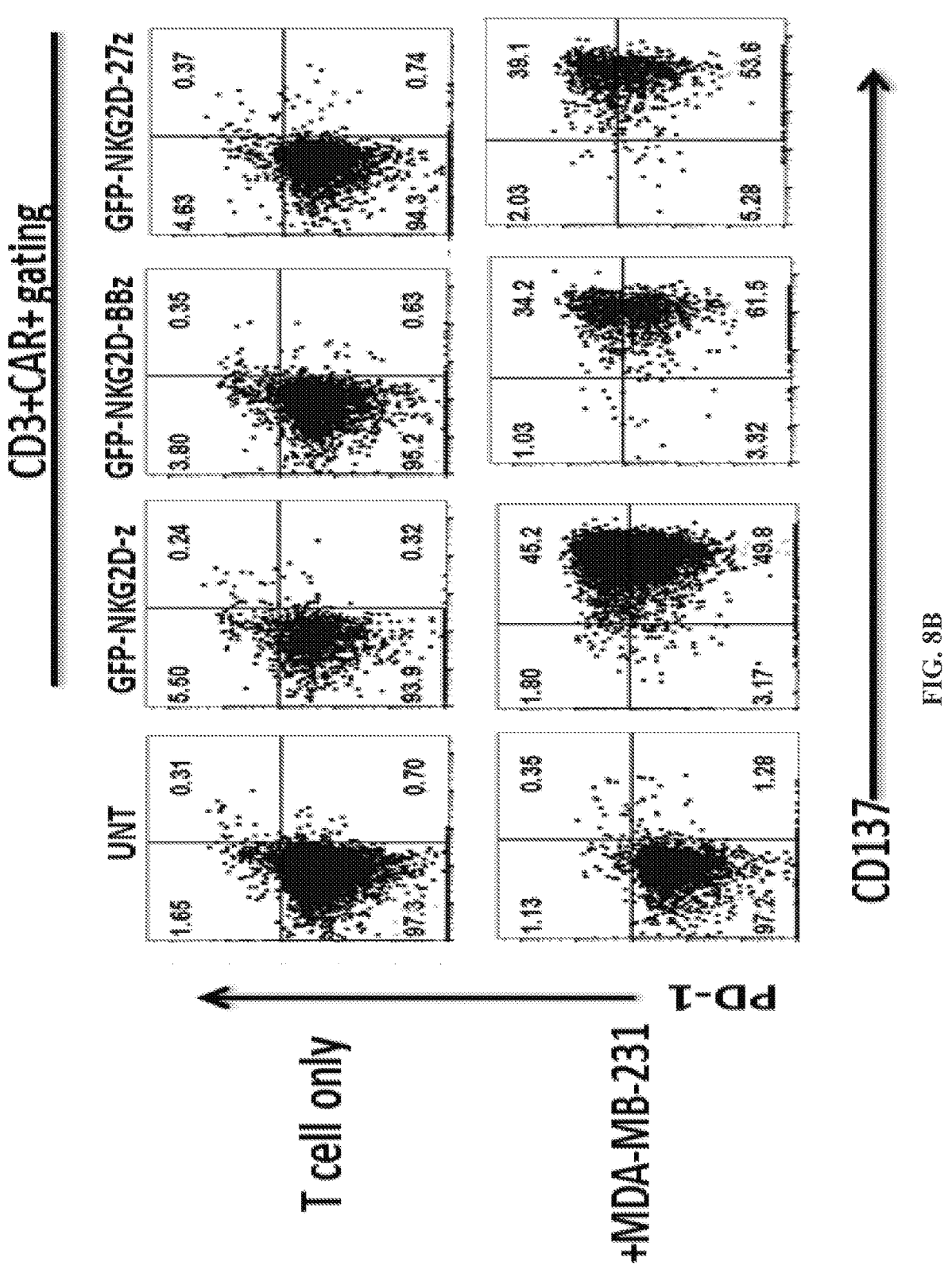
Figure 9:
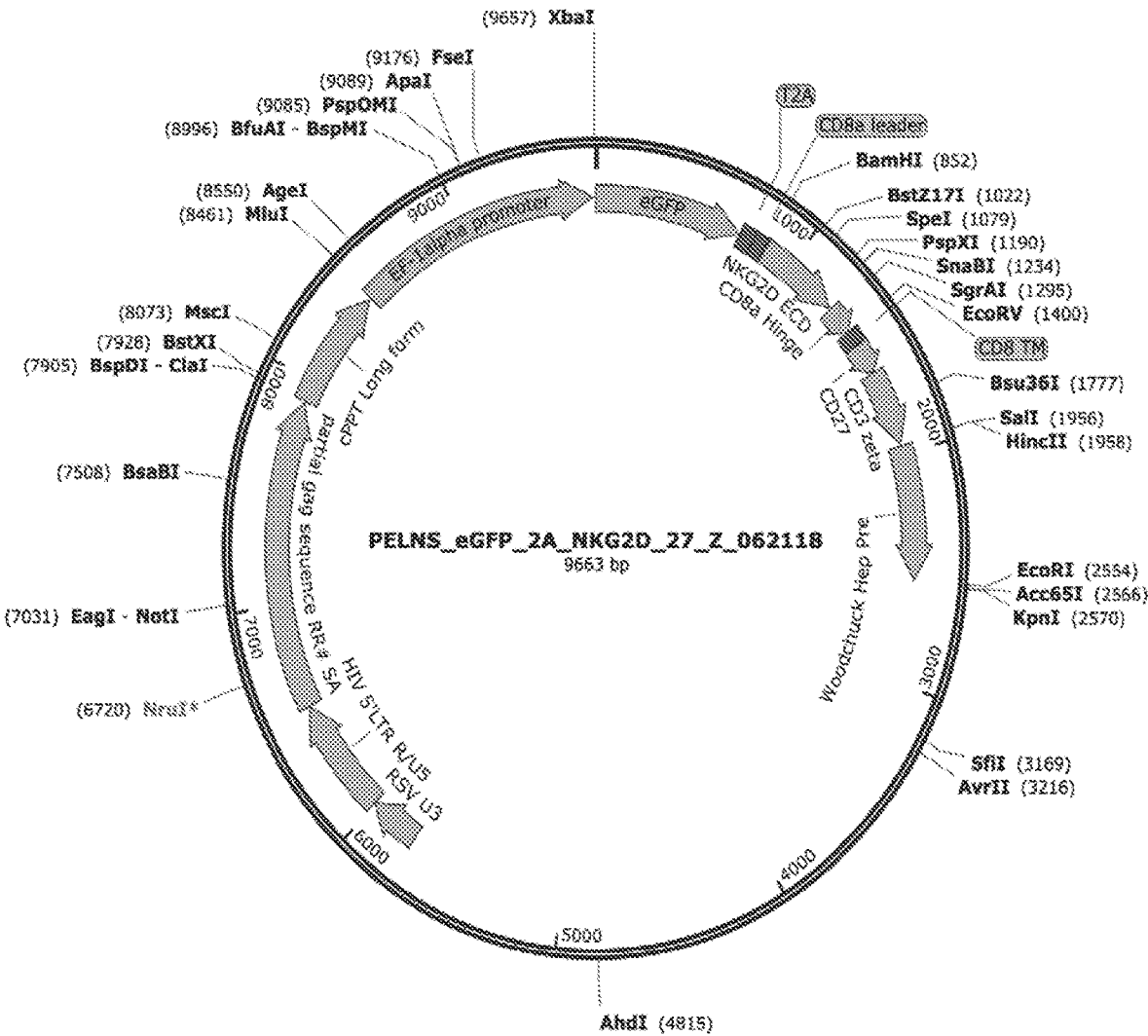
FIG. 9 is a map of vector PELNS_eGFP_2A_NKG2D_CD27_CD3Zeta (SEQ ID NO: 1).
Figure 10:
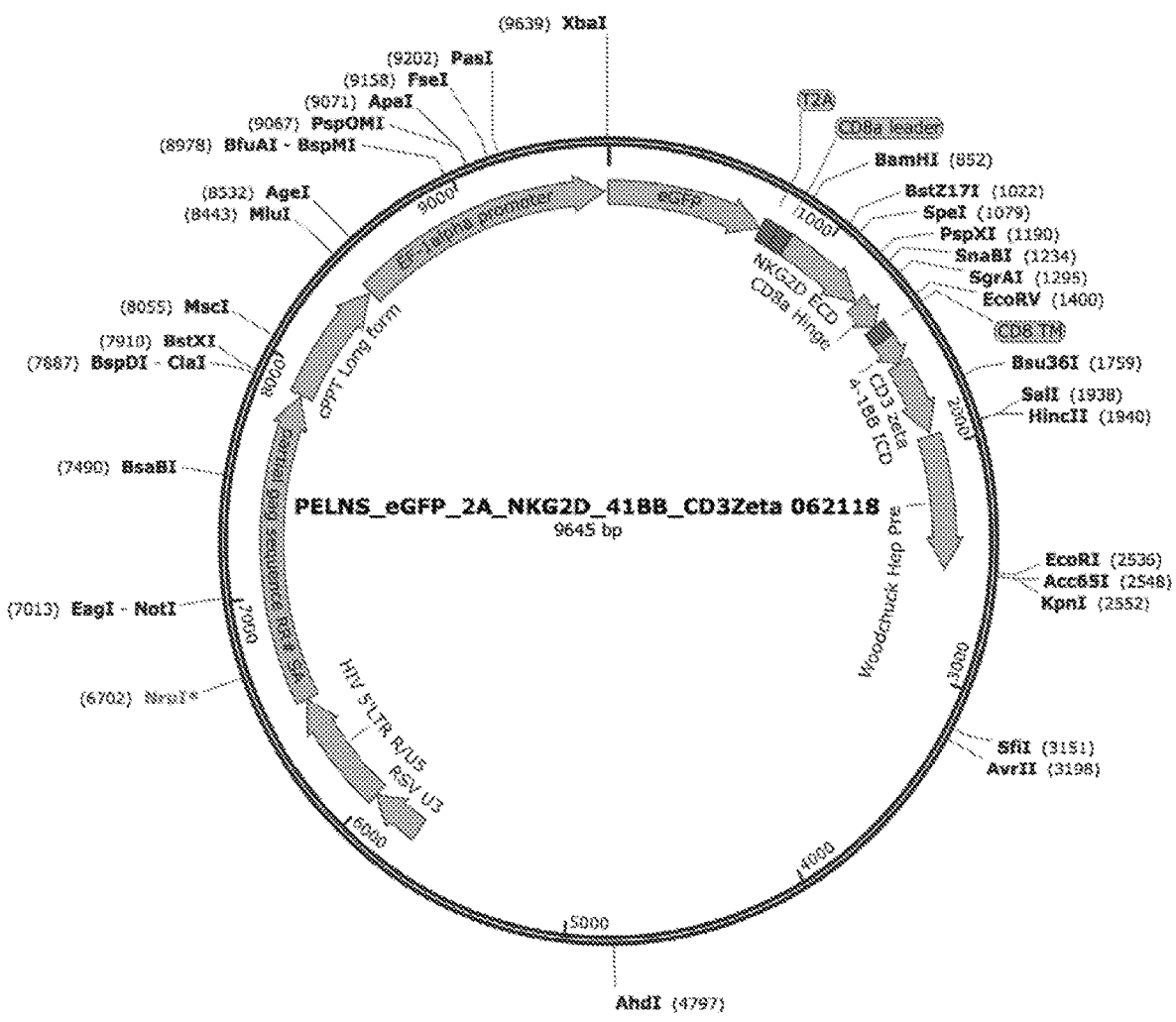
FIG. 10 is a map of vector PELNS_eGFP_2A_NKG2D_41BB_CD3Zeta (SEQ ID NO: 6).
Figure 11:
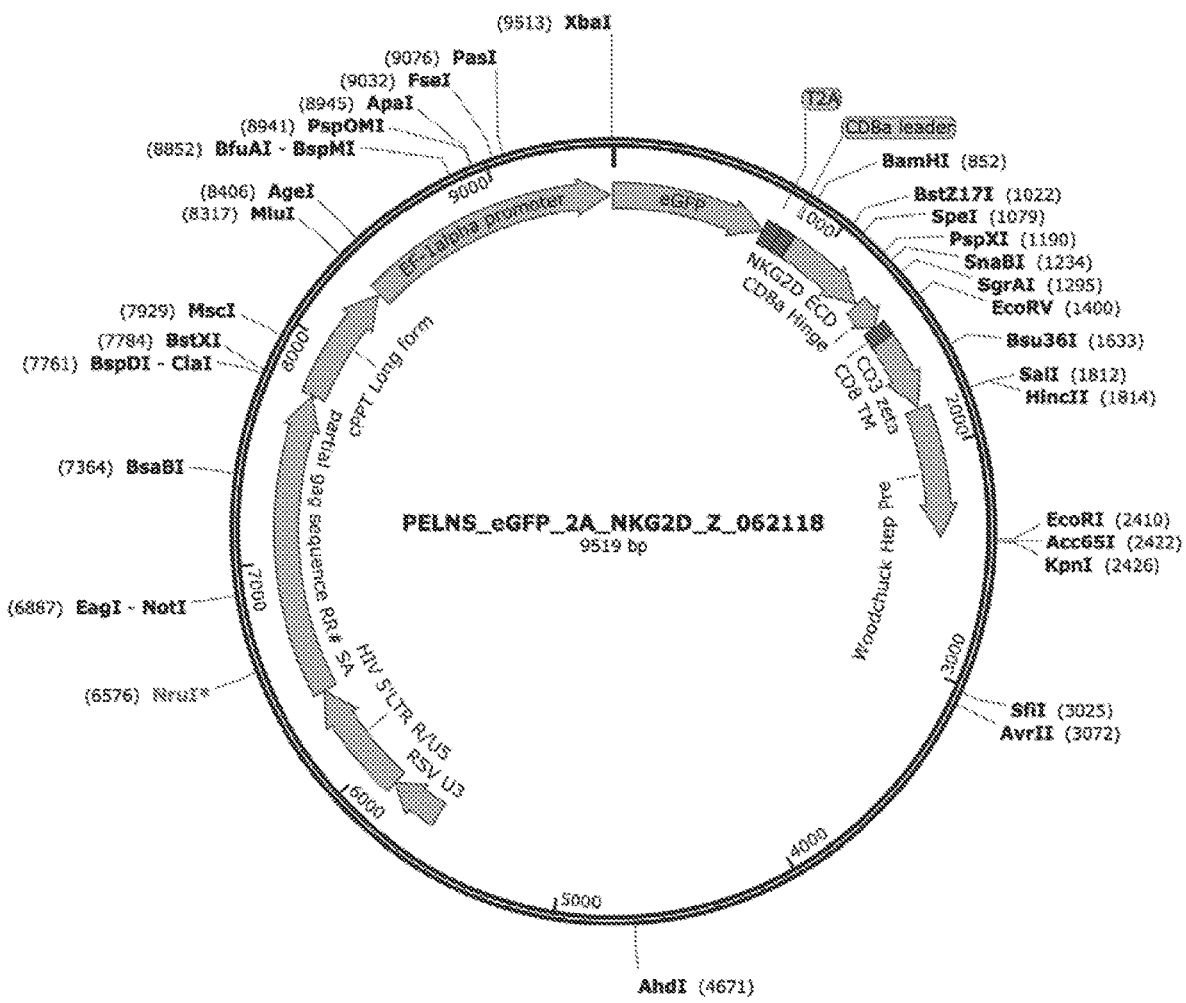
FIG. 11 is a map of vector PELNS_eGFP_2A_NKG2D_CD3Zeta (SEQ ID NO: 7).

CAR T cells nay become exhausted due to the persistent antigen exposure or tonic signaling of the CAR. To ascertain whether T cell exhaustion develops during NKG2D CAR T cell expansion, the expression of the two more abundantly expressed inhibitory receptors on T cells, TIM3 and PD-1, was measured. Similar to untransduced T cells, NKG2D CAR T cells expressed low levels of the PD1 and TIM3 (FIG. 8A). Although these CAR T cells were highly enriched by "T-cell fratricide" in the presence of IL-2, they did not become exhausted. Interestingly, first generation NKG2D-z CAR T cells expressed relatively higher levels of PD-1 and TIM-3 compared to costimulated NKG2D-BBz or -CD27z CAR T cells, and even untransduced T cells. High levels of PD-1 and TIM3 were however expressed on activated T-cells stimulated by anti-CD3/CD28 beads (FIG. 8A). 4-1BB and PD-1 expression were also measured on NKG2D CAR T cells because the presence of the target antigen on T cells may sustain high tonic signaling which leads to increased activation marker and exhaustion. Similar to untransduced T cells, CAR T cells lacked 4-1BB expression (FIG. 8B) indicating a lack of tonic signaling and suggesting insufficient stimulation by NKG2DLs, possibly due to the transient nature of expression of NKG2DLs in activated T cells. Alternatively, the small subsets of 4-1BB expressing CAR T cells might preferentially express NKG2DLs and accordingly be killed by other NKG2D CAR T cells leading to a "CAR T cells-fratricide and auto-stimulation/enrichment" cycle. Incubation of NKG2D CAR T cells with the MDA-MB-231 cell line resulted in robust activation-induced up-regulation of 4-1BB restricted to CAR+ T cells and a significant up-regulation of PD-1 on CAR+ cells after 24 hours of incubation (FIG. 8B). Similar to the above experiments, first generation NKG2D-z CAR T cells expressed relatively higher levels of PD-1 compared to costimulated NKG2D-BBz or -CD27z CAR T cells during culture or when stimulated with MDA-MB-231 cells (FIG. 8B). Together, these data suggested that NKG2D CAR T cells do not become exhausted during ex vivo expansion and that 4-1BB or CD27 costimulation may enable T cells to resist immune exhaustion. These data also demonstrated that CD27 rescues CAR T cells from exhaustion.

Example 6: Control of TNBC by Costimulated NKG2D CAR T Cells In Vivo

Figure 6A:
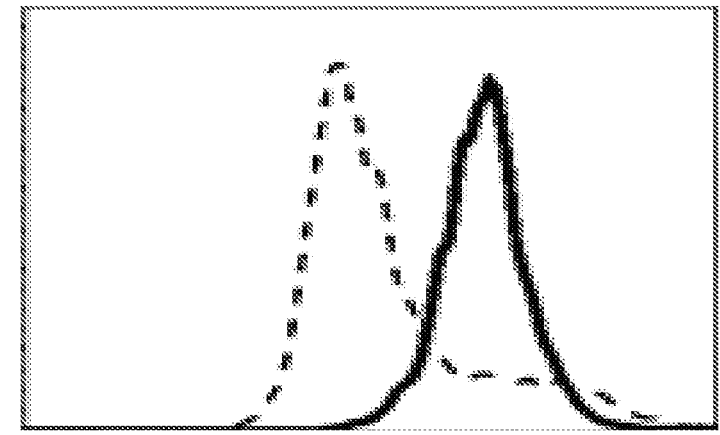
FIGS. 6A-6G are a series of graphs and images demonstrating that costimulated NKG2D CAR T cells inhibit tumor growth of TNBC in vivo.
Figure 6B:
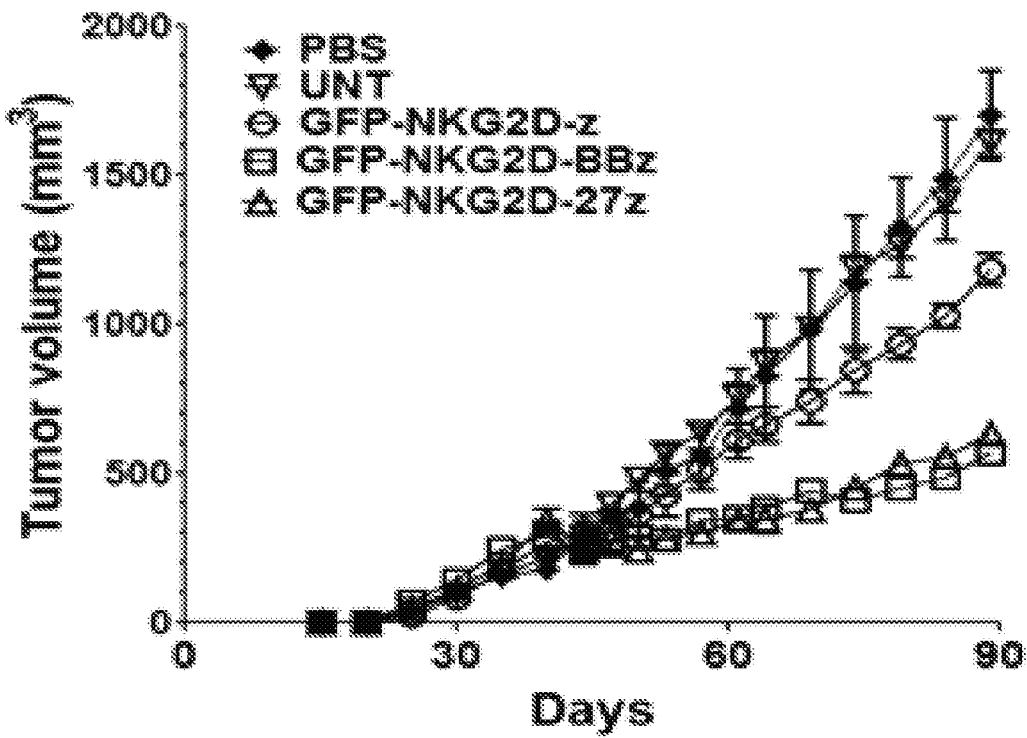
Figure 6C:
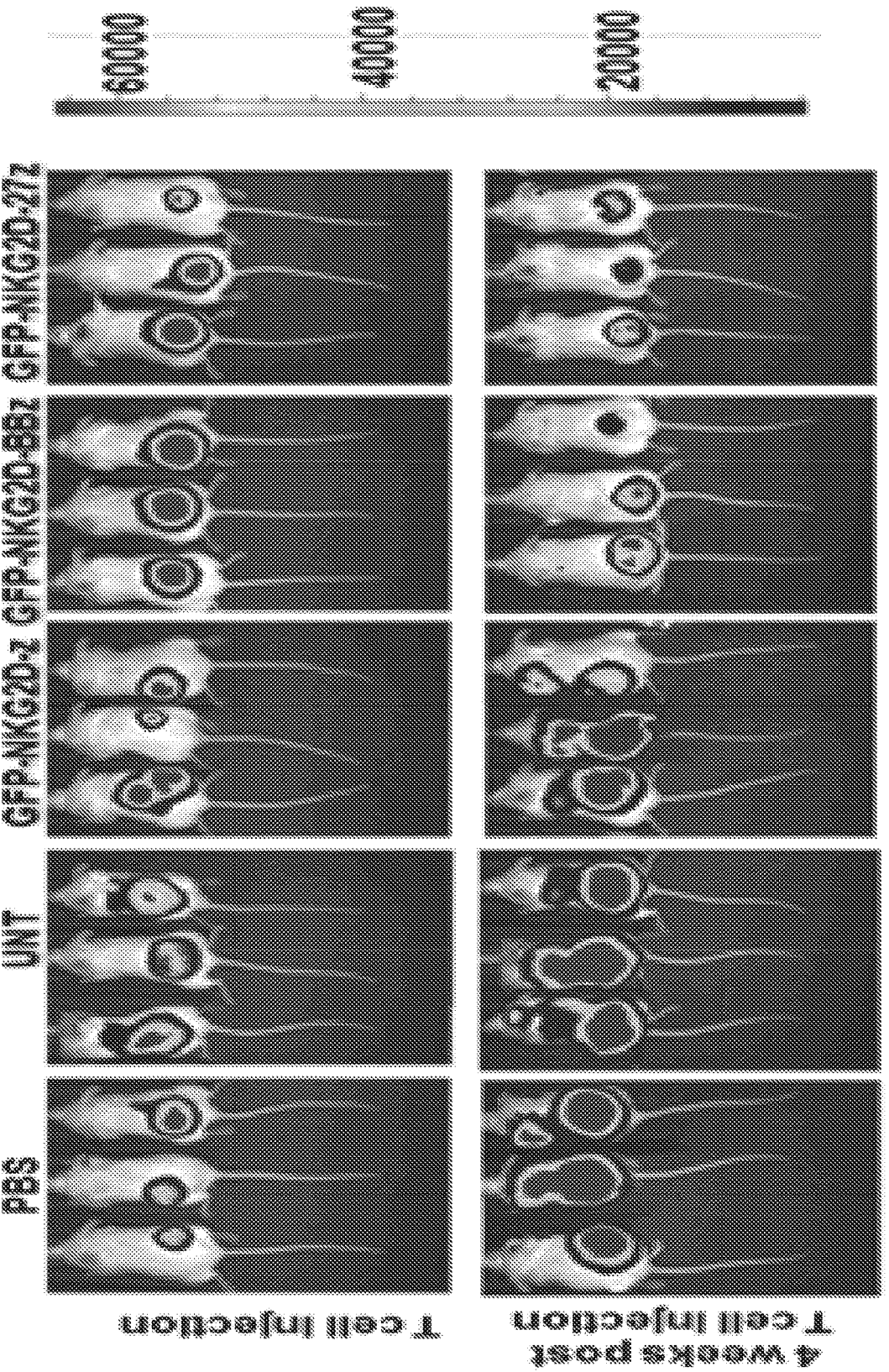

Next the therapeutic efficacy of these NKG2D CAR T cells against human TNBC was evaluated in vivo. First a xenograft model of TNBC was generated by injecting $3\times10^6$ luciferase-labeled NKG2DLs-expressing MDA-MB-231 cells (FIG. 6A) subcutaneously in NSG mice. When tumors reached a mean volume of ~300 mm³, mice were assigned to the following treatment groups: administration of PBS, untransduced T cells or NKG2D CAR(+) T cells on day 40 and day 45 after tumor implantation by tail-vein injection. MDA-MB-231 tumors in the control mice group treated with PBS or untransduced T cells grew progressively beyond the time of T cell transfer as measured by caliper-based sizing and bioluminescent imaging (BLI; FIGS. 6B and 6C). These mice had to be euthanized due to high tumor burden by day 90. Tumor growth was modestly delayed in mice receiving GFP-NKG2D-z T cells, compared with control groups at the latest evaluated time point. In contrast, mice receiving GFP-NKG2D-BBz or -27z CAR T cells were protected from rapid progression (FIGS. 6B and 6C), which was significantly better than NKG2D-z T cells (P<0.001).

Figure 6D:
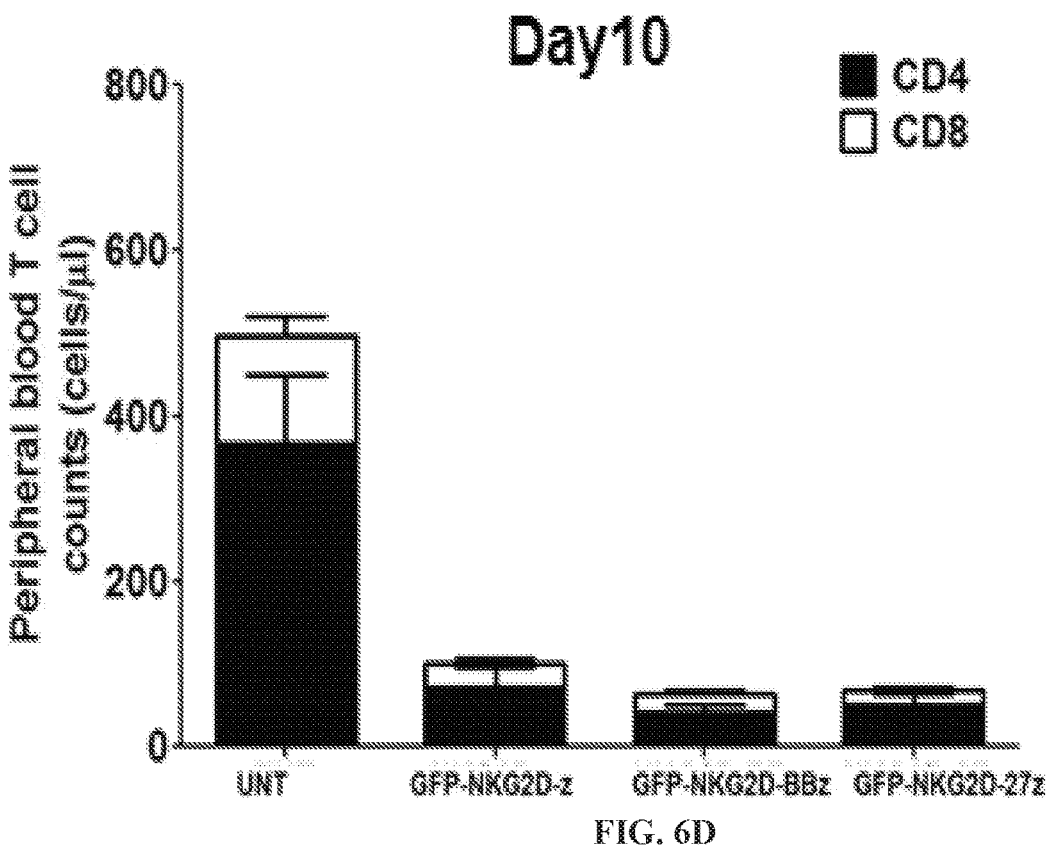
Figure 6E:
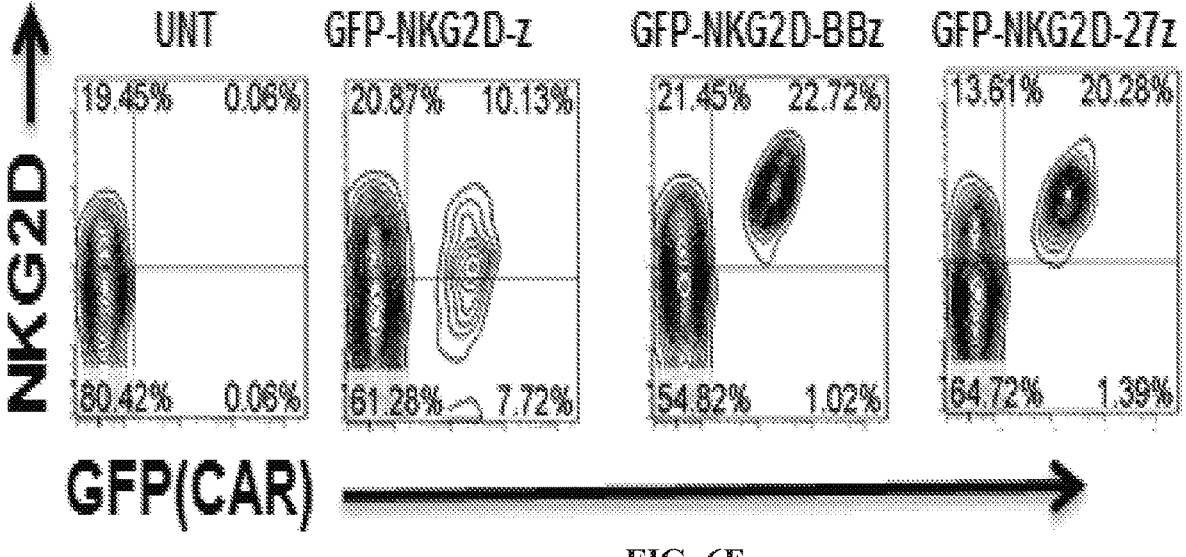

Peripheral blood was collected from tumor-bearing mice and quantified for persistence of infused human T cells. Ten days after the first injection of T cells, human CD4+ T-cell counts were higher compared to CD8+ T-cell counts in the circulation and both CD4+ and CD8. T cells in GFP-NKG2D-z, -BBz and -27z CAR cohorts were present in lower numbers in comparison to untransduced T cells, suggesting early NKG2DLs-specific CAR T cell migration to specific tumor sites (FIG. 6D). NKG2D CAR expressing T cells were detectable in the peripheral blood. The level of CAR expression by NKG2D-BBz and -27z T cells was high compared to the expression detected on NKG2D-z CAR T cells, which poorly expressed on the surface of transduced (GFP+) T cells, suggesting CAR down-regulation (FIG. 6E).

Figures 6F, 6G:
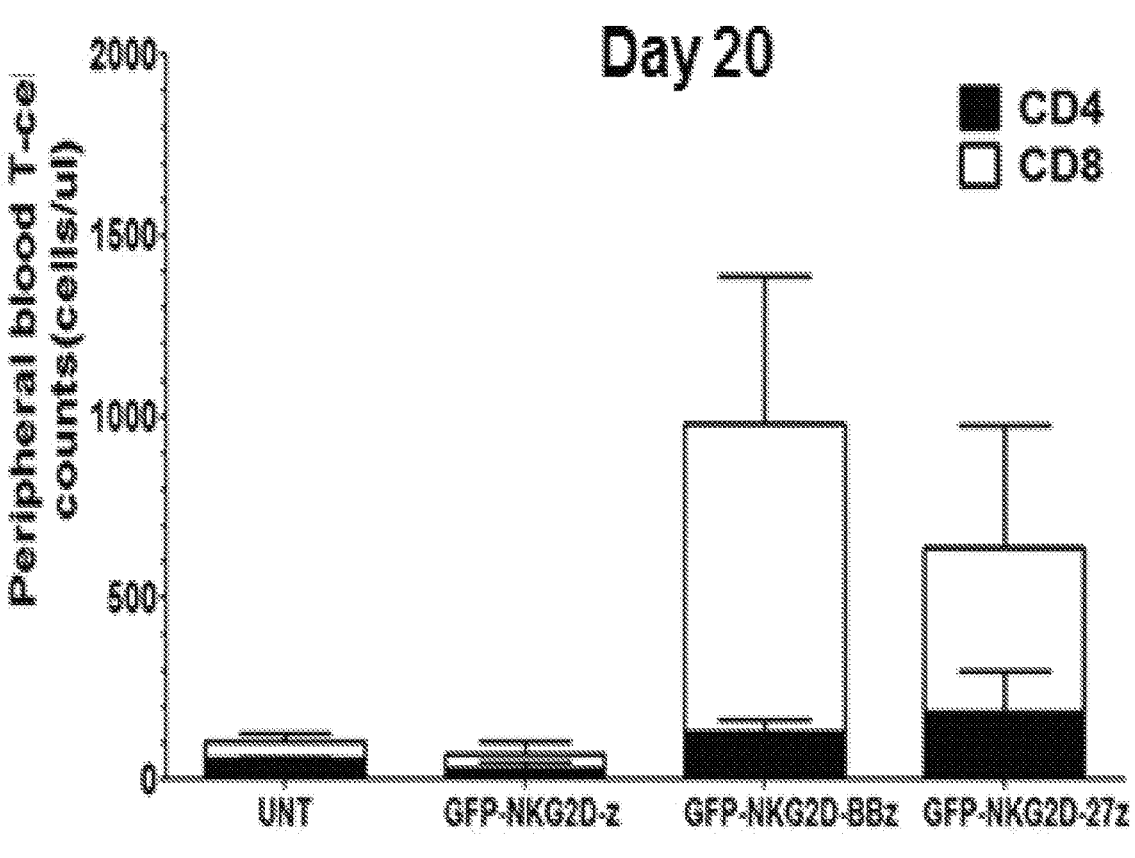

Twenty days after first T cell injection, significant CD4$^+$ and CD8$^+$ T cell expansion was now detected in the peripheral blood of mice receiving GFP-NKG2D-BBz or -27z CAR T cells compared to untransduced and GFP-NKG2D-z treatment groups, indicating roles for 4-1BB and CD27 in T-cell survival in vivo (FIG. 6F). For the costimulated CAR groups tested, the CD8 T-cell counts were higher than the CD4 T cell counts. Analysis of the CD8 data in these two groups revealed statistically similar cell counts in the GFP-NKG2D-BBz CAR T cell treated group compared to -27z group (P>0.05) (FIG. 6F). These results indicate that both 4-1BB and CD27 costimulation augment CD8 T-cell persistence. Similar to what was observed in vitro, 4-1BB or CD27 costimulated NKG2D CAR T cells maintained a high level of surface CAR expression in vivo without the need for additional exogenous IL-2 support; this was not the case for the NKG2D-z CAR (FIG. 6G). These data suggest that costimulated NKG2D CAR expression on the T cell surface is stable and increased in vivo, even after antigen recognition and the proliferation of the CAR T cells. Together, these results support the use of costimulated NKG2D-BBz or -27z CAR T cells as a cellular modality for enhanced treatment of TNBC in vivo.

Example 7: Overview

The expression of NKG2DLs on many primary tumor cells and immunosuppressive cells (e.g., T regulatory cells and myeloid-derived suppressor cells) within the tumor microenvironment makes them attractive targets for the development of novel therapeutics.

NKG2D CAR T cells secreted IFN-γ upon stimulation with NKG2DLs(+) tumor cells and displayed potent cytolytic capacity in vitro against NKG2DLs+ TNBC cells, even at low E/T ratios. Consistently, the production of proinflammatory cytokines and cytolytic capacity by NKG2D-BBz and -27z CAR-T cells was substantially increased after co-culture with NKG2DLs (+) TNBC cell lines, compared with NKG2D-z T cells. Mechanisms accounting for increased effector function by 4-1BB and CD27 costimulated CAR-T cells in vitro appear linked in part to their ability to resist antigen-induced cell death (AICD). These in vitro tumor killing findings further demonstrate that NKG2DLs have promise as novel immunotherapy targets for TNBCs, which currently lack effective targeted therapies. Indeed, two injections of 4-1BB or CD27 costimulated NKG2D CAR T cells exhibited in vivo antitumor effects in a highly invasive MDA-MB-231 xenograft model of human TNBC, compared to the first generation NKG2D CAR T cells. Consistent with clinical observations (Kalos et al., *Sci. Transl. Med.* 3, 95ra73 (2011)), tumor regression was associated with enhanced T-cell persistence in vivo. The greatest number of CAR T cells persisting in the blood 20 days after the first T-cell dose was observed in those animals administered NKG2D-BBz and -27z CAR-T cells followed by NKG2D-z and untransduced T cells, indicating that simultaneous TCR CD3 signaling and 4-1BB or CD27 costimulation triggered by CAR ligation with antigen improves upon TCR signaling alone, implicating a role for 4-1BB and CD27 costimulation in memory T-cell formation in vivo.

In this study, costimulated NKG2D CAR T cells failed to completely eradicate large, established tumors. Major studies suggest that administration of exogenous IL-2 may be necessary for the anti-tumor activity for first generation CAR T cells that lack costimulatory domains. The administration of IL-2 was previously found to have little to no anti-tumor effect on human CAR T cell activity in immunodeficient mice, if the CAR contains a costimulatory domain. Therefore, the omission of exogenous IL-2 is not likely the primary factor accounting for the suboptimal anti-tumor response in this study. The efficacy of NKG2D CAR T cells treatment for TNBC may also be influenced by surface antigen expression level.

Targeting solid tumors, like TNBC, is still challenging, as it may be greatly hampered clinically by the immunosuppressive microenvironment and the inefficient homing of CAR T cells to tumor sites. Combining CAR T cells with other therapies like CTLA-4 and PD-1 inhibitor offers the potential to improve antitumor effects.

One intriguing finding from this study is that in the presence of exogenous IL-2, a potent cytokine stimulator of activated effector lymphocyte expansion and proliferation, NKG2D CAR T cells undergo substantial long-term expansion without evidence of prolonged detriment from fratricide in vitro. In addition, the NKG2D CAR (+) T cells population was enriched during prolonged culture, suggesting a possible auto-stimulatory effect through endogenous expression of induced NKG2DLs after T cell stimulation. The NKG2D CAR T cells of the invention undergo dramatic expansion and preferentially enrich for CAR expressing T cells during culture. Here, exogenous IL-2 promoted the expansion and enrichment of NKG2D-z, -BBz and -27z CAR(+) T cells, which was dependent on a high expression level of the IL-2 receptor alpha subunit, CD25. Without IL-2 support, T cells expressing any of the NKG2D constructs did not expand well and only NKG2D CAR (+) T cells containing 4-1BB or CD27 costimulatory domains enriched for CAR-positivity, demonstrating a benefit from 4-1BB and CD27 costimulation in vitro. These results suggest that incorporation of costimulatory domains into CAR constructs promotes preferential T cell survival and resistance to AICD by upregulating anti-apoptotic. These data also support the three-signal hypothesis (Kershaw et al., Nature Reviews Cancer. 2013; 13(8):525) that optimal T-cell activation and expansion involves T-cell receptor (TCR) activation (signal 1) in addition to costimulatory receptor engagement (signal 2) and cytokine receptor engagement (signal 3).

In conclusion, a self-enrichment phenomenon of NKG2D CAR was identified herein in vitro, which does not affect T-cell expansion. These NKG2D CAR T cells can effectively target NKG2DLs expressing TNBC cells in vitro and CD27 or 4-1BB costimulated CAR T cells can significantly reduce tumor growth in vivo. NKG2D CAR T cell-therapy may provide novel treatment options for patients with TNBCs and may be amenable to combination with immune checkpoint blockade, cytokines and other strategies to transform this approach from being "promising" to being "effective" treatments for TNBC and other solid tumors.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A nucleic acid molecule encoding a chimeric antigen receptor (CAR), wherein the nucleic acid molecule comprises a nucleic acid sequence encoding a natural-killer group 2, member D (NKG2D) extracellular domain, a nucleic acid sequence encoding a CD27 costimulatory domain, and a nucleic acid sequence encoding a CD3 zeta signaling domain, wherein the CAR comprises, from amino to carboxy terminus, the NKG2D extracellular domain, the CD27 costimulatory domain, and the CD3 zeta signaling domain, and wherein the CAR comprises the amino acid sequence of SEQ ID NO: 15.

2. The nucleic acid molecule of claim 1, wherein the nucleic acid molecule comprises the nucleic acid sequence of SEQ ID NO: 14.

3. A vector comprising the nucleic acid molecule of claim 1.

4. A chimeric antigen receptor (CAR) comprising a natural-killer group 2, member D (NKG2D) extracellular domain, a CD27 costimulatory domain, and a CD3 zeta signaling domain, wherein the CAR comprises, from amino to carboxy terminus, the NKG2D extracellular domain, the CD27 costimulatory domain, and the CD3 zeta signaling domain, and wherein the CAR comprises the amino acid sequence of SEQ ID NO: 15.

5. The CAR of claim 4, wherein the CAR is encoded by the nucleic acid sequence of SEQ ID NO: 14.

6. A genetically modified T cell comprising the CAR of claim 4.

7. A method for treating cancer in a subject, the method comprising: administering to the subject an effective amount of the genetically modified T cell of claim 6, thereby treating cancer in the subject.

8. A genetically modified T cell comprising a nucleic acid molecule encoding a chimeric antigen receptor (CAR), wherein the nucleic acid molecule comprises a nucleic acid sequence encoding, from amino to carboxy terminus, a natural-killer group 2, member D (NKG2D) extracellular domain, a nucleic acid sequence encoding a CD27 costimulatory domain, and a nucleic acid sequence encoding a CD3 zeta signaling domain, wherein the CAR comprises the amino acid sequence of SEQ ID NO: 15 or is encoded by the nucleic acid sequence of SEQ ID NO: 14.

9. A genetically modified T cell comprising a nucleic acid molecule encoding a chimeric antigen receptor (CAR), wherein the nucleic acid molecule comprises the nucleic acid sequence of SEQ ID NO: 16 or encodes the amino acid sequence of SEQ ID NO: 17.

10. A genetically modified T cell comprising a chimeric antigen receptor (CAR), wherein the CAR comprises the amino acid sequence of SEQ ID NO: 19 or is encoded by the nucleic acid sequence of SEQ ID NO: 18.

11. A vector comprising a nucleic acid molecule encoding a chimeric antigen receptor (CAR), wherein the nucleic acid molecule comprises a nucleic acid sequence encoding, from amino to carboxy terminus, a natural-killer group 2, member D (NKG2D) extracellular domain, a nucleic acid sequence encoding a CD27 costimulatory domain, and a nucleic acid sequence encoding a CD3 zeta signaling domain, wherein the nucleic acid molecule comprises the nucleic acid sequence of SEQ ID NO: 1.

12. A method for treating triple negative breast cancer (TNBC) in a subject, the method comprising: administering to the subject an effective amount of a genetically modified T cell comprising a nucleic acid molecule encoding, from amino to carboxy terminus, a chimeric antigen receptor (CAR), wherein the nucleic acid molecule comprises a nucleic acid sequence of a natural-killer group 2, member D (NKG2D) extracellular domain, a nucleic acid sequence encoding a CD27 costimulatory domain, and a nucleic acid sequence encoding a CD3 zeta signaling domain, thereby treating TNBC in the subject.

13. The method of claim 12, wherein the subject is a human.

14. The method of claim 12, further comprising wherein the subject is administered a secondary treatment.

15. The method of claim 14, wherein the secondary treatment is selected from the group consisting of immune checkpoint blockade, chemotherapy, radiation, and surgery.

* * * * *

SEQUENCE LISTING

<160> NUMBER OF SEQ ID NOS: 20

<210> SEQ ID NO 1
<211> LENGTH: 9663
<212> TYPE: DNA
<213> ORGANISM: Artificial Sequence
<220> FEATURE:
<223> OTHER INFORMATION: Vector: PELNS_eGFP_2A_NKG2D_CD27_CD3Zeta

<400> SEQUENCE: 1
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagaga     720
tctggcggcg gagagggcag aggaagtctt ctaacatgcg gtgacgtgga ggagaatccc     780
ggccctagat ggccttacca gtgaccgcct tgctcctgcc gctggccttg ctgctccacg     840
ccgccaggcc gggatccttc aaccaagaag ttcaaattcc cttgaccgaa agttactgtg     900
gcccatgtcc taaaaactgg atatgttaca aaaataactg ctaccaattt tttgatgaga     960
gtaaaaactg gtatgagagc caggcttctt gtatgtctca aaatgccagc cttctgaaag    1020
tatacagcaa agaggaccag gatttactta aactggtgaa gtcatatcat tggatgggac    1080
tagtacacat tccaacaaat ggatcttggc agtgggaaga tggctccatt ctctcaccca    1140
acctactaac aataattgaa atgcagaagg gagactgtgc actctatgcc tcgagcttta    1200
aaggctatat agaaaactgt tcaactccaa atacgtacat ctgcatgcaa aggactgtgg    1260
ctagcaccac gacgccagcg ccgcgaccac caacaccggc gcccaccatc gcgtcgcagc    1320
ccctgtccct gcgcccagag gcgtgccggc cagcggcggg gggcgcagtg cacacgaggg    1380
ggctggactt cgcctgtgat atctacatct gggcgccctt ggccgggact tgtgggtcc     1440 ttctcctgtc actggttatc acctttact gccaacgaag aaatatagga tcaaacaaag    1500
gagaaagtcc tgtggagcct gcagagcctt gtcgttacag ctgccccagg gaggaggagg    1560
gcagcaccat ccccatccag gaggattacc gaaaaccgga gcctgcctgc tcccccagag    1620
tgaagttcag caggagcgca gacgcccccg cgtaccagca gggccagaac cagctctata    1680
acgagctcaa tctaggacga agagaggagt acgatgtttt ggacaagaga cgtggccggg    1740
accctgagat ggggggaaag ccgagaagga gaaccctca ggaaggcctg tacaatgaac     1800
tgcagaaaga taagatggcg gaggcctaca gtgagattgg gatgaaaggc gagcgccgga    1860
ggggcaaggg gcacgatggc ctttaccagg tctcagtac agccaccaag gacacctacg     1920
acgcccttca catgcaggcc ctgccccctc gctaagtcga caatcaacct ctggattaca    1980
aaatttgtga agattgact ggtattctta actatgttgc tccttttacg ctatgtggat     2040

```
acgctgcttt aatgcctttg tatcatgcta ttgcttcccg tatggctttc attttctcct      2100
ccttgtataa atcctggttg ctgtctcttt atgaggagtt gtggcccgtt gtcaggcaac      2160
gtggcgtggt gtgcactgtg tttgctgacg caacccccac tggttggggc attgccacca      2220
cctgtcagct cctttccggg actttcgctt tccccctccc tattgccacg gcggaactca      2280
tcgccgcctg ccttgcccgc tgctggacag gggctcggct gttgggcact gacaattccg      2340
tggtgttgtc ggggaagctg acgtcctttc catggctgct cgcctgtgtt gccacctgga      2400
ttctgcgcgg gacgtccttc tgctacgtcc cttcggccct caatccagcg gaccttcctt      2460
cccgcggcct gctgccggct ctgcggcctc ttccgcgtct tcgccttcgc cctcagacga      2520
gtcggatctc cctttgggcc gcctccccgc ctggaattcg agctcggtac ctttaagacc      2580
aatgacttac aaggcagctg tagatcttag ccactttta aaagaaaagg ggggactgga      2640
agggctaatt cactcccaac gaagacaaga tctgcttttt gcttgtactg ggtctctctg      2700
gttagaccag atctgagcct gggagctctc tggctaacta gggaacccac tgcttaagcc      2760
tcaataaagc ttgccttgag tgcttcaagt agtgtgtgcc cgtctgttgt gtgactctgg      2820
taactagaga tccctcagac cctttttagtc agtgtggaaa atctctagca gtagtagttc      2880
atgtcatctt attattcagt atttataact tgcaaagaaa tgaatatcag agagtgagag      2940
gaacttgttt attgcagctt ataatggtta caaataaagc aatagcatca caaatttcac      3000
aaataaagca ttttttttcac tgcattctag ttgtggtttg tccaaactca tcaatgtatc      3060
ttatcatgtc tggctctagc tatcccgccc ctaactccgc ccagttccgc ccattctccg      3120
ccccatggct gactaatttt ttttatttat gcagaggccg aggccgcctc ggcctctgag      3180
ctattccaga agtagtgagg aggctttttt ggaggcctag gcttttgcgt cgagacgtac      3240
ccaattcgcc ctatagtgag tcgtattacg cgcgctcact ggccgtcgtt ttacaacgtc      3300
gtgactggga aaaccctggc gttacccaac ttaatcgcct tgcagcacat cccccttttcg      3360 ccagctggcg taatagcgaa gaggcccgca ccgatcgccc ttcccaacag ttgcgcagcc      3420
tgaatggcga atggcgcgac gcgccctgta gcggcgcatt aagcgcggcg ggtgtggtgg      3480
ttacgcgcag cgtgaccgct acacttgcca gcgccctagc gcccgctcct ttcgctttct      3540
tcccttcctt tctcgccacg ttcgccggct ttccccgtca agctctaaat cggggggctcc     3600 ctttagggtt ccgatttagt gctttacggc acctcgaccc caaaaaacctt gattagggtg      3660 atggttcacg tagtgggcca tcgccctgat agacggtttt tcgccctttg acgttggagt      3720
ccacgttctt taatagtgga ctcttgttcc aaactggaac aacactcaac cctatctcgg      3780
tctattcttt tgatttataa gggattttgc cgatttcggc ctattggtta aaaaatgagc      3840
tgatttaaca aaaatttaac gcgaatttta acaaaatatt aacgtttaca atttcccagg      3900 tggcacttttt cggggaaatg tgcgcggaac ccctatttgt ttatttttct aaatacattc      3960
aaatatgtat ccgctcatga dacaataacc ctgataaatg cttcaataat attgaaaaag      4020
gaagagtatg agtattcaac atttccgtgt cgcccttatt cccttttttg cggcattttg      4080
ccttcctgtt tttgctcacc cagaaacgct ggtgaaagta aaagatgctg aagatcagtt      4140
gggtgcacga gtgggttaca tcgaactgga tctcaacagc ggtaagatcc ttgagagttt      4200
tcgccccgaa gaacgtttttc caatgatgag cactttttaaa gttctgctat gtggcgcggt      4260
attatcccgt attgacgccg ggcaagagca actcggtcgc cgcatacact attctcagaa      4320
tgacttggtt gagtactcac cagtcacaga aaagcatctt acggatggca tgacagtaag      4380
```

-continued

```
agaattatgc agtgctgcca taaccatgag tgataacact gcggccaact tacttctgac   4440
aacgatcgga ggaccgaagg agctaaccgc tttttttgcac aacatggggg atcatgtaac   4500
tcgccttgat cgttgggaac cggagctgaa tgaagccata ccaaacgacg agcgtgacac   4560
cacgatgcct gtagcaatgg caacaacgtt gcgcaaacta ttaactggcg aactacttac   4620
tctagcttcc cggcaacaat taatagactg gatggaggcg gataaagttg caggaccact   4680
tctgcgctcg gcccttccgg ctggctggtt tattgctgat aaatctggag ccggtgagcg   4740
tgggtctcgc ggtatcattg cagcactggg gccagatggt aagccctccc gtatcgtagt   4800
tatctacacg acggggagtc aggcaactat ggatgaacga atagacagat cgctgagat   4860 aggtgcctca ctgattaagc attggtaact gtcagaccaa gtttactcat atatacttta   4920
gattgattta aaacttcatt tttaatttaa aaggatctag gtgaagatcc tttttgataa   4980
tctcatgacc aaaatccctt aacgtgagtt ttcgttccac tgagcgtcag accccgtaga   5040
aaagatcaaa ggatcttctt gagatccttt ttttctgcgc gtaatctgct gcttgcaaac   5100
aaaaaaacca ccgctaccag cggtggtttg tttgccggat caagagctac caactctttt   5160
tccgaaggta actggcttca gcagagcgca gataccaaat actgtccttc tagtgtagcc   5220
gtagttaggc caccacttca agaactctgt agcaccgcct acatacctcg ctctgctaat   5280
cctgttacca gtggctgctg ccagtggcga taagtcgtgt cttaccgggt tggactcaag   5340
acgatagtta ccggataagg cgcagcggtc gggctgaacg gggggttcgt gcacacagcc   5400
cagcttggag cgaacgacct acaccgaact gagataccta cagcgtgagc tatgagaaag   5460
cgccacgctt cccgaaggga gaaaggcgga caggtatccg gtaagcggca gggtcggaac   5520
aggagagcgc acgagggagc ttccagggggg aaacgcctgg tatctttata gtcctgtcgg   5580
gtttcgccac ctctgacttg agcgtcgatt tttgtgatgc tcgtcagggg ggcggagcct   5640
atggaaaaac gccagcaacg cggccttttt acggttcctg gccttttgct ggccttttgc   5700
tcacatgttc tttcctgcgt tatcccctga ttctgtggat aaccgtatta ccgcctttga   5760
gtgagctgat accgctcgcc gcagccgaac gaccgagcgc agcgagtcag tgagcgagga   5820
agcggaagag cgcccaatac gcaaaccgcc tctccccgcg cgttggccga ttcattaatg   5880
cagctggcac gacaggtttc ccgactggaa agcgggcagt gagcgcaacg caattaatgt   5940
gagttagctc actcattagg caccccaggc tttacacttt atgcttccgg ctcgtatgtt   6000
gtgtggaatt gtgagcggat aacaatttca cacaggaaac agctatgacc atgattacgc   6060
caagcgcgca attaaccctc actaaaggga acaaaagctg gagctgcaag cttaatgtag   6120
tcttatgcaa tactcttgta gtcttgcaac atggtaacga tgagttagca acatgcctta   6180
caaggagaga aaaagcaccg tgcatgccga ttggtggaag taaggtggta cgatcgtgcc   6240
ttattaggaa ggcaacagac gggtctgaca tggattggac gaaccactga attgccgcat   6300
tgcagagata ttgtatttaa gtgcctagct cgatacaata aacgggtctc tctggttaga   6360
ccagatctga gcctgggagc tctctggcta actagggaac ccactgctta agcctcaata   6420
aagcttgcct tgagtgcttc aagtagtgtg tgcccgtctg ttgtgtgact ctggtaacta   6480
gagatccctc agaccctttt agtcagtgtg gaaaatctct agcagtggcg cccgaacagg   6540
gacctgaaag cgaaagggaa accagagctc tctcgacgca ggactcggct tgctgaagcg   6600
cgcacggcaa gaggcgaggg gcggcgactg gtgagtacgc caaaaatttt gactagcgga   6660
ggctagaagg agagagatgg gtgcgagagc gtcagtatta gcggggggag aattagatcg   6720
cgatgggaaa aaattcggtt aaggccaggg ggaaagaaaa aatataaatt aaaacatata   6780
```

-continued

```
gtatgggcaa gcagggagct agaacgattc gcagttaatc ctggcctgtt agaaacatca    6840
gaaggctgta gacaaatact gggacagcta caaccatccc ttcagacagg atcagaagaa    6900
cttagatcat tatataatac agtagcaacc ctctattgtg tgcatcaaag gatagagata    6960
aaagacacca aggaagcttt agacaagata gaggaagagc aaaacaaaag taagaccacc    7020
gcacagcaag cggccgctga tcttcagacc tggaggagga gatatgaggg acaattggag    7080
aagtgaatta tataaatata aagtagtaaa aattgaacca ttaggagtag cacccaccaa    7140
ggcaaagaga agagtggtgc agagagaaaa aagagcagtg ggaataggag ctttgttcct    7200
tgggttcttg ggagcagcag gaagcactat gggcgcagcc tcaatgacgc tgacggtaca    7260
ggccagacaa ttattgtctg gtatagtgca gcagcagaac aatttgctga gggctattga    7320
ggcgcaacag catctgttgc aactcacagt ctggggcatc aagcagctcc aggcaagaat    7380
cctggctgtg gaaagatacc taaaggatca acagctcctg gggatttggg gttgctctgg    7440
aaaactcatt tgcaccactg ctgtgccttg gaatgctagt tggagtaata atctctggaa    7500
acagattgga atcacacgac ctggatggag tgggacagag aaattaacaa ttacacaagc    7560
ttaatacact ccttaattga agaatcgcaa aaccagcaag aaaagaatga acaagaatta    7620
ttggaattag ataaatgggc aagtttgtgg aattggttta acataacaaa ttggctgtgg    7680
tatataaaat tattcataat gatagtagga ggcttggtag gtttaagaat agttttttgct    7740 gtactttcta tagtgaatag agttaggcag ggatattcac cattatcgtt tcagacccac    7800
ctcccaaccc cgaggggacc cgacaggccc gaaggaatag aagaagaagg tggagagaga    7860
gacagagaca gatccattcg attagtgaac ggatctcgac ggtatcgatt agactgtagc    7920
ccaggaatat ggcagctaga ttgtacacat ttagaaggaa aagttatctt ggtagcagtt    7980
catgtagcca gtggatatat agaagcagaa gtaattccag cagagacagg gcaagaaaca    8040
gcatacttcc tcttaaaatt agcaggaaga tggccagtaa aaacagtaca tacagacaat    8100
ggcagcaatt tcaccagtac tacagttaag gccgcctgtt ggtgggcggg gatcaagcag    8160
gaatttggca ttccctacaa tccccaaagt caaggagtaa tagaatctat gaataaagaa    8220
ttaaagaaaa ttataggaca ggtaagagat caggctgaac atcttaagac agcagtacaa    8280
atggcagtat tcatccacaa ttttaaaaga aagggggggga ttgggggggta cagtgcaggg    8340 gaaagaatag tagacataat agcaacgac atacaaacta agaattaca aaaacaaatt    8400 acaaaaattc aaaattttcg ggtttattac agggacagca gagatccagt ttggctgcat    8460
acgcgtcgtg aggctccggt gcccgtcagt gggcagagcg cacatcgccc acagtccccg    8520
agaagttggg gggaggggtc ggcaattgaa ccggtgccta gagaaggtgg cgcggggtaa    8580
actgggaaag tgatgtcgtg tactggctcc gcctttttcc cgagggtggg ggagaaccgt    8640
atataagtgc agtagtcgcc gtgaacgttc tttttcgcaa cgggtttgcc gccagaacac    8700
aggtaagtgc cgtgtgtggt tcccgcgggc ctggcctctt tacgggttat ggcccttgcg    8760
tgccttgaat tacttccacc tggctgcagt acgtgattct tgatcccgag cttcgggttg    8820
gaagtgggtg ggagagttcg aggccttgcg cttaaggagc cccttcgcct cgtgcttgag    8880
ttgaggcctg gcctgggcgc tggggccgcc gcgtgcgaat ctggtggcac cttcgcgcct    8940
gtctcgctgc tttcgataag tctctagcca tttaaaattt ttgatgacct gctgcgacgc    9000
tttttttctg gcaagatagt cttgtaaatg cgggccaaga tctgcacact ggtatttcgg    9060
tttttggggc cgcgggcggc gacggggccc gtgcgtccca gcgcacatgt tcggcgaggc    9120
```

```
ggggcctgcg agcgcggcca ccgagaatcg gacgggggta gtctcaagct ggccggcctg      9180
ctctggtgcc tggcctcgcg ccgccgtgta tcgccccgcc ctgggcggca aggctggccc      9240
ggtcggcacc agttgcgtga gcggaaagat ggccgcttcc cggccctgct gcagggagct      9300
caaaatggag gacgcggcgc tcgggagagc gggcgggtga gtcacccaca caaaggaaaa      9360
gggcctttcc gtcctcagcc gtcgcttcat gtgactccac ggagtaccgg cgcccgtcca      9420
ggcacctcga ttagttctcg agcttttgga gtacgtcgtc tttaggttgg ggggaggggt      9480
tttatgcgat ggagtttccc cacactgagt gggtggagac tgaagttagg ccagcttggc      9540
acttgatgta attctccttg gaatttgccc tttttgagtt tggatcttgg ttcattctca      9600
agcctcagac agtggttcaa agtttttttc ttccatttca ggtgtcgtga gctagctcta      9660
gag                                                                    9663

<210> SEQ ID NO 2
<211> LENGTH: 402
<212> TYPE: DNA
<213> ORGANISM: Homo sapiens

<400> SEQUENCE: 2
ttcaaccaag aagttcaaat tcccttgacc gaaagttact gtggcccatg tcctaaaaac        60
tggatatgtt acaaaaataa ctgctaccaa tttttgatg agagtaaaaa ctggtatgag       120
agccaggctt cttgtatgtc tcaaaatgcc agccttctga aagtatacag caaagaggac       180
caggatttac ttaaactggt gaagtcatat cattggatgg gactagtaca cattccaaca       240
aatggatctt ggcagtggga agatggctcc attctctcac ccaacctact aacaataatt       300
gaaatgcaga agggagactg tgcactctat gcctcgagct ttaaaggcta tatagaaaac       360
tgttcaactc caaatacgta catctgcatg caaaggactg tg                         402

<210> SEQ ID NO 3
<211> LENGTH: 134
<212> TYPE: PRT
<213> ORGANISM: Homo sapiens

<400> SEQUENCE: 3

Phe Asn Gln Glu Val Gln Ile Pro Leu Thr Glu Ser Tyr Cys Gly Pro
1               5                   10                  15

Cys Pro Lys Asn Trp Ile Cys Tyr Lys Asn Asn Cys Tyr Gln Phe Phe
            20                  25                  30

Asp Glu Ser Lys Asn Trp Tyr Glu Ser Gln Ala Ser Cys Met Ser Gln
        35                  40                  45

Asn Ala Ser Leu Leu Lys Val Tyr Ser Lys Glu Asp Gln Asp Leu Leu
    50                  55                  60

Lys Leu Val Lys Ser Tyr His Trp Met Gly Leu Val His Ile Pro Thr
65                  70                  75                  80

Asn Gly Ser Trp Gln Trp Glu Asp Gly Ser Ile Leu Ser Pro Asn Leu
                85                  90                  95

Leu Thr Ile Ile Glu Met Gln Lys Gly Asp Cys Ala Leu Tyr Ala Ser
            100                 105                 110

Ser Phe Lys Gly Tyr Ile Glu Asn Cys Ser Thr Pro Asn Thr Tyr Ile
        115                 120                 125

Cys Met Gln Arg Thr Val
    130

<210> SEQ ID NO 4
```

```
<211> LENGTH: 144
<212> TYPE: DNA
<213> ORGANISM: Artificial Sequence
<220> FEATURE:
<223> OTHER INFORMATION: CD27

<400> SEQUENCE: 4
caacgaagga aatatagatc aaacaaagga gaaagtcctg tggagcctgc agagccttgt        60
cgttacagct gccccaggga ggaggagggc agcaccatcc ccatccagga ggattaccga       120
aaaccggagc ctgcctgctc cccc                                               144

<210> SEQ ID NO 5
<211> LENGTH: 48
<212> TYPE: PRT
<213> ORGANISM: Artificial Sequence
<220> FEATURE:
<223> OTHER INFORMATION: CD27

<400> SEQUENCE: 5

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 6
<211> LENGTH: 9645
<212> TYPE: DNA
<213> ORGANISM: Artificial Sequence
<220> FEATURE:
<223> OTHER INFORMATION: Vector: PELNS_eGFP_2A_NKG2D_41BB_CD3Zeta

<400> SEQUENCE: 6
atggtgagca agggcgagga gctgttcacc ggggtggtgc ccatcctggt cgagctggac        60
ggcgacgtaa acggccacaa gttcagcgtg tccggcgagg gcgagggcga tgccacctac       120
ggcaagctga ccctgaagtt catctgcacc accggcaagc tgcccgtgcc ctggcccacc       180
ctcgtgacca ccctgaccta cggcgtgcag tgcttcagcc gctaccccga ccacatgaag       240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
gtgaaccgca tcgagctgaa gggcatcgac ttcaaggagg acggcaacat cctggggcac       420
aagctggagt acaactacaa cagccacaac gtctatatca tggccgacaa gcagaagaac       480
ggcatcaagg tgaacttcaa gatccgccac aacatcgagg acggcagcgt gcagctcgcc       540
gaccactacc agcagaacac ccccatcggc gacggccccg tgctgctgcc cgacaaccac       600
tacctgagca cccagtccgc cctgagcaaa gaccccaacg agaagcgcga tcacatggtc       660
ctgctggagt tcgtgaccgc cgccgggatc actctcggca tggacgagct gtacaagaga       720
tctggcggcg gagagggcag aggaagtctt ctaacatgcg gtgacgtgga ggagaatccc       780
ggccctagat ggccttacca gtgaccgcct tgctcctgcc gctggccttg ctgctccacg       840
ccgccaggcc gggatccttc aaccaagaag ttcaaattcc cttgaccgaa agttactgtg       900
gcccatgtcc taaaaactgg atatgttaca aaaataactg ctaccaattt tttgatgaga       960
gtaaaaactg gtatgagagc caggcttctt gtatgtctca aaatgccagc cttctgaaag      1020
tatacagcaa agaggaccag gatttactta aactggtgaa gtcatatcat tggatgggac      1080
```

-continued

```
tagtacacat tccaacaaat ggatcttggc agtgggaaga tggctccatt ctctcaccca      1140
acctactaac aataattgaa atgcagaagg gagactgtgc actctatgcc tcgagcttta      1200
aaggctatat agaaaactgt tcaactccaa atacgtacat ctgcatgcaa aggactgtgg      1260
ctagcaccac gacgccagcg ccgcgaccac caacaccggc gcccaccatc gcgtcgcagc      1320
ccctgtccct gcgcccagag gcgtgccggc cagcggcggg gggcgcagtg cacacgaggg      1380
ggctggactt cgcctgtgat atctacatct gggcgccctt ggccgggact tgtgggtcc      1440 ttctcctgtc actggttatc accctttact gcaaacgggg cagaaagaaa ctcctgtata      1500
tattcaaaca accatttatg agaccagtac aaactactca agaggaagat ggctgtagct      1560
gccgatttcc agaagaagaa gaaggaggat gtgaactgag agtgaagttc agcaggagcg      1620
cagacgcccc cgcgtaccag cagggccaga accagctcta taacgagctc aatctaggac      1680
gaagagagga gtacgatgtt ttggacaaga acgtggccg ggaccctgag atggggggaa      1740
agccgagaag gaagaaccct caggaaggcc tgtacaatga actgcagaaa gataagatgg      1800
cggaggccta cagtgagatt gggatgaaag gcgagcgccg gaggggcaag gggcacgatg      1860
gcctttacca gggtctcagt acagccacca aggacaccta cgacgccctt cacatgcagg      1920
ccctgccccc tcgctaagtc gacaatcaac ctctggatta caaaatttgt gaaagattga      1980
ctggtattct taactatgtt gctccttta cgctatgtgg atacgctgct ttaatgcctt      2040
tgtatcatgc tattgcttcc cgtatggctt tcattttctc ctccttgtat aaatcctggt      2100
tgctgtctct ttatgaggag ttgtggcccg ttgtcaggca acgtggcgtg gtgtgcactg      2160
tgtttgctga cgcaacccccc actggttggg gcattgccac cacctgtcag ctcctttccg      2220
ggactttcgc tttccccctc cctattgcca cggcggaact catcgccgcc tgccttgccc      2280
gctgctggac aggggctcgg ctgttgggca ctgacaattc cgtggtgttg tcggggaagc      2340
tgacgtcctt tccatggctg ctcgcctgtg ttgccacctg gattctgcgc gggacgtcct      2400
tctgctacgt cccttcggcc ctcaatccag cggaccttcc ttcccgcggc ctgctgccgg      2460
ctctgcggcc tcttccgcgt cttcgccttc gccctcagac gagtcggatc tccctttggg      2520
ccgcctcccc gcctggaatt cgagctcggt acctttaaga ccaatgactt acaaggcagc      2580
tgtagatctt agccactttt taaaagaaaa ggggggactg gaagggctaa ttcactccca      2640
acgaagacaa gatctgcttt ttgcttgtac tgggtctctc tggttagacc agatctgagc      2700
ctgggagctc tctggctaac tagggaaccc actgcttaag cctcaataaa gcttgccttg      2760
agtgcttcaa gtagtgtgtg cccgtctgtt gtgtgactct ggtaactaga tccctcag      2820 acccttttag tcagtgtgga aaatctctag cagtagtagt tcatgtcatc ttattattca      2880
gtatttataa cttgcaaaga atgaatatc agagagtgag aggaacttgt ttattgcagc      2940
ttataatggt tacaaataaa gcaatagcat cacaaatttc acaaataaag cattttttttc      3000 actgcattct agttgtggtt tgtccaaact catcaatgta tcttatcatg tctggctcta      3060
gctatcccgc ccctaactcc gcccagttcc gcccattctc cgccccatgg ctgactaatt      3120
ttttttattt atgcagaggc cgaggccgcc tcggcctctg agctattcca gaagtagtga      3180
ggaggctttt ttggaggcct aggcttttgc gtcgagacgt acccaattcg ccctatagtg      3240
agtcgtatta cgcgcgctca ctggccgtcg ttttacaacg tcgtgactgg gaaaaccctg      3300
gcgttaccca acttaatcgc cttgcagcac atccccctt cgccagctgg cgtaatagcg      3360
aagaggcccg caccgatcgc ccttcccaac agttgcgcag cctgaatggc gaatggcgcg      3420
acgcgccctg tagcggcgca ttaagcgcgg cgggtgtggt ggttacgcgc agcgtgaccg      3480
```

-continued

```
ctacacttgc cagcgcccta gcgcccgctc ctttcgcttt cttccttcc tttctcgcca      3540 cgttcgccgg ctttccccgt caagctctaa atcgggggct ccctttaggg ttccgattta      3600
gtgctttacg gcacctcgac cccaaaaaac ttgattaggg tgatggttca cgtagtgggc      3660
catcgccctg atagacggtt tttcgccctt tgacgttgga gtccacgttc tttaatagtg      3720
gactcttgtt ccaaactgga acaacactca accctatctc ggtctattct tttgatttat      3780
aagggatttt gccgatttcg gcctattggt taaaaaatga gctgatttaa caaaaattta      3840
acgcgaattt taacaaaata ttaacgttta caatttccca ggtggcactt ttcggggaaa      3900
tgtgcgcgga accccatttt gtttattttt ctaaatacat tcaaatatgt atccgctcat      3960
gagacaataa ccctgataaa tgcttcaata atattgaaaa aggaagagta tgagtattca      4020
acatttccgt gtcgccctta ttcccttttt tgcggcattt tgccttcctg tttttgctca      4080
cccagaaacg ctggtgaaag taaaagatgc tgaagatcag ttgggtgcac gagtgggtta      4140
catcgaactg gatctcaaca gcggtaagat ccttgagagt tttcgccccg aagaacgttt      4200
tccaatgatg agcacttta aagttctgct atgtggcgcg gtattatccc gtattgacgc      4260
cgggcaagag caactcggtc gccgcataca ctattctcag aatgacttgg ttgagtactc      4320
accagtcaca gaaaagcatc ttacggatgg catgacagta agagaattat gcagtgctgc      4380
cataaccatg agtgataaca ctgcggccaa cttacttctg acaacgatcg gaggaccgaa      4440
ggagctaacc gcttttttgc acaacatggg ggatcatgta actcgccttg atcgttggga      4500
accggagctg aatgaagcca taccaaacga cgagcgtgac accacgatgc ctgtagcaat      4560
ggcaacaacg ttgcgcaaac tattaactgg cgaactactt actctagctt cccggcaaca      4620
attaatagac tggatggagg cggataaagt tgcaggacca cttctgcgct cggcccttcc      4680
ggctggctgg tttattgctg ataaatctgg agccggtgag cgtgggtctc gcggtatcat      4740
tgcagcactg gggccagatg gtaagccctc ccgtatcgta gttatctaca cgacggggag      4800
tcaggcaact atggatgaac gaaatagaca gatcgctgag ataggtgcct cactgattaa      4860
gcattggtaa ctgtcagacc aagtttactc atatatactt tagattgatt taaaacttca      4920
tttttaattt aaaaggatct aggtgaagat cctttttgat aatctcatga ccaaaatccc      4980
ttaacgtgag ttttcgttcc actgagcgtc agaccccgta gaaaagatca aaggatcttc      5040
ttgagatcct ttttttctgc gcgtaatctg ctgcttgcaa acaaaaaaac caccgctacc      5100
agcggtggtt tgtttgccgg atcaagagct accaactctt tttccgaagg taactggctt      5160
cagcagagcg cagataccaa atactgtcct tctagtgtag ccgtagttag gccaccactt      5220
caagaactct gtagcaccgc ctacatacct cgctctgcta atcctgttac cagtggctgc      5280
tgccagtggc gataagtcgt gtcttaccgg gttggactca agacgatagt taccggataa      5340
ggcgcagcgg tcgggctgaa cggggggttc gtgcacacag cccagcttgg agcgaacgac      5400
ctacaccgaa ctgagatacc tacagcgtga gctatgagaa agcgccacgc ttcccgaagg      5460
gagaaaggcg gacaggtatc cggtaagcgg cagggtcgga acaggagagc gcacgaggga      5520
gcttccaggg ggaaacgcct ggtatcttta tagtcctgtc gggtttcgcc acctctgact      5580
tgagcgtcga tttttgtgat gctcgtcagg ggggcggagc ctatggaaaa acgccagcaa      5640
cgcggccttt ttacggttcc tggccttttg ctggcctttt gctcacatgt tctttcctgc      5700
gttatcccct gattctgtgg ataaccgtat taccgccttt gagtgagctg ataccgctcg      5760
ccgcagccga acgaccgagc gcagcgagtc agtgagcgag gaagcggaag agcgcccaat      5820
```

-continued

```
acgcaaaccg cctctccccg cgcgttggcc gattcattaa tgcagctggc acgacaggtt    5880
tcccgactgg aaagcgggca gtgagcgcaa cgcaattaat gtgagttagc tcactcatta    5940 ggcacccccag gctttacact ttatgcttcc ggctcgtatg ttgtgtggaa ttgtgagcgg    6000
ataacaattt cacacaggaa acagctatga ccatgattac gccaagcgcg caattaaccc    6060
tcactaaagg gaacaaaagc tggagctgca agcttaatgt agtcttatgc aatactcttg    6120
tagtcttgca acatggtaac gatgagttag caacatgcct tacaaggaga gaaaaagcac    6180
cgtgcatgcc gattggtgga agtaaggtgg tacgatcgtg ccttattagg aaggcaacag    6240
acgggtctga catggattgg acgaaccact gaattgccgc attgcagaga tattgtattt    6300
aagtgcctag ctcgatacaa taaacgggtc tctctggtta gaccagatct gagcctggga    6360
gctctctggc taactaggga acccactgct taagcctcaa taaagcttgc cttgagtgct    6420
tcaagtagtg tgtgcccgtc tgttgtgtga ctctggtaac tagagatccc tcagaccctt    6480
ttagtcagtg tggaaaatct ctagcagtgg cgcccgaaca gggacctgaa agcgaaaggg    6540
aaaccagagc tctctcgacg caggactcgg cttgctgaag cgcgcacggc aagaggcgag    6600
gggcggcgac tggtgagtac gccaaaaatt ttgactagcg gaggctagaa ggagagagat    6660
gggtgcgaga gcgtcagtat taagcggggg agaattagat cgcgatggga aaaaattcgg    6720
ttaaggccag ggggaaagaa aaatataaa ttaaaacata tagtatgggc aagcagggag    6780
ctagaacgat tcgcagttaa tcctggcctg ttagaaacat cagaaggctg tagacaaata    6840
ctgggacagc tacaaccatc ccttcagaca ggatcagaag aacttagatc attatataat    6900
acagtagcaa ccctctattg tgtgcatcaa aggatagaga taaaagacac caaggaagct    6960
ttagacaaga tagaggaaga gcaaaacaaa agtaagacca ccgcacagca agcggccgct    7020
gatcttcaga cctggaggag gagatatgag ggacaattgg agaagtgaat tatataaata    7080
taaagtagta aaaattgaac cattaggagt agcacccacc aaggcaaaga gaagagtggt    7140
gcagagagaa aaaagagcag tgggaatagg agctttgttc cttgggttct gggagcagc    7200 aggaagcact atgggcgcag cctcaatgac gctgacggta caggccagac aattattgtc    7260
tggtatagtg cagcagcaga acaatttgct gagggctatt gaggcgcaac agcatctgtt    7320
gcaactcaca gtctggggca tcaagcagct ccaggcaaga atcctggctg tggaaagata    7380
cctaaaggat caacagctcc tggggatttg gggttgctct ggaaaactca tttgcaccac    7440
tgctgtgcct tggaatgcta gttggagtaa taaatctctg gaacagattg gaatcacacg    7500
acctggatgg agtgggacag agaaattaac aattacacaa gcttaataca ctccttaatt    7560
gaagaatcgc aaaaccagca agaaaagaat gaacaagaat tattggaatt agataaatgg    7620
gcaagtttgt ggaattggtt taacataaca aattggctgt ggtatataaa attattcata    7680
atgatagtag gaggcttggt aggtttaaga atagtttttg ctgtactttc tatagtgaat    7740
agagttaggc agggatattc accattatcg tttcagaccc acctcccaac cccgagggga    7800
cccgacaggc ccgaaggaat agaagaagaa ggtggagaga gagacagaga cagatccatt    7860
cgattagtga acggatctcg acggtatcga ttagactgta gcccaggaat atggcagcta    7920
gattgtacac atttagaagg aaaagttatc ttggtagcag ttcatgtagc cagtggatat    7980
atagaagcag aagtaattcc agcagagaca gggcaagaaa cagcatactt cctcttaaaa    8040
ttagcaggaa gatggccagt aaaaacagta catacagaca atggcagcaa tttcaccagt    8100
actacagtta aggccgcctg ttggtgggcg gggatcaagc aggaatttgg cattccctac    8160
aatccccaaa gtcaaggagt aatagaatct atgaataaag aattaaagaa aattatagga    8220
```

```
caggtaagag atcaggctga acatcttaag acagcagtac aaatggcagt attcatccac    8280
aattttaaaa gaaaaggggg gattggggGg tacagtgcag gggaaagaat agtagacata    8340
atagcaacag acatacaaac taaagaatta caaaaacaaa ttacaaaaat tcaaaatttt    8400
cgggtttatt acagggacag cagagatcca gtttggctgc atacgcgtcg tgaggctccg    8460
gtgcccgtca gtgggcagag cgcacatcgc ccacagtccc cgagaagttg gggggagggg    8520
tcggcaattg aaccggtgcc tagagaaggt ggcgcggggt aaactgggaa agtgatgtcg    8580
tgtactggct ccgcctttt cccgagggtg ggggagaacc gtatataagt gcagtagtcg    8640
ccgtgaacgt tcttttttcgc aacgggtttg ccgccagaac acaggtaagt gccgtgtgtg    8700
gttcccgcgg gcctggcctc tttacgggtt atggcccttg cgtgccttga attacttcca    8760
cctggctgca gtacgtgatt cttgatcccg agcttcgggt tggaagtggg tgggagagtt    8820
cgaggccttg cgcttaagga gcccctcgc ctcgtgcttg agttgaggcc tggcctgggc    8880
gctggggccg ccgcgtgcga atctggtggc accttcgcgc ctgtctcgct gctttcgata    8940
agtctctagc catttaaaat ttttgatgac ctgctgcgac gctttttttc tggcaagata    9000
gtcttgtaaa tgcgggccaa gatctgcaca ctggtatttc ggttttttggg gccgcgggcg    9060 gcgacggggc ccgtgcgtcc cagcgcacat gttcggcgag gcggggcctg cgagcgcggc    9120
caccgagaat cggacggggg tagtctcaag ctggccggcc tgctctggtg cctggcctcg    9180
cgccgccgtg tatcgccccg ccctgggcgg caaggctggc ccggtcggca ccagttgcgt    9240
gagcggaaag atggccgctt cccggccctg ctgcagggag ctcaaaatgg aggacgcggc    9300
gctcgggaga gcgggcgggt gagtcaccca cacaaaggaa aagggccttt ccgtcctcag    9360
ccgtcgcttc atgtgactcc acggagtacc gggcgccgtc caggcacctc gattagttct    9420
cgagcttttg gagtacgtcg tctttaggtt ggggggaggg gttttatgcg atggagtttc    9480
cccacactga gtgggtggag actgaagtta ggccagcttg gcacttgatg taattctcct    9540
tggaatttgc cctttttgag tttggatctt ggttcattct caagcctcag acagtggttc    9600
aaagtttttt tcttccattt caggtgtcgt gagctagctc tagag    9645
```

```
<210> SEQ ID NO 7
<211> LENGTH: 9519
<212> TYPE: DNA
<213> ORGANISM: Artificial Sequece
<220> FEATURE:
<223> OTHER INFORMATION: Vector: PELNS_eGFP_2A_NKG2D_CD3Zeta

<400> SEQUENCE: 7
```

```
atggtgagca aggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctacccccga ccacatgaag    240 cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
```

-continued

```
tacctgagca cccagtccgc cctgagcaaa gaccccaacg agaagcgcga tcacatggtc      660
ctgctggagt tcgtgaccgc cgccgggatc actctcggca tggacgagct gtacaagaga      720
tctggcggcg gagagggcag aggaagtctt ctaacatgcg gtgacgtgga ggagaatccc      780
ggccctagat ggccttacca gtgaccgcct tgctcctgcc gctggccttg ctgctccacg      840
ccgccaggcc gggatccttc aaccaagaag ttcaaattcc cttgaccgaa agttactgtg      900
gcccatgtcc taaaaactgg atatgttaca aaaataactg ctaccaattt tttgatgaga      960
gtaaaaactg gtatgagagc caggcttctt gtatgtctca aaatgccagc cttctgaaag     1020
tatacagcaa agaggaccag gatttactta aactggtgaa gtcatatcat tggatgggac     1080
tagtacacat tccaacaaat ggatcttggc agtgggaaga tggctccatt ctctcaccca     1140
acctactaac aataattgaa atgcagaagg gagactgtgc actctatgcc tcgagcttta     1200
aaggctatat agaaaactgt tcaactccaa atacgtacat ctgcatgcaa aggactgtgg     1260
ctagcaccac gacgccagcg ccgcgaccac caacaccggc gcccaccatc gcgtcgcggc     1320
ccctgtccct gcgcccagag gcgtgccggc cagcggcggg gggcgcagtg cacacgaggg     1380
ggctggactt cgcctgtgat atctacatct gggcgccctt ggccgggact tgtgggggtcc     1440 ttctcctgtc actggttatc accctttact gcagagtgaa gttcagcagg agcgcagacg     1500
cccccgcgta ccagcagggc cagaaccagc tctataacga gctcaatcta ggacgaagag     1560
aggagtacga tgttttggac aagagacgtg gccgggaccc tgagatgggg ggaaagccga     1620
gaaggaagaa ccctcaggaa ggcctgtaca atgaactgca gaaagataag atggcggagg     1680
cctacagtga gattgggatg aaaggcgagc gccggagggg caaggggcac gatggccttt     1740
accagggtct cagtacagcc accaaggaca cctacgacgc ccttcacatg caggccctgc     1800
cccctcgcta agtcgacaat caacctctgg attacaaaat ttgtgaaaga ttgactggta     1860
ttcttaacta tgttgctcct tttacgctat gtggatacgc tgctttaatg cctttgtatc     1920
atgctattgc ttcccgtatg gctttcattt tctcctcctt gtataaatcc tggttgctgt     1980
ctctttatga ggagttgtgg cccgttgtca ggcaacgtgg cgtggtgtgc actgtgtttg     2040
ctgacgcaac ccccactggt tggggcattg ccaccacctg tcagctcctt ccgggacttt     2100
tcgctttccc cctccctatt gccacggcgg aactcatcgc cgcctgcctt gcccgctgct     2160
ggacaggggc tcggctgttg ggcactgaca attccgtggt gttgtcgggg aagctgacgt     2220
cctttccatg gctgctcgcc tgtgttgcca cctggattct gcgcgggacg tccttctgct     2280
acgtcccttc ggccctcaat ccagcggacc ttccttcccg cggcctgctg ccggctctgc     2340
ggcctcttcc gcgtcttcgc cttcgccctc agacgagtcg gatctccctt tgggccgcct     2400
ccccgcctgg aattcgagct cggtacccttt aagaccaatg acttacaagg cagctgtaga     2460
tcttagccac ttttttaaaag aaaagggggg actggaaggg ctaattcact cccaacgaag     2520
acaagatctg ctttttgctt gtactgggtc tctctggtta gaccagatct gagcctggga     2580
gctctctggc taactaggga acccactgct taagcctcaa taaagcttgc cttgagtgct     2640
tcaagtagtg tgtgcccgtc tgttgtgtga ctctggtaac tagagatccc tcagaccctt     2700
ttagtcagtg tggaaaatct ctagcagtag tagttcatgt catcttatta ttcagtattt     2760
ataacttgca aagaaatgaa tatcagagag tgagaggaac ttgtttattg cagcttataa     2820
tggttacaaa taaagcaata gcatcacaaa tttcacaaat aaagcatttt tttcactgca     2880
ttctagttgt ggtttgtcca aactcatcaa tgtatcttat catgtctggc tctagctatc     2940
ccgcccctaa ctccgcccag ttccgcccat tctccgcccc atggctgact aattttttttt     3000
```

-continued

```
atttatgcag aggccgaggc cgcctcggcc tctgagctat tccagaagta gtgaggaggc   3060
ttttttggag gcctaggctt ttgcgtcgag acgtacccaa ttcgccctat agtgagtcgt   3120
attacgcgcg ctcactggcc gtcgtttac aacgtcgtga ctgggaaaac cctggcgtta   3180
cccaacttaa tcgccttgca gcacatcccc ctttcgccag ctggcgtaat agcgaagagg   3240
cccgcaccga tcgcccttcc caacagttgc gcagcctgaa tggcgaatgg cgcgacgcgc   3300
cctgtagcgg cgcattaagc gcggcgggtg tggtggttac gcgcagcgtg accgctacac   3360
ttgccagcgc cctagcgccc gctcctttcg ctttcttccc ttcctttctc gccacgttcg   3420
ccggctttcc ccgtcaagct ctaaatcggg ggctcccttt agggttccga tttagtgctt   3480
tacggcacct cgaccccaaa aaacttgatt agggtgatgg ttcacgtagt gggccatcgc   3540
cctgatagac ggtttttcgc cctttgacgt tggagtccac gttctttaat agtggactct   3600
tgttccaaac tggaacaaca ctcaacccta tctcggtcta ttcttttgat ttataaggga   3660
ttttgccgat ttcggcctat tggttaaaaa atgagctgat ttaacaaaaa tttaacgcga   3720
attttaacaa aatattaacg tttacaattt cccaggtggc acttttcggg gaaatgtgcg   3780
cggaacccct atttgtttat ttttctaaat acattcaaat atgtatccgc tcatgagaca   3840
ataaccctga taaatgcttc aataatattg aaaaaggaag agtatgagta ttcaacattt   3900
ccgtgtcgcc cttattccct tttttgcggc attttgcctt cctgtttttg ctcacccaga   3960
aacgctggtg aaagtaaaag atgctgaaga tcagttgggt gcacgagtgg gttacatcga   4020
actggatctc aacagcggta agatccttga gagttttcgc cccgaagaac gttttccaat   4080
gatgagcact tttaaagttc tgctatgtgg cgcggtatta tcccgtattg acgccgggca   4140
agagcaactc ggtcgccgca tacactattc tcagaatgac ttggttgagt actcaccagt   4200
cacagaaaag catcttacgg atggcatgac agtaagagaa ttatgcagtg ctgccataac   4260
catgagtgat aacactgcgg ccaacttact tctgacaacg atcggaggac cgaaggagct   4320
aaccgctttt ttgcacaaca tgggggatca tgtaactcgc cttgatcgtt gggaaccgga   4380
gctgaatgaa gccataccaa acgacgagcg tgacaccacg atgcctgtag caatggcaac   4440
aacgttgcgc aaactattaa ctggcgaact acttactcta gcttcccggc aacaattaat   4500
agactggatg gaggcggata aagttgcagg accacttctg cgctcggccc ttccggctgg   4560
ctggtttatt gctgataaat ctggagccgg tgagcgtggg tctcgcggta tcattgcagc   4620
actggggcca gatggtaagc cctcccgtat cgtagttatc tacacgacgg ggagtcaggc   4680
aactatggat gaacgaaata gacagatcgc tgagataggt gcctcactga ttaagcattg   4740
gtaactgtca gaccaagttt actcatatat actttagatt gatttaaaac ttcattttta   4800
atttaaaagg atctaggtga agatcctttt tgataatctc atgaccaaaa tcccttaacg   4860
tgagttttcg ttccactgag cgtcagaccc cgtagaaaag atcaaaggat cttcttgaga   4920
tccttttttt ctgcgcgtaa tctgctgctt gcaaacaaaa aaaccaccgc taccagcggt   4980
ggtttgtttg ccggatcaag agctaccaac tctttttccg aaggtaactg gcttcagcag   5040
agcgcagata ccaaatactg tccttctagt gtagccgtag ttaggccacc acttcaagaa   5100
ctctgtagca ccgcctacat acctcgctct gctaatcctg ttaccagtgg ctgctgccag   5160
tggcgataag tcgtgtctta ccgggttgga ctcaagacga tagttaccgg ataaggcgca   5220
gcggtcgggc tgaacggggg gttcgtgcac acagcccagc ttggagcgaa cgacctacac   5280
cgaactgaga tacctacagc gtgagctatg agaaagcgcc acgcttcccg aagggagaaa   5340
```

-continued

```
ggcggacagg tatccggtaa gcggcagggt cggaacagga gagcgcacga gggagcttcc      5400 aggggggaaac gcctggtatc tttatagtcc tgtcgggttt cgccacctct gacttgagcg     5460
tcgatttttg tgatgctcgt caggggggcg gagcctatgg aaaaacgcca gcaacgcggc     5520
ctttttacgg ttcctggcct tttgctggcc ttttgctcac atgttctttc ctgcgttatc     5580
ccctgattct gtggataacc gtattaccgc ctttgagtga gctgataccg ctcgccgcag     5640
ccgaacgacc gagcgcagcg agtcagtgag cgaggaagcg gaagagcgcc caatacgcaa     5700
accgcctctc cccgcgcgtt ggccgattca ttaatgcagc tggcacgaca ggtttcccga     5760
ctggaaagcg ggcagtgagc gcaacgcaat taatgtgagt tagctcactc attaggcacc     5820
ccaggcttta cactttatgc ttccggctcg tatgttgtgt ggaattgtga gcggataaca     5880
atttcacaca ggaaacagct atgaccatga ttacgccaag cgcgcaatta accctcacta     5940
aagggaacaa aagctggagc tgcaagctta atgtagtctt atgcaatact cttgtagtct     6000
tgcaacatgg taacgatgag ttagcaacat gccttacaag agagaaaaa gcaccgtgca      6060 tgccgattgg tggaagtaag gtggtacgat cgtgccttat taggaaggca acagacgggt      6120
ctgacatgga ttggacgaac cactgaattg ccgcattgca gagatattgt atttaagtgc      6180
ctagctcgat acaataaacg ggtctctctg gttagaccag atctgagcct gggagctctc      6240
tggctaacta gggaacccac tgcttaagcc tcaataaagc ttgccttgag tgcttcaagt      6300
agtgtgtgcc cgtctgttgt gtgactctgg taactagaga tccctcagac ccttttagtc      6360
agtgtggaaa atctctagca gtggcgcccg aacagggacc tgaaagcgaa agggaaacca     6420
gagctctctc gacgcaggac tcggcttgct gaagcgcgca cggcaagagg cgaggggcgg     6480
cgactggtga gtacgccaaa aattttgact agcggaggct agaaggagag agatgggtgc     6540
gagagcgtca gtattaagcg ggggagaatt agatcgcgat gggaaaaaat tcggttaagg     6600
ccagggggaa agaaaaaata taaattaaaa catatagtat gggcaagcag ggagctagaa     6660
cgattcgcag ttaatcctgg cctgttagaa acatcagaag gctgtagaca aatactggga     6720
cagctacaac catcccttca gacaggatca gaagaactta gatcattata taatacagta     6780
gcaaccctct attgtgtgca tcaaaggata gagataaaag acaccaagga agctttagac     6840
aagatagagg aagagcaaaa caaaagtaag accaccgcac agcaagcggc cgctgatctt     6900
cagacctgga ggaggagata tgagggacaa ttggagaagt gaattatata aatataaagt     6960
agtaaaaatt gaaccattag gagtagcacc caccaaggca aagagaagag tggtgcagag     7020
agaaaaaaga gcagtgggaa taggagcttt gttccttggg ttcttgggag cagcaggaag     7080
cactatgggc gcagcctcaa tgacgctgac ggtacaggcc agacaattat tgtctggtat     7140
agtgcagcag cagaacaatt tgctgagggc tattgaggcg caacagcatc tgttgcaact     7200
cacagtctgg ggcatcaagc agctccaggc aagaatcctg gctgtggaaa gatacctaaa     7260
ggatcaacag ctcctgggga tttggggttg ctctggaaaa ctcatttgca ccactgctgt     7320
gccttggaat gctagttgga gtaataaatc tctggaacag attggaatca cacgacctgg     7380
atggagtggg acagagaaat taacaattac acaagcttaa tacactcctt aattgaagaa     7440
tcgcaaaacc agcaagaaaa gaatgaacaa gaattattgg aattagataa atgggcaagt     7500
ttgtggaatt ggtttaacat aacaaattgg ctgtggtata taaaattatt cataatgata     7560
gtaggaggct tggtaggttt aagaatagtt tttgctgtac tttctatagt gaatagagtt     7620 aggcaggat attcaccatt atcgtttcag acccacctcc caaccccgag gggacccgac      7680
aggcccgaag gaatagaaga agaaggtgga gagagagaca gagacagatc cattcgatta     7740
```

-continued

```
gtgaacggat ctcgacggta tcgattagac tgtagcccag gaatatggca gctagattgt   7800
acacatttag aaggaaaagt tatcttggta gcagttcatg tagccagtgg atatatagaa   7860
gcagaagtaa ttccagcaga gacagggcaa gaaacagcat acttcctctt aaaattagca   7920
ggaagatggc cagtaaaaac agtacataca gacaatggca gcaatttcac cagtactaca   7980
gttaaggccg cctgttggtg ggcggggatc aagcaggaat ttggcattcc ctacaatccc   8040
caaagtcaag gagtaataga atctatgaat aaagaattaa agaaaattat aggacaggta   8100
agagatcagg ctgaacatct taagacagca gtacaaatgg cagtattcat ccacaatttt   8160
aaaagaaaag ggggggattgg ggggtacagt gcaggggaaa gaatagtaga cataatagca   8220
acagacatac aaactaaaga attacaaaaa caaattacaa aaattcaaaa ttttcgggtt   8280
tattacaggg acagcagaga tccagtttgg ctgcatacgc gtcgtgaggc tccggtgccc   8340
gtcagtgggc agagcgcaca tcgcccacag tccccgagaa gttgggggga ggggtcggca   8400
attgaaccgg tgcctagaga aggtggcgcg gggtaaactg ggaaagtgat gtcgtgtact   8460
ggctccgcct ttttcccgag ggtgggggag aaccgtatat aagtgcagta gtcgccgtga   8520
acgttctttt tcgcaacggg tttgccgcca gaacacaggt aagtgccgtg tgtggttccc   8580
gcgggcctgg cctctttacg ggttatggcc cttgcgtgcc ttgaattact tccacctggc   8640
tgcagtacgt gattcttgat cccgagcttc gggttggaag tgggtgggag agttcgaggc   8700
cttgcgctta aggagcccct tcgcctcgtg cttgagttga ggcctggcct gggcgctggg   8760 ccgccgcgt gcgaatctgg tggcaccttc gcgcctgtct cgctgctttc gataagtctc   8820
tagccattta aaatttttga tgacctgctg cgacgctttt tttctggcaa gatagtcttg   8880
taaatgcggg ccaagatctg cacactggta tttcggtttt tggggccgcg gcggcgacg   8940 gggcccgtgc gtcccagcgc acatgttcgg cgaggcgggg cctgcgagcg cggccaccga   9000
gaatcggacg ggggtagtct caagctggcc ggcctgctct ggtgcctggc ctcgcgccgc   9060
cgtgtatcgc cccgccctgg gcggcaaggc tggcccggtc ggcaccagtt gcgtgagcgg   9120
aaagatggcc gcttcccggc cctgctgcag ggagctcaaa atggaggacg cggcgctcgg   9180
gagagcgggc gggtgagtca cccacacaaa ggaaaagggc ctttccgtcc tcagccgtcg   9240
cttcatgtga ctccacggag taccgggcgc cgtccaggca cctcgattag ttctcgagct   9300
tttggagtac gtcgtcttta ggttggggggg aggggtttta tgcgatggag tttccccaca   9360
ctgagtgggt ggagactgaa gttaggccag cttggcactt gatgtaattc tccttggaat   9420 ttgcccttt tgagtttgga tcttggttca ttctcaagcc tcagacagtg gttcaaagtt   9480
tttttcttcc atttcaggtg tcgtgagcta gctctagag   9519
```

<210> SEQ ID NO 8
<211> LENGTH: 23
<212> TYPE: PRT
<213> ORGANISM: Artificial Sequence
<220> FEATURE:
<223> OTHER INFORMATION: CD8 alpha transmembrane domain

<400> SEQUENCE: 8

```
Ile Tyr Ile Trp Ala Pro Leu Ala Gly Thr Cys Gly Val Leu Leu Leu
1               5                  10                  15

Ser Leu Val Ile Thr Leu Tyr
            20
```

<210> SEQ ID NO 9

<211> LENGTH: 68
<212> TYPE: DNA
<213> ORGANISM: Artificial Sequence
<220> FEATURE:
<223> OTHER INFORMATION: CD8 alpha transmembrane domain

<400> SEQUENCE: 9
atctacatct gggcacccctt ggctggaaca tgcggggtcc tgctgctgag cttggtgatc       60
acccttta                                                                  68

<210> SEQ ID NO 10
<211> LENGTH: 13
<212> TYPE: PRT
<213> ORGANISM: Artificial Sequence
<220> FEATURE:
<223> OTHER INFORMATION: GS linker

<400> SEQUENCE: 10

Ser Gly Gly Gly Gly Ser Gly Gly Gly Gly Ser Ser Gly
1               5                   10

<210> SEQ ID NO 11
<211> LENGTH: 39
<212> TYPE: DNA
<213> ORGANISM: Artificial Sequence
<220> FEATURE:
<223> OTHER INFORMATION: GS linker

<400> SEQUENCE: 11
agcggaggtg gaggtagtgg cggtggaggc agctctggt                                39

<210> SEQ ID NO 12
<211> LENGTH: 112
<212> TYPE: PRT
<213> ORGANISM: Artificial Sequence
<220> FEATURE:
<223> OTHER INFORMATION: CD3 zeta signaling domain

<400> SEQUENCE: 12

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 13
<211> LENGTH: 336
<212> TYPE: DNA
<213> ORGANISM: Artificial Sequence
<220> FEATURE:
<223> OTHER INFORMATION: CD3 zeta signaling domain

<400> SEQUENCE: 13
agagtgaagt tcagcaggag cgcagacgcc cccgcgtaca gcagggccca gaaccagctc       60

-continued

```
tataacgagc tcaatctagg acgaagagag gagtacgatg ttttggacaa gagacgtggc        120
cgggaccctg agatggggggg aaagccgaga aggaagaacc ctcaggaagg cctgtacaat       180
gaactgcaga aagataagat ggcggaggcc tacagtgaga ttgggatgaa aggcgagcgc        240
cggaggggca aggggcacga tggcctttac caggctctca gtacagccac caaggacacc        300
tacgacgccc ttcacatgca ggccctgccc cctcgc                                  336
```

```
<210> SEQ ID NO 14
<211> LENGTH: 1095
<212> TYPE: DNA
<213> ORGANISM: Artificial Sequence
<220> FEATURE:
<223> OTHER INFORMATION: NKG2D_CD27_CD3Zeta CAR

<400> SEQUENCE: 14
ttcaaccaag aagttcaaat tcccttgacc gaaagttact gtggcccatg tcctaaaaac        60
tggatatgtt acaaaaataa ctgctaccaa tttttttgatg agagtaaaaa ctggtatgag       120
agccaggctt cttgtatgtc tcaaaatgcc agccttctga agtatacag caaagaggac         180 caggatttac ttaaactggt gaagtcatat cattggatgg gactagtaca cattccaaca        240
aatggatctt ggcagtggga agatggctcc attctctcac ccaacctact aacaataatt        300
gaaatgcaga agggagactg tgcactctat gcctcgagct ttaaaggcta tatagaaaac        360
tgttcaactc caaatacgta catctgcatg caaaggactg tggctagcac cacgacgcca        420
gcgccgcgac caccaacacc ggcgcccacc atcgcgtcgc agcccctgtc cctgcgccca        480
gaggcgtgcc ggccagcggc ggggggcgca gtgcacacga gggggctgga cttcgcctgt        540
gatatctaca tctgggcgcc cttggccggg acttgtgggg tccttctcct gtcactggtt        600 atcaccctttt actgccaacg aaggaaatat agatcaaaca aaggagaaag tcctgtggag       660
cctgcagagc cttgtcgtta cagctgcccc agggaggagg agggcagcac catccccatc        720
caggaggatt accgaaaacc ggagcctgcc tgctcccca gagtgaagtt cagcaggagc         780
gcagacgccc ccgcgtacca gcagggccag aaccagctct ataacgagct caatctagga        840
cgaagagagg agtacgatgt ttttggacaag agacgtggcc gggaccctga gatgggggga        900
aagccgagaa ggaagaaccc tcaggaaggc ctgtacaatg aactgcagaa agataagatg        960
gcggaggcct acagtgagat tgggatgaaa ggcgagcgcc ggagggggcaa ggggcacgat       1020 ggcctttacc agggtctcag tacagccacc aaggacacct acgacgccct tcacatgcag        1080
gccctgcccc ctcgc                                                         1095
```

```
<210> SEQ ID NO 15
<211> LENGTH: 365
<212> TYPE: PRT
<213> ORGANISM: Artificial Sequence
<220> FEATURE:
<223> OTHER INFORMATION: NKG2D_CD27_CD3Zeta CAR

<400> SEQUENCE: 15

Phe Asn Gln Glu Val Gln Ile Pro Leu Thr Glu Ser Tyr Cys Gly Pro
1               5                   10                  15

Cys Pro Lys Asn Trp Ile Cys Tyr Lys Asn Asn Cys Tyr Gln Phe Phe
            20                  25                  30

Asp Glu Ser Lys Asn Trp Tyr Glu Ser Gln Ala Ser Cys Met Ser Gln
        35                  40                  45

Asn Ala Ser Leu Leu Lys Val Tyr Ser Lys Glu Asp Gln Asp Leu Leu
```

```
                 50                    55                    60
Lys Leu Val Lys Ser Tyr His Trp Met Gly Leu Val His Ile Pro Thr
65                    70                    75                    80

Asn Gly Ser Trp Gln Trp Glu Asp Gly Ser Ile Leu Ser Pro Asn Leu
                      85                    90                    95

Leu Thr Ile Ile Glu Met Gln Lys Gly Asp Cys Ala Leu Tyr Ala Ser
                 100                   105                   110

Ser Phe Lys Gly Tyr Ile Glu Asn Cys Ser Thr Pro Asn Thr Tyr Ile
             115                   120                   125

Cys Met Gln Arg Thr Val Ala Ser Thr Thr Thr Pro Ala Pro Arg Pro
         130                   135                   140

Pro Thr Pro Ala Pro Thr Ile Ala Ser Gln Pro Leu Ser Leu Arg Pro
145                   150                   155                   160

Glu Ala Cys Arg Pro Ala Ala Gly Gly Ala Val His Thr Arg Gly Leu
             165                   170                   175

Asp Phe Ala Cys Asp Ile Tyr Ile Trp Ala Pro Leu Ala Gly Thr Cys
         180                   185                   190

Gly Val Leu Leu Leu Ser Leu Val Ile Thr Leu Tyr Cys Gln Arg Arg
         195                   200                   205

Lys Tyr Arg Ser Asn Lys Gly Glu Ser Pro Val Glu Pro Ala Glu Pro
         210                   215                   220

Cys Arg Tyr Ser Cys Pro Arg Glu Glu Glu Gly Ser Thr Ile Pro Ile
225                   230                   235                   240

Gln Glu Asp Tyr Arg Lys Pro Glu Pro Ala Cys Ser Pro Arg Val Lys
             245                   250                   255

Phe Ser Arg Ser Ala Asp Ala Pro Ala Tyr Gln Gln Gly Gln Asn Gln
             260                   265                   270

Leu Tyr Asn Glu Leu Asn Leu Gly Arg Arg Glu Glu Tyr Asp Val Leu
             275                   280                   285

Asp Lys Arg Arg Gly Arg Asp Pro Glu Met Gly Gly Lys Pro Arg Arg
         290                   295                   300

Lys Asn Pro Gln Glu Gly Leu Tyr Asn Glu Leu Gln Lys Asp Lys Met
305                   310                   315                   320

Ala Glu Ala Tyr Ser Glu Ile Gly Met Lys Gly Glu Arg Arg Arg Gly
             325                   330                   335

Lys Gly His Asp Gly Leu Tyr Gln Gly Leu Ser Thr Ala Thr Lys Asp
             340                   345                   350

Thr Tyr Asp Ala Leu His Met Gln Ala Leu Pro Pro Arg
         355                   360                   365
```

<210> SEQ ID NO 16
<211> LENGTH: 1077
<212> TYPE: DNA
<213> ORGANISM: Artificial Sequence
<220> FEATURE:
<223> OTHER INFORMATION: NKG2D_41BB_CD3Zeta CAR

<400> SEQUENCE: 16

```
ttcaaccaag aagttcaaat tcccttgacc gaaagttact gtggcccatg tcctaaaaac      60
tggatatgtt acaaaaataa ctgctaccaa tttttgatg agagtaaaaa ctggtatgag     120
agccaggctt cttgtatgtc tcaaaatgcc agccttctga agtatacag caaagaggac     180 caggatttac ttaaactggt gaagtcatat cattggatgg gactagtaca cattccaaca     240
aatggatctt ggcagtggga agatggctcc attctctcac ccaacctact aacaataatt     300
```

```
gaaatgcaga agggagactg tgcactctat gcctcgagct ttaaaggcta tatagaaaac    360
tgttcaactc caaatacgta catctgcatg caaaggactg tggctagcac cacgacgcca    420
gcgccgcgac caccaacacc ggcgcccacc atcgcgtcgc agccctgtc cctgcgccca     480 gaggcgtgcc ggccagcggc ggggggcgca gtgcacacga gggggctgga cttcgcctgt    540
gatatctaca tctgggcgcc cttggccggg acttgtgggg tccttctcct gtcactggtt    600
atcacccttt actgcaaacg gggcagaaag aaactcctgt atatattcaa acaaccattt    660
atgagaccag tacaaactac tcaagaggaa gatggctgta gctgccgatt tccagaagaa    720
gaagaaggag gatgtgaact gagagtgaag ttcagcagga gcgcagacgc ccccgcgtac    780
cagcagggcc agaaccagct ctataacgag ctcaatctag gacgaagaga ggagtacgat    840
gttttggaca gagacgtgg ccgggaccct gagatggggg gaaagccgag aaggaagaac     900
cctcaggaag gcctgtacaa tgaactgcag aaagataaga tggcggaggc ctacagtgag    960
attgggatga aaggcgagcg ccggagggg aagggcacg atggccttta ccagggtctc      1020
agtacagcca ccaaggacac ctacgacgcc cttcacatgc aggccctgcc ccctcgc       1077
```

<210> SEQ ID NO 17
<211> LENGTH: 359
<212> TYPE: PRT
<213> ORGANISM: Artificial Sequence
<220> FEATURE:
<223> OTHER INFORMATION: NKG2D_41BB_CD3Zeta CAR

<400> SEQUENCE: 17

```
Phe Asn Gln Glu Val Gln Ile Pro Leu Thr Glu Ser Tyr Cys Gly Pro
1               5                   10                  15

Cys Pro Lys Asn Trp Ile Cys Tyr Lys Asn Asn Cys Tyr Gln Phe Phe
            20                  25                  30

Asp Glu Ser Lys Asn Trp Tyr Glu Ser Gln Ala Ser Cys Met Ser Gln
        35                  40                  45

Asn Ala Ser Leu Leu Lys Val Tyr Ser Lys Glu Asp Gln Asp Leu Leu
    50                  55                  60

Lys Leu Val Lys Ser Tyr His Trp Met Gly Leu Val His Ile Pro Thr
65                  70                  75                  80

Asn Gly Ser Trp Gln Trp Glu Asp Gly Ser Ile Leu Ser Pro Asn Leu
                85                  90                  95

Leu Thr Ile Ile Glu Met Gln Lys Gly Asp Cys Ala Leu Tyr Ala Ser
            100                 105                 110

Ser Phe Lys Gly Tyr Ile Glu Asn Cys Ser Thr Pro Asn Thr Tyr Ile
            115                 120                 125

Cys Met Gln Arg Thr Val Ala Ser Thr Thr Thr Pro Ala Pro Arg Pro
    130                 135                 140

Pro Thr Pro Ala Pro Thr Ile Ala Ser Gln Pro Leu Ser Leu Arg Pro
145                 150                 155                 160

Glu Ala Cys Arg Pro Ala Ala Gly Gly Ala Val His Thr Arg Gly Leu
                165                 170                 175

Asp Phe Ala Cys Asp Ile Tyr Ile Trp Ala Pro Leu Ala Gly Thr Cys
            180                 185                 190

Gly Val Leu Leu Leu Ser Leu Val Ile Thr Leu Tyr Cys Lys Arg Gly
            195                 200                 205

Arg Lys Lys Leu Leu Tyr Ile Phe Lys Gln Pro Phe Met Arg Pro Val
    210                 215                 220

Gln Thr Thr Gln Glu Glu Asp Gly Cys Ser Cys Arg Phe Pro Glu Glu
```

```
225                 230                 235                 240

Glu Glu Gly Gly Cys Glu Leu Arg Val Lys Phe Ser Arg Ser Ala Asp
                245                 250                 255

Ala Pro Ala Tyr Gln Gln Gly Gln Asn Gln Leu Tyr Asn Glu Leu Asn
                260                 265                 270

Leu Gly Arg Arg Glu Glu Tyr Asp Val Leu Asp Lys Arg Arg Gly Arg
                275                 280                 285

Asp Pro Glu Met Gly Gly Lys Pro Arg Arg Lys Asn Pro Gln Glu Gly
        290                 295                 300

Leu Tyr Asn Glu Leu Gln Lys Asp Lys Met Ala Glu Ala Tyr Ser Glu
305                 310                 315                 320

Ile Gly Met Lys Gly Glu Arg Arg Arg Gly Lys Gly His Asp Gly Leu
                325                 330                 335

Tyr Gln Gly Leu Ser Thr Ala Thr Lys Asp Thr Tyr Asp Ala Leu His
                340                 345                 350

Met Gln Ala Leu Pro Pro Arg
        355
```

```
<210> SEQ ID NO 18
<211> LENGTH: 951
<212> TYPE: DNA
<213> ORGANISM: Artificial Sequence
<220> FEATURE:
<223> OTHER INFORMATION: NKG2D_CD3Zeta CAR

<400> SEQUENCE: 18
ttcaaccaag aagttcaaat tcccttgacc gaaagttact gtggcccatg tcctaaaaac      60
tggatatgtt acaaaaataa ctgctaccaa tttttttgatg agagtaaaaa ctggtatgag     120
agccaggctt cttgtatgtc tcaaaatgcc agccttctga agtatacag caaagaggac      180 caggatttac ttaaactggt gaagtcatat cattggatgg actagtaca cattccaaca      240 aatggatctt ggcagtggga agatggctcc attctctcac ccaacctact aacaataatt     300
gaaatgcaga agggagactg tgcactctat gcctcgagct ttaaaggcta tatagaaaac     360
tgttcaactc caaatacgta catctgcatg caaaggactg tggctagcac cacgacgcca     420
gcgccgcgac caccaacacc ggcgcccacc atcgcgtcgc agcccctgtc cctgcgccca     480
gaggcgtgcc ggccagcggc gggggcgca gtgcacacga ggggctgga cttcgcctgt      540 gatatctaca tctgggcgcc cttggccggg acttgtgggg tcttctcct gtcactggtt      600 atcacccttt actgcagagt gaagttcagc aggagcgcag acgcccccgc gtaccagcag     660
ggccagaacc agctctataa cgagctcaat ctaggacgaa gagaggagta cgatgtttg      720 gacaagagac gtggccggga ccctgagatg ggggaaagc cgagaaggaa gaaccctcag     780
gaaggcctgt acaatgaact gcagaaagat aagatggcgg aggcctacag tgagattggg     840
atgaaaggcg agcgccggag gggcaagggg cacgatggcc tttaccaggg tctcagtaca     900
gccaccaagg acacctacga cgcccttcac atgcaggccc tgccccctcg c              951
```

```
<210> SEQ ID NO 19
<211> LENGTH: 317
<212> TYPE: PRT
<213> ORGANISM: Artificial Sequence
<220> FEATURE:
<223> OTHER INFORMATION: NKG2D_CD3Zeta CAR

<400> SEQUENCE: 19

Phe Asn Gln Glu Val Gln Ile Pro Leu Thr Glu Ser Tyr Cys Gly Pro
```

```
1               5                    10                   15

Cys Pro Lys Asn Trp Ile Cys Tyr Lys Asn Asn Cys Tyr Gln Phe Phe
            20                  25                  30

Asp Glu Ser Lys Asn Trp Tyr Glu Ser Gln Ala Ser Cys Met Ser Gln
            35                  40                  45

Asn Ala Ser Leu Leu Lys Val Tyr Ser Lys Glu Asp Gln Asp Leu Leu
            50                  55                  60

Lys Leu Val Lys Ser Tyr His Trp Met Gly Leu Val His Ile Pro Thr
65                  70                  75                  80

Asn Gly Ser Trp Gln Trp Glu Asp Gly Ser Ile Leu Ser Pro Asn Leu
                85                  90                  95

Leu Thr Ile Ile Glu Met Gln Lys Gly Asp Cys Ala Leu Tyr Ala Ser
            100                 105                 110

Ser Phe Lys Gly Tyr Ile Glu Asn Cys Ser Thr Pro Asn Thr Tyr Ile
            115                 120                 125

Cys Met Gln Arg Thr Val Ala Ser Thr Thr Thr Pro Ala Pro Arg Pro
    130                 135                 140

Pro Thr Pro Ala Pro Thr Ile Ala Ser Gln Pro Leu Ser Leu Arg Pro
145                 150                 155                 160

Glu Ala Cys Arg Pro Ala Ala Gly Gly Ala Val His Thr Arg Gly Leu
                165                 170                 175

Asp Phe Ala Cys Asp Ile Tyr Ile Trp Ala Pro Leu Ala Gly Thr Cys
                180                 185                 190

Gly Val Leu Leu Leu Ser Leu Val Ile Thr Leu Tyr Cys Arg Val Lys
                195                 200                 205

Phe Ser Arg Ser Ala Asp Ala Pro Ala Tyr Gln Gln Gly Gln Asn Gln
    210                 215                 220

Leu Tyr Asn Glu Leu Asn Leu Gly Arg Arg Glu Glu Tyr Asp Val Leu
225                 230                 235                 240

Asp Lys Arg Arg Gly Arg Asp Pro Glu Met Gly Gly Lys Pro Arg Arg
                245                 250                 255

Lys Asn Pro Gln Glu Gly Leu Tyr Asn Glu Leu Gln Lys Asp Lys Met
                260                 265                 270

Ala Glu Ala Tyr Ser Glu Ile Gly Met Lys Gly Glu Arg Arg Arg Gly
                275                 280                 285

Lys Gly His Asp Gly Leu Tyr Gln Gly Leu Ser Thr Ala Thr Lys Asp
    290                 295                 300

Thr Tyr Asp Ala Leu His Met Gln Ala Leu Pro Pro Arg
305                 310                 315
```

<210> SEQ ID NO 20
<211> LENGTH: 336
<212> TYPE: DNA
<213> ORGANISM: Artificial Sequence
<220> FEATURE:
<223> OTHER INFORMATION: CD3

<400> SEQUENCE: 20

```
agagtgaagt tcagcaggag cgcagacgcc cccgcgtacc agcagggcca gaaccagctc        60
tataacgagc tcaatctagg acgaagagag gagtacgatg ttttggacaa gagacgtggc       120
cgggaccctg agatgggggg aaagccgaga aggaagaacc ctcaggaagg cctgtacaat       180
gaactgcaga aagataagat ggcggaggcc tacagtgaga ttgggatgaa aggcgagcgc       240
```

-continued

```
cggaggggca aggggcacga tggcctttac cagggtctca gtacagccac caaggacacc        300
tacgacgccc ttcacatgca ggccctgccc cctcgc                                  336
```